United States Patent
Finlay

(10) Patent No.: US 11,673,960 B2
(45) Date of Patent: Jun. 13, 2023

(54) ANTI C-MET ANTIBODIES

(71) Applicant: LOCKBODY THERAPEUTICS LTD, Altrincham (GB)

(72) Inventor: William James Jonathan Finlay, Sandwich (GB)

(73) Assignee: LOCKBODY THERAPEUTICS LTD, Altrincham (GB)

(*) Notice: Subject to any disclaimer, the term of this patent is extended or adjusted under 35 U.S.C. 154(b) by 65 days.

(21) Appl. No.: 16/980,015

(22) PCT Filed: Mar. 12, 2019

(86) PCT No.: PCT/EP2019/056178
§ 371 (c)(1),
(2) Date: Sep. 11, 2020

(87) PCT Pub. No.: WO2019/175186
PCT Pub. Date: Sep. 19, 2019

(65) Prior Publication Data
US 2021/0009694 A1   Jan. 14, 2021

(30) Foreign Application Priority Data

Mar. 12, 2018 (GB) .................................... 1803892
Jul. 31, 2018 (GB) .................................... 1812487
Oct. 16, 2018 (GB) .................................... 1816841

(51) Int. Cl.
C07K 16/28 (2006.01)

(52) U.S. Cl.
CPC ...... C07K 16/2863 (2013.01); *C07K 2317/31* (2013.01); *C07K 2317/52* (2013.01); *C07K 2317/565* (2013.01); *C07K 2317/92* (2013.01); *C07K 2317/94* (2013.01)

(58) Field of Classification Search
None
See application file for complete search history.

(56) References Cited

U.S. PATENT DOCUMENTS

2010/0129369 A1   5/2010   Davies et al.

FOREIGN PATENT DOCUMENTS

| JP | 2012509881 A | 4/2012 |
| WO | WO 2010/069765 A1 | 6/2010 |
| WO | WO 2013/169532 A1 | 11/2013 |

OTHER PUBLICATIONS

International Search Report and Written Opinion dated Jun. 18, 2019 for International Application No. PCT/EP2019/056178, 14 pages.
Townsend, S. et al., "Augmented Binary Substitution: Single-pass CDR germlining and stabilization of therapeutic antibodies," PNAS, 112(50):15354-15359 (2015).

*Primary Examiner* — Marianne P Allen
(74) *Attorney, Agent, or Firm* — Cooley LLP; Ivor Elrifi

(57) ABSTRACT

The present disclosure relates to antibody molecules that bind specifically to C-MET and related nucleic acid molecules, vectors and host cells. Also provided are medical uses of such antibody molecules. The claimed anti C-Met antibodies of the present application have been selected by in silico engineering. Some of the antibodies have been generated and further characterized after expression in mammalian expression system.

28 Claims, 18 Drawing Sheets

Specification includes a Sequence Listing.

ANTI C-MET ANTIBODIES

CROSS-REFERENCE TO RELATED APPLICATIONS

This application is a 35 U.S.C. § 371 national phase application of International Patent Application No. PCT/EP2019/056178, filed on Mar. 12, 2019, which claims the benefit of GB Patent Application No. 1816841.9, filed on Oct. 16, 2018, GB Patent Application No. 1812487.5, filed on Jul. 31, 2018, and GB Patent Application No. 1803892.7, filed on Mar. 12, 2018, the disclosure of each of which is hereby incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: ULSL_001_03US_SeqList_ST25.txt, date recorded: Sep. 11, 2020, file size 126,236 bytes).

FIELD OF THE INVENTION

The invention relates to antibody molecules binding specifically to C-MET (also known as MET, MET proto-oncogene, receptor tyrosine kinase, AUTS9, HGFR, RCCP2, DFNB97, OSFD) and medical uses thereof.

BACKGROUND OF THE INVENTION

C-MET (also known as MET, MET proto-oncogene, receptor tyrosine kinase, AUTS9, HGFR, RCCP2, DFNB97, OSFD) is a transmembrane protein that belongs to the immunoglobulin superfamily and binds to the soluble factor HGF (hepatocyte growth factor), which is principally produced by mesenchymal cells. C-MET is a single-pass receptor tyrosine kinase that is expressed as a primary single chain precursor protein that is then post-translationally cleaved to produce alpha and beta subunits, which are disulfide linked to form the mature receptor. C-MET is mainly expressed by epithelial cells and has also been observed on multiple other cell types, such as endothelial cells, neurons, hepatocytes, hematopoietic cells, melanocytes and neonatal cardiomyocytes. On binding to HGF, this receptor dimerises, activating its tyrosine kinase activity. This kinase activation leads to further downstream activation of signal transduction molecules that play known roles in cell survival, proliferation, and differentiation.

Genetic amplification and/or overexpression of C-MET is strongly associated with the progression of several important types of cancer, such as Non-Small Cell Lung (NSCLC), Gastric cancer, Pancreatic cancer, Uveal Melanoma, and Papillary Renal Cell Carcinoma. Preclinical and clinical evidence suggests that blocking C-MET/HGF signalling can have clear therapeutic benefit in multiple cancers, but this has predominantly been achieved using small molecule inhibitors of C-MET kinase function. Resistance mutations commonly develop after tyrosine kinase inhibitor treatment, causing therapeutic efficacy to be lost. Therapeutic antibodies that antagonise C-MET signalling by blocking the ability of the receptors to dimerise have the potential to mediate anti-tumour effects via two mechanisms: 1. Potent inhibition of the MET signalling pathway by locking the receptors into a non-activating monomeric form. 2. Antibody effector-function mediated engagement of immune cells.

The majority of currently approved antibody therapeutics are derived from immunized rodents. Many of those antibodies have undergone a process known as "humanization", via the "grafting" of murine Complementarity-Determining Regions (CDRs) into human v-gene framework sequences (see Nelson et al., 2010, Nat Rev Drug Discov 9: 767-774). This process is often inaccurate and leads to a reduction in target binding affinity of the resulting antibody. To return the binding affinity of the original antibody, murine residues are usually introduced at key positions in the variable domain frameworks of the grafted v-domains (also known as "back-mutations").

While antibodies humanized via CDR grafting and back mutations have been shown to induce lower immune response rates in the clinic in comparison to those with fully murine v-domains, antibodies humanized using this basic grafting method still carry significant clinical development risks due to the potential physical instability and immunogenicity motifs still housed in the grafted CDR loops. Antibodies such as anti-C-MET, which potentially engage immune effector functions as part of their mechanism of action, are at particularly high risk of immunogenicity as they can encourage phagocytosis of C-MET+ target cells, leading to antigen processing of the antibody along with the target cell. As animal testing of protein immunogenicity is often non-predictive of immune responses in man, antibody engineering for therapeutic use focuses on minimizing predicted human T-cell epitope content, non-human germline amino acid content and aggregation potential in the purified protein.

The ideal humanized antagonistic anti-C-MET antibody would therefore have as many residues as possible in the v-domains that are identical to those found in both the frameworks and CDRs of well-characterized human germline sequences. This high level of identity to high-stability germlines that are highly expressed in the maximum number of potential patients minimises the risk of a therapeutic antibody having unwanted immunogenicity in the clinic, or unusually high 'cost of goods' in manufacturing.

Townsend et al. (2015; PNAS 112: 15354-15359) describe a method for generating antibodies in which CDRs derived from rat, rabbit and mouse antibodies were grafted into preferred human frameworks and then subject to a human germ-lining approach termed "Augmented Binary Substitution". Although the approach demonstrated a fundamental plasticity in the original antibody paratopes, in the absence of highly accurate antibody-antigen co-crystal structural data, it is still not possible to reliably predict which individual residues in the CDR loops of any given antibody can be converted to human germline, and in what combination. Additionally, the Townsend et al. study did not address the addition of mutagenesis beyond the residues found in the human germline at positions where the removal of development risk motifs might be beneficial. This is a technological limitation which renders the process inherently inefficient, requiring an extra stage of modification of the starting antibody sequence. In addition, it cannot currently be accurately predicted what modifications in distal positions of the protein sequence of an individual v-domain, or even on the partner v-domain, might facilitate the removal of risk motifs while maintaining antigen binding affinity and specificity.

CDR germ-lining and development quality optimisation is thus a complex, multifactorial problem, as multiple functional properties of the molecule should preferably be maintained, including in this instance: target binding specificity, affinity to C-MET from both human and animal test species (e.g. cynomolgus monkey, also known as the crab-eating macaque, i.e. *Macaca fascicularis*), v-domain biophysical stability and/or IgG yield from protein expression platforms used in research, clinical and commercial supply. Antibody engineering studies have shown that mutation of even single residue positions in key CDRs can have dramatic effects on all of these desired molecular properties.

WO2011151412A1 describes an antagonistic murine anti-C-MET IgG molecule termed "224G11", and also the preparation of humanized forms (h224G11). Those humanized forms of 224G11 were produced using classical humanization techniques, i.e. by grafting of Kabat-defined murine CDRs into human heavy and light chain framework sequences, with some of the human framework residues being potentially back-mutated to the correspondingly positioned 224G11 murine residues. For reasons noted above, such humanized forms of 224G11 described in WO2011151412A1 are not ideal.

SUMMARY OF THE INVENTION

The present invention provides a number of anti-C-MET antibodies and medical uses thereof.

According to one aspect of the invention, there is provided an antibody molecule which specifically binds to human C-MET, and optionally also to cynomolgus monkey C-MET, or an antigen-binding portion thereof, wherein the antibody molecule or antigen-binding portion comprises a heavy chain variable region with:

an HCDR1 having amino acids in sequence in the following order: G-Y-I or any amino acid (such as T)-F-T-A or any amino acid (such as S)-Y-Y or any amino acid (such as A, S or T)-M-H (SEQ ID NO: 22);

an HCDR2 having amino acids in sequence in the following order: M-G-W or any amino acid (such as I)-I-K or any amino acid (such as N)-P-N or any amino acid (such as S)-N or any amino acid (such as G)-G-L or any amino acid (such as S)-A or any amino acid (such as T)-N or any amino acid (such as S)-Y-A-Q-K-F-Q-G (SEQ ID NO: 23); and an HCDR3 having amino acids in sequence in the following order: S or any amino acid (such as A/E/H/M/Q/T/V)-E-I-T-T-E or any amino acid (such as D)-F or any amino acid (such as L)-D-Y or any amino acid (such as A/E/F/I/K/L/M/Q/S/V/W) (SEQ ID NO: 24).

In aspects of the invention, the HCDR1 of the antibody molecule or antigen-binding portion may exclude the sequence GYIFTAYTMH (SEQ ID NO: 25; 224G11 murine/humanized antibody HCDR1 disclosed in WO2011151412A1; US 2013/0216527A1), the HCDR2 of the antibody molecule or antigen-binding portion may exclude the sequence MGWIKPNNGLANYAQKFQG (SEQ ID NO: 26; 224G11 murine/humanized antibody HCDR1 disclosed in WO2011151412A1; US 2013/0216527A1), and/or the HCDR3 of the antibody molecule or antigen-binding portion may exclude the sequence SEIT-TEFDY (SEQ ID NO: 27; 224G11 murine/humanized antibody HCDR3 disclosed in WO2011151412A1; US 2013/0216527A1).

The antibody molecule or antigen-binding portion may further comprise a light chain variable region with:
an LCDR1 having amino acids in sequence in the following order: R-A-S-Q-S-V-D or any amino acid (for example, S or E)-S-Y-A-N or any amino acid (for example, Q)-S-F or any amino acid (for example, Y)-L-H or any amino acid (for example, A) (SEQ ID NO: 28);
an LCDR2 having amino acids in sequence in the following order: R or any amino acid (for example, A)-A or any amino acid (for example, G)-S-T or any amino acid (for example, S)-R-E-S or any amino acid (for example, T) (SEQ ID NO: 29); and
an LCDR3 having amino acids in sequence in the following order: Q-Q-S or any amino acid (for example, Y)-K or any amino acid (for example, G)-E or any amino acid (for example, D, S)-D or any amino acid (for example, S, E, R)-P-L-T (SEQ ID NO: 30).

In aspects of the invention, the LCDR1 of the antibody molecule or antigen-binding portion may exclude the sequence KSSESVDSYANSFLH (SEQ ID NO: 31; 224G11 murine/humanized antibody LCDR1 disclosed in WO2011151412A1; US 2013/0216527A1), and/or the LCDR2 of the antibody molecule or antigen-binding portion may exclude the sequence RASTRES (SEQ ID NO: 32; 224G11 murine/humanized antibody LCDR2 disclosed in WO2011151412A1; US 2013/0216527A1), and/or the LCDR3 of the antibody molecule or antigen-binding portion may exclude the sequence QQSKEDPLT (SEQ ID NO: 33; 224G11 murine/humanized antibody LCDR3 disclosed in WO2011151412A1; US 2013/0216527A1).

In some aspects, disclosed herein is an anti-C-MET antibody or an antigen-binding portion thereof, wherein the antibody comprises a heavy chain variable (VH) region and a light chain variable (VL) region, wherein
(a) the HCDR1 comprises the amino acid sequence G-Y-$X_1$-F-T-$X_2$-Y-$X_3$-M-H, wherein $X_1$ is I or any other amino acid, $X_2$ is A or any other amino acid and $X_3$ is Y or any other amino acid (SEQ ID NO: 22);
(b) the HCDR2 comprises M-G-$X_1$-I-$X_2$-P-$X_3$-$X_4$-G-$X_5$-$X_6$-$X_7$-Y-A-Q-K-F-Q-G, wherein $X_1$ is W or any other amino acid, $X_2$ is K or any other amino acid, $X_3$ is N or any other amino acid, $X_4$ is N or any other amino acid, $X_5$ is L or any other amino acid, $X_6$ is A or any other amino acid and $X_7$ is N or any other amino acid (SEQ ID NO: 23);
(c) the HCDR3 comprises $X_1$-E-I-T-T-$X_2$-$X_3$-D-$X_4$, wherein $X_1$ is S or any other amino acid, $X_2$ is E or any other amino acid, $X_3$ is F or any other amino acid and $X_4$ is Y or any other amino acid (SEQ ID NO: 24);
(d) the LCDR1 comprises R-A-S-Q-S-V-$X_1$-S-Y-A-$X_2$-S-$X_3$-L-$X_4$, wherein $X_1$ is D or any other amino acid, $X_2$ is N or any other amino acid, $X_3$ is F or any other amino acid of F and $X_4$ is H or any other amino acid (SEQ ID NO: 28);
(e) the LCDR2 comprises $X_1$-$X_2$-S-$X_3$-R-E-$X_4$, wherein $X_1$ is R or any other amino acid, $X_2$ is A or any other amino acid, $X_3$ is T or any other amino acid and $X_4$ is S or any other amino acid (SEQ ID NO: 29); and
(f) the LCDR3 comprises Q-Q-$X_1$-$X_2$-$X_3$-$X_4$-P-L-T, wherein $X_1$ is S or any other amino acid, $X_2$ is K or any other amino acid, $X_3$ is E or any other amino acid and $X_4$ is D or any other amino acid (SEQ ID NO: 30).

In some aspects, the invention provides an anti-C-MET antibody or an antigen-binding portion thereof, wherein the antibody comprises a heavy chain variable (VH) region and a light chain variable (VL) region, wherein
(a) the VH region amino acid sequence comprises HCDR1 of GYTFTSYTMH (SEQ ID NO: 34), HCDR2 of MGIINPSGGSTSYAQKFQG (SEQ ID NO: 35) and HCDR3 of QEITTEFDY (SEQ ID NO: 36); and the VL region amino acid sequence comprises LCDR1 of RASQSVSSYAQSYLH (SEQ ID NO: 57), LCDR2 of RGSTRET (SEQ ID NO: 56) and LCDR3 of QQSKESPLT (SEQ ID NO: 47);
(b) the VH region amino acid sequence comprises HCDR1 of GYTFTSYTMH (SEQ ID NO: 34), HCDR2 of MGIINPSGGSTSYAQKFQG (SEQ ID NO: 35) and HCDR3 of QEITTEFDY (SEQ ID NO: 36); and the VL region amino acid sequence comprises LCDR1 of RASQSVSSYANSYLH (SEQ ID NO: 37), LCDR2 of RGSTRET (SEQ ID NO: 56) and LCDR3 of QQSKESPLT (SEQ ID NO: 47);

(c) the VH region amino acid sequence comprises HCDR1 of GYTFTSYTMH (SEQ ID NO: 34), HCDR2 of MGIINPSGGSTSYAQKFQG (SEQ ID NO: 35) and HCDR3 of QEITTEFDY (SEQ ID NO: 36); and the VL region amino acid sequence comprises LCDR1 of RASQSVSSYANSYLH (SEQ ID NO: 37), LCDR2 of RGSTRET (SEQ ID NO: 56) and LCDR3 of QQSKSEPLT (SEQ ID NO: 39);

(d) the VH region amino acid sequence comprises HCDR1 of GYTFTSYTMH (SEQ ID NO: 34), HCDR2 of MGIINPSGGSTSYAQKFQG (SEQ ID NO: 35) and HCDR3 of QEITTEFDY (SEQ ID NO: 36); and the VL region amino acid sequence comprises LCDR1 of RASQSVSSYANSYLH (SEQ ID NO: 37), LCDR2 of RGSTRES (SEQ ID NO: 38) and LCDR3 of QQSKSEPLT (SEQ ID NO: 39);

(e) the VH region amino acid sequence comprises HCDR1 of GYTFTSYTMH (SEQ ID NO: 34), HCDR2 of MGWINPSGGLANYAQKFQG (SEQ ID NO: 54) and HCDR3 of SEITTDFDY (SEQ ID NO: 55); and the VL region amino acid sequence comprises LCDR1 of RASQSVDSYANSYLH (SEQ ID NO: 51), LCDR2 of RGSTRES (LCDR2; SEQ ID NO: 38) and LCDR3 of QQSKSEPLT (SEQ ID NO: 39);

(f) the VH region amino acid sequence comprises HCDR1 of GYTFTSYTMH (SEQ ID NO: 34), HCDR2 of MGWINPSGGSTSYAQKFQG (SEQ ID NO: 40) and HCDR3 of QEITTEFDY (SEQ ID NO: 36); and the VL region amino acid sequence comprises LCDR1 of RASQSVSSYANSYLH (SEQ ID NO: 37), LCDR2 of RGSTRES (SEQ ID NO: 38) and LCDR3 of QQSKSEPLT (SEQ ID NO: 39);

(g) the VH region amino acid sequence comprises HCDR1 of GYTFTSYAMH (SEQ ID NO: 41), HCDR2 of MGWINPSGGSTSYAQKFQG (SEQ ID NO: 40) and HCDR3 of QEITTEFDY (SEQ ID NO: 36); and the VL region amino acid sequence comprises LCDR1 of RASQSVSSYANSYLH (SEQ ID NO: 37), LCDR2 of RGSTRES (SEQ ID NO: 38) and LCDR3 of QQSKSEPLT (SEQ ID NO: 39);

(h) the VH region amino acid sequence comprises HCDR1 of GYTFTSYTMH (SEQ ID NO: 34), HCDR2 of MGWINPNGGSTSYAQKFQG (SEQ ID NO: 42) and HCDR3 of QEITTEFDY (SEQ ID NO: 36); and the VL region amino acid sequence comprises LCDR1 of RASQSVSSYANSYLH (SEQ ID NO: 37), LCDR2 of RGSTRES (SEQ ID NO: 38) and LCDR3 of QQSKSEPLT (SEQ ID NO: 39);

(i) the VH region amino acid sequence comprises HCDR1 of GYIFTSYSMH (SEQ ID NO: 43), HCDR2 of MGWINPSNGLANYAQKFQG (SEQ ID NO: 44) and HCDR3 of QEITTEFDI (SEQ ID NO: 45); and the VL region amino acid sequence comprises LCDR1 of RASQSVESYAQSYLH (SEQ ID NO: 46), LCDR2 of RGSTRES (SEQ ID NO: 38) and LCDR3 of QQSKSDPLT (SEQ ID NO: 76);

(j) the VH region amino acid sequence comprises HCDR1 of GYIFTSYTMH (SEQ ID NO: 48), HCDR2 of MGWINPNGGLASYAQKFQG (SEQ ID NO: 49) and HCDR3 of SEITTEQDY (SEQ ID NO: 50); and the VL region amino acid sequence comprises LCDR1 of RASQSVDSYANSYLH (SEQ ID NO: 51), LCDR2 of RGSTRES (SEQ ID NO: 38) and LCDR3 of QQSKESPLT (SEQ ID NO: 47); or (k) the VH region amino acid sequence comprises HCDR1 of GYIFTSYTMH (SEQ ID NO: 48), HCDR2 of MGWINPNGGSTSYAQKFQG (SEQ ID NO: 42) and HCDR3 of QEITTEFDY (SEQ ID NO: 36); and the VL region amino acid sequence comprises LCDR1 of RASQSVESYANSYLH (SEQ ID NO: 52), LCDR2 of RGSTRES (SEQ ID NO: 38) and LCDR3 of QQYGSEPLT (SEQ ID NO: 53).

In some aspects, disclosed herein is an anti-C-MET antibody or an antigen-binding portion thereof, wherein the antibody comprises a heavy chain variable (VH) region and a light chain variable (VL) region, wherein the VH region amino acid sequence comprises:

(a) HCDR1 of SEQ ID NO: 34, SEQ ID NO: 41, SEQ ID NO: 43 or SEQ ID NO: 48;

(b) HCDR2 of SEQ ID NO: 35, SEQ ID NO: 40, SEQ ID NO: 42, SEQ ID NO: 44, SEQ ID NO: 49 or SEQ ID NO: 54; and (c) HCDR3 of SEQ ID NO: 36, SEQ ID NO: 45, SEQ ID NO: 50 or SEQ ID NO: 55; and the VL region amino acid sequence comprises:

(a') LCDR1 of SEQ ID NO: 37, SEQ ID NO: 46, SEQ ID NO: 51, SEQ ID NO: 52 or SEQ ID NO: 57;

(b') LCDR2 of SEQ ID NO: 38 or SEQ ID NO: 56; and (c') LCDR3 of SEQ ID NO: 39, SEQ ID NO: 47, SEQ ID NO: 53 or SEQ ID NO: 76.

In some aspects, disclosed herein is an anti-C-MET antibody or an antigen-binding portion thereof, wherein the antibody comprises a heavy chain variable (VH) region and a light chain variable (VL) region, wherein (a) the VH region amino acid sequence comprises SEQ ID NO:1 and the VL region amino acid sequence comprises SEQ ID NO:2;

(b) the VH region amino acid sequence comprises SEQ ID NO:3 and the VL region amino acid sequence comprises SEQ ID NO:4;

(c) the VH region amino acid sequence comprises SEQ ID NO:5 and the VL region amino acid sequence comprises SEQ ID NO:6;

(d) the VH region amino acid sequence comprises SEQ ID NO:7 and the VL region amino acid sequence comprises SEQ ID NO:8; or (e) the VH region amino acid sequence comprises SEQ ID NO:9 and the VL region amino acid sequence comprises SEQ ID NO:10.

Also provided according to the invention is an immunoconjugate comprising the antibody molecule or antigen-binding portion thereof as defined herein linked, fused or conjugated to a therapeutic agent.

In another aspect the invention provides a nucleic acid molecule encoding the antibody molecule or antigen-binding portion thereof as defined herein.

Further provided is a vector comprising the nucleic acid molecule of the invention.

Also provided is a host cell comprising the nucleic acid molecule or the vector of the invention as defined herein.

In a further aspect there is provided a method of producing an anti-C-MET antibody and/or an antigen-binding portion thereof, comprising culturing the host cell of the invention under conditions that result in expression and/or production of the antibody and/or the antigen-binding portion thereof, and isolating the antibody and/or the antigen-binding portion thereof from the host cell or culture.

In another aspect of the invention there is provided a pharmaceutical composition comprising the antibody molecule or antigen-binding portion thereof of the invention as defined herein, or the nucleic acid molecule of the invention as defined herein, or the vector of the invention as defined herein.

Further provided is a method for enhancing an immune response in a subject, comprising administering an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

In a further aspect there is provided a method for treating or preventing cancer in a subject, comprising administering an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

Further provided herein is an antibody molecule or antigen-binding portion thereof as defined herein, or the immunoconjugate as defined herein, or the nucleic acid molecule as defined herein, or the vector as defined herein, or the pharmaceutical composition as defined herein, for use as a medicament. The invention also provides an antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein, for use in the treatment of cancer.

In another aspect the invention provides the antibody molecule, or antigen-binding portion thereof, or the immunoconjugate, or the nucleic acid molecule, or the vector for use, or the method of treatment of the invention as defined herein, for separate, sequential or simultaneous use in a combination with a second therapeutic agent, for example an anti-cancer agent.

In a further aspect there is provided the use of an antibody molecule or antigen-binding portion thereof of the invention as defined herein, or an immunoconjugate of the invention as defined herein, or a nucleic acid molecule of the invention as defined herein, or a vector of the invention as defined herein, or a pharmaceutical composition of the invention as defined herein, in the manufacture of a medicament for the treatment of cancer.

The invention also provides a method for treating or preventing an autoimmune disease or an inflammatory disease in a subject, comprising administering an effective amount of the antibody molecule or antigen-binding portion thereof as defined herein, or the immunoconjugate as defined here, or the nucleic acid molecule as defined herein, or the vector as defined herein, or the pharmaceutical composition as defined herein.

For example, the autoimmune disease or inflammatory disease may be arthritis, asthma, multiple sclerosis, psoriasis, Crohn's disease, inflammatory bowel disease, lupus, Grave's disease, Hashimoto's thyroiditis, or ankylosing spondylitis.

Also provided is an antibody molecule or antigen-binding portion thereof as defined herein, or the immunoconjugate as defined herein, or the nucleic acid molecule as defined herein, or the vector as defined herein, or the pharmaceutical composition as defined herein, for use in the treatment of an autoimmune disease or an inflammatory disease.

Further provided is the use of an antibody molecule or antigen-binding portion thereof as defined herein, or an immunoconjugate as defined herein, or a nucleic acid molecule as defined herein, or a vector as defined herein, or a pharmaceutical composition as defined herein, in the manufacture of a medicament for the treatment of an autoimmune disease or an inflammatory disease.

The invention also provides a method for treating or preventing a cardiovascular disease or a fibrotic disease in a subject, comprising administering an effective amount of the antibody molecule or antigen-binding portion thereof as defined herein, or the immunoconjugate as defined here, or the nucleic acid molecule as defined herein, or the vector as defined herein, or the pharmaceutical composition as defined herein.

Also provided is an antibody molecule or antigen-binding portion thereof as defined herein, or the immunoconjugate as defined herein, or the nucleic acid molecule as defined herein, or the vector as defined herein, or the pharmaceutical composition as defined herein, for use in the treatment of a cardiovascular disease or a fibrotic disease.

Further provided is the use of an antibody molecule or antigen-binding portion thereof as defined herein, or an immunoconjugate as defined herein, or a nucleic acid molecule as defined herein, or a vector as defined herein, or a pharmaceutical composition as defined herein, in the manufacture of a medicament for the treatment of an autoimmune disease, an inflammatory disease or a fibrotic disease.

The cardiovascular disease in any aspect of the invention may for example be coronary heart disease or atherosclerosis.

The fibrotic disease in any aspect of the invention may be selected from the group consisting of myocardial infarction, angina, osteoarthritis, pulmonary fibrosis, cystic fibrosis, bronchitis and asthma.

The invention also provides a method of producing an antibody molecule which specifically binds to human C-MET and optionally also to cynomolgus monkey C-MET, or an antigen-binding portion thereof, comprising the steps of:
(1) grafting anti-C-MET CDRs from a non-human source into a human v-domain framework to produce a humanized anti-C-MET antibody molecule or antigen-binding portion thereof;
(2) generating a phage library of clones of the humanized anti-C-MET antibody molecule or antigen-binding portion thereof comprising one or more mutations in the CDRs;
(3) screening the phage library for binding to human C-MET and optionally also to cynomolgus monkey C-MET;
(4) selecting clones from the screening step (3) having binding specificity to human C-MET and optionally also to cynomolgus monkey C-MET; and
(5) producing an antibody molecule which specifically binds to human C-MET and optionally also to cynomolgus monkey C-MET, or an antigen-binding portion thereof from clones selected from step (4).

The method may comprise a further step of producing additional clones based on the clones selected in step (4), for example based on further exploratory mutagenesis at specific positions in the CDRs of the clones selected in step (4), to enhance humanization and/or minimise human T cell epitope content and/or improve manufacturing properties in the antibody molecule or antigen-binding portion thereof produced in step (5).

BRIEF DESCRIPTION OF THE FIGURES

FIG. 10A: (1) h224G11 and (2) 08G07; FIG. 10B: (3) MH7 and (4) MH7-1; FIG. 10C: (5) MH7-2 and (6) MH7-3. In all panels, signal is measured in Fluorescence Units.

DETAILED DESCRIPTION OF THE INVENTION

Figure 1A:
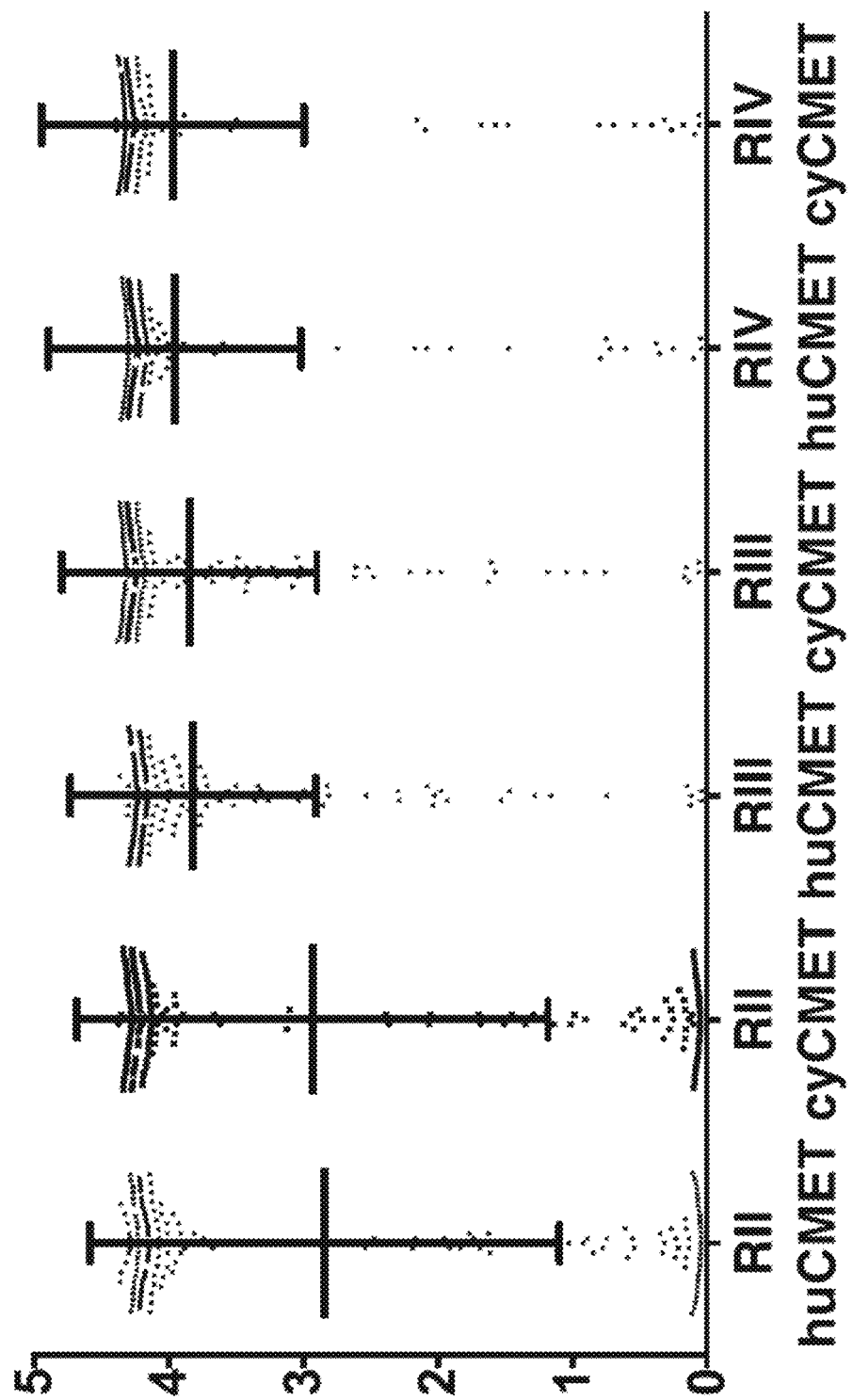
FIG. 1A-FIG. 1B. Direct binding ELISA and Alphascreen competition screening of library-derived anti-C-MET Fabs against human and cyno C-MET-Fc proteins. Clones were derived from multiple phage selection branches where phage populations were selected on biotinylated human, or cynomolgus monkey C-MET proteins in each of rounds II-IV. After each round of selection, library-derived clones were screened as periplasmically-expressed Fab proteins, against both human (huCMET) and cyno (cyCMET) in ELISA (FIG. 1A), and in blocking the binding of 224G11 IgG in binding to huCMET by Alphascreen (FIG. 1B). Mean±SD values in each round are represented in grey bars.

According to a first aspect of the invention, there is provided an antibody molecule which specifically binds to human C-MET and optionally also to cynomolgus monkey C-MET, or an antigen-binding portion thereof, wherein the antibody molecule or antigen-binding portion comprises a heavy chain variable region with:

an HCDR1 having amino acids in sequence in the following order: G-Y-I or any amino acid (such as T)-F-T-A or any amino acid (such as S)-Y-Y or any amino acid (such as A, S or T)-M-H (SEQ ID NO: 22);

an HCDR2 having amino acids in sequence in the following order: M-G-W or any amino acid (such as I)-I-K or any amino acid (such as N)-P-N or any amino acid (such as S)-N or any amino acid (such as G)-G-L or any amino acid (such as S)-A or any amino acid (such as T)-N or any amino acid (such as S)-Y-A-Q-K-F-Q-G (SEQ ID NO: 23); and an HCDR3 having amino acids in sequence in the following order: S or any amino acid (such as A/E/H/M/Q/T/V)-E-I-T-T-E or any amino acid (such as D)-F or any amino acid (such as L)-D-Y or any amino acid (such as A/E/F/I/K/L/M/Q/S/V/W) (SEQ ID NO: 24).

In some aspects an anti-C-MET antibody or antigen-binding portion provided herein specifically binds to a C-MET protein comprising or consisting of SEQ ID NO:18 or SEQ ID NO:19. In some aspects an anti-C-MET antibody or antigen-binding portion provided herein specifically binds to a C-MET protein having an amino acid sequence that is at least about 90%, at least about 91%, at least about 92%, at least about 93%, at least about 94%, at least about 95%, at least about 96%, at least about 97%, at least about 98% or at least about 99% identical to SEQ ID NO:18 or SEQ ID NO:19.

In aspects of the invention, the HCDR1 of the antibody molecule or antigen-binding portion may exclude the sequence GYIFTAYTMH (SEQ ID NO: 25; 224G11 murine/humanized antibody HCDR1 disclosed in WO2011151412A1; US 2013/0216527A1), the HCDR2 of the antibody molecule or antigen-binding portion may exclude the sequence MGWIKPNNGLANYAQKFQG (SEQ ID NO: 26; 224G11 murine/humanized antibody HCDR1 disclosed in WO2011151412A1; US 2013/0216527A1), and/or the HCDR3 of the antibody molecule or antigen-binding portion may exclude the sequence SEIT-TEFDY (SEQ ID NO: 27; 224G11 murine/humanized antibody HCDR3 disclosed in WO2011151412A1; US 2013/0216527A1).

The antibody molecule or antigen-binding portion may further comprise a light chain variable region with:
an LCDR1 having amino acids in sequence in the following order: R-A-S-Q-S-V-D or any amino acid (for example, S or E)-S-Y-A-N or any amino acid (for example, Q)-S-F or any amino acid (for example, Y)-L-H or any amino acid (for example, A) (SEQ ID NO: 28); an LCDR2 having amino acids in sequence in the following order: R or any amino acid (for example, A)-A or any amino acid (for example, G)-S-T or any amino acid (for example, S)-R-E-S or any amino acid (for example, T) (SEQ ID NO: 29); and
an LCDR3 having amino acids in sequence in the following order: Q-Q-S or any amino acid (for example, Y)-K or any amino acid (for example, G)-E or any amino acid (for example, D, S)-D or any amino acid (for example, S, E, R)-P-L-T (SEQ ID NO: 30).

In aspects of the invention, the LCDR1 of the antibody molecule or antigen-binding portion may exclude the sequence KSSESVDSYANSFLH (SEQ ID NO: 31; 224G11 murine/humanized antibody LCDR1 disclosed in WO2011151412A1; US 2013/0216527A1), and/or the LCDR2 of the antibody molecule or antigen-binding portion may exclude the sequence RASTRES (SEQ ID NO: 32; 224G11 murine/humanized antibody LCDR2 disclosed in WO2011151412A1; US 2013/0216527A1), and/or the LCDR3 of the antibody molecule or antigen-binding portion may exclude the sequence QQSKEDPLT (SEQ ID NO: 33; 224G11 murine/humanized antibody LCDR3 disclosed in WO2011151412A1; US 2013/0216527A1).

In some aspects, disclosed herein is an anti-C-MET antibody or an antigen-binding portion thereof, wherein the antibody comprises a heavy chain variable (VH) region and a light chain variable (VL) region, wherein
(a) the HCDR1 comprises the amino acid sequence G-Y-$X_1$-F-T-$X_2$-Y-$X_3$-M-H, wherein $X_1$ is I or any other amino acid, $X_2$ is A or any other amino acid and $X_3$ is Y or any other amino acid (SEQ ID NO: 22);
(b) the HCDR2 comprises M-G-$X_1$-I-$X_2$-P-$X_3$-$X_4$-G-$X_5$-$X_6$-$X_7$-Y-A-Q-K-F-Q-G, wherein $X_1$ is W or any other amino acid, $X_2$ is K or any other amino acid, $X_3$ is N or any other amino acid, $X_4$ is N or any other amino acid, $X_5$ is L or any other amino acid, $X_6$ is A or any other amino acid and $X_7$ is N or any other amino acid (SEQ ID NO: 23);
(c) the HCDR3 comprises $X_1$-E-I-T-T-$X_2$-$X_3$-D-$X_4$, wherein $X_1$ is S or any other amino acid, $X_2$ is E or any other amino acid, $X_3$ is F or any other amino acid and $X_4$ is Y or any other amino acid (SEQ ID NO: 24);
(d) the LCDR1 comprises R-A-S-Q-S-V-$X_1$-S-Y-A-$X_2$-S-$X_3$-L-$X_4$, wherein $X_1$ is D or any other amino acid, $X_2$ is N or any other amino acid, $X_3$ is F or any other amino acid of F and $X_4$ is H or any other amino acid (SEQ ID NO: 28);
(e) the LCDR2 comprises $X_1$-$X_2$-S-$X_3$-R-E-$X_4$, wherein $X_1$ is R or any other amino acid, $X_2$ is A or any other amino acid, $X_3$ is T or any other amino acid and $X_4$ is S or any other amino acid (SEQ ID NO: 29); and
(f) the LCDR3 comprises Q-Q-$X_1$-$X_2$-$X_3$-$X_4$-P-L-T, wherein $X_1$ is S or any other amino acid, $X_2$ is K or any other amino acid, $X_3$ is E or any other amino acid and $X_4$ is D or any other amino acid (SEQ ID NO: 30). In some aspects, the HCDR1 $X_1$ is T. In some aspects, the HCDR2 $X_3$ is a conservative substitution of N. In some aspects, the HCDR2 $X_4$ is a conservative substitution of N. In some aspects, the HCDR2 $X_7$ is a conservative substitution of N. In some aspects, the LCDR1 $X_2$ is a conservative substitution of N. In some aspects, the LCDR1 $X_3$ is a conservative substitution of F. In some aspects, the LCDR2 $X_3$ is a conservative substitution of T. In some aspects, the LCDR2 $X_4$ is a conservative substitution of S.

In some aspects, disclosed herein is an anti-C-MET antibody or an antigen-binding portion thereof, wherein the antibody comprises a heavy chain variable (VH) region comprising, in amino-terminal to carboxyl-terminal order, FR1-HCDR1-FR2-HCDR2-FR3-HCDR3-FR4 and a light chain variable (VL) region comprising, in amino-terminal to carboxyl-terminal order, FR1-LCDR1-FR2-LCDR2-FR3-LCDR3-FR4, wherein the HCDR1 is SEQ ID NO:22, the HCDR2 is SEQ ID NO:23, the HCDR3 is SEQ ID NO:24, the LCDR1 is SEQ ID NO:28, the LCDR2 is SEQ ID NO:29 and the LCDR3 is SEQ ID NO:30, wherein the heavy chain FR1, FR2, FR3 and FR4 amino acid sequences are the heavy chain FR1, FR2, FR3 and FR4 amino acid sequences in SEQ ID NO: 127 (see Table 2) and wherein the light chain FR1, FR2, FR3 and FR4 amino acid sequences are the light chain FR1, FR2, FR3 and FR4 amino acid sequences in SEQ ID NO: 129 (see Table 2).

As elaborated herein, the present inventors have succeeded for the first time in generating a number of optimized anti-C-MET antibody molecules using CDR sequences derived from the murine anti-C-MET antibody 224G11 disclosed in WO2011151412A1; US 2013/0216527A1. In embodiments of the present invention, these antibody molecules have been selected to have binding specificity to both human C-MET as well as cynomolgus monkey C-MET (to facilitate in vivo studies in an appropriate animal test species). Further refining of the optimized antibody molecules as described herein has provided improved variable domain stability, higher expression yields, and/or reduced immunogenicity.

Preferred optimized anti-C-MET antibody molecules of the present invention do not necessarily have the maximum number of human germline substitutions at corresponding murine CDR or other (such as framework) amino acid positions. As elaborated in the experimental section below, we have found that "maximally humanized" antibody molecules are not necessary "maximally optimized" in terms of anti-C-MET binding characteristics and/or other desirable features.

The present invention encompasses modifications to the amino acid sequence of the antibody molecule or antigen-binding portion thereof as defined herein. For example, the invention includes antibody molecules and corresponding antigen-binding portions thereof comprising functionally equivalent variable regions and CDRs which do not significantly affect their properties as well as variants which have enhanced or decreased activity and/or affinity. For example, the amino acid sequence may be mutated to obtain an antibody with the desired binding affinity to C-MET. Insertions which include amino- and/or carboxyl-terminal fusions ranging in length from one residue to polypeptides containing a hundred or more residues, as well as intrasequence insertions of single or multiple amino acid residues, are envisaged. Examples of terminal insertions include an antibody molecule with an N-terminal methionyl residue or the antibody molecule fused to an epitope tag. Other insertional variants of the antibody molecule include the fusion to the N- or C-terminus of the antibody of an enzyme or a polypeptide which increases the half-life of the antibody in the blood circulation.

The antibody molecule or antigen-binding portion of the invention may include glycosylated and nonglycosylated polypeptides, as well as polypeptides with other post-translational modifications, such as, for example, glycosylation with different sugars, acetylation, and phosphorylation. The antibody molecule or antigen-binding portion of the invention may be mutated to alter such post-translational modifications, for example by adding, removing or replacing one or more amino acid residues to form or remove a glycosylation site.

The antibody molecule or antigen-binding portion of the invention may be modified for example by amino acid substitution to remove potential proteolytic sites in the antibody.

In the antibody molecule or antigen-binding portion thereof, the HCDR1 may have the amino acid sequence: G-Y-I/T-F-T-A/S-Y-Y/S/T/A-M-H (SEQ ID NO: 64); the HCDR2 may have the amino acid sequence: M-G-W/I-I-K/N-P-N/S-N/G-G-L/S-A/T-N/S-Y-A-Q-K-F-Q-G (SEQ ID NO: 65); and the HCDR3 may have the amino acid sequence: S/A/E/H/M/Q/T/V-E-I-T-T-E/D-F/L-D-Y/A/E/F/I/K/L/M/Q/S/V/W (SEQ ID NO: 66).

For example, the HCDR1 may have the amino acid sequence: G-Y-T-F-T-S-Y-A/S/T-M-H (SEQ ID NO: 67); the HCDR2 may have the amino acid sequence: M-G-W/I-I-N-P-S-G-G-S-T-S-Y-A-Q-K-F-Q-G (SEQ ID NO: 68); and the HCDR3 may have the amino acid sequence: S/A/E/Q/T-E-I-T-T-E/D-F-D-Y/I (SEQ ID NO: 69).

In the antibody molecule or antigen-binding portion thereof, the LCDR1 may have the amino acid sequence: R-A-S-Q-S-V-D/S/E-S-Y-A-N/Q-S-F/Y-L-H/A (SEQ ID NO: 70); the LCDR2 may have the amino acid sequence: R/A-A/G-S-T/S-R-E-T/S (SEQ ID NO: 71); and the LCDR3 may have the amino acid sequence: Q-Q-S/Y-K/G-E/D/S-D/S/E/R-P-L-T (SEQ ID NO: 72).

For example, the LCDR1 may have the amino acid sequence: R-A-S-Q-S-V-D/S/E-S-Y-A-N/Q-S-Y-L-H (SEQ ID NO: 73); the LCDR2 may have the amino acid sequence: R-G-S-T-R-E-T/S (SEQ ID NO: 74); and the LCDR3 may have the amino acid sequence: Q-Q-S/Y-K/G-E/S-D/S/E-P-L-T (SEQ ID NO: 75).

In specific embodiments of the invention, the antibody molecule or antigen-binding portion may comprise:

(a) the amino acid sequences RASQSVESYAQSYLH (LCDR1; SEQ ID NO: 46), RGSTRES (LCDR2; SEQ ID NO: 38), QQSKSDPLT (LCDR3; SEQ ID NO: 76), GYIFTSYSMH (HCDR1; SEQ ID NO: 43), MGWINPSNGLAN-YAQKFQG (HCDR2; SEQ ID NO: 44), QEITTEFDI (HCDR3; SEQ ID NO: 45), [Clone 04F09]; or (b) the amino acid sequences RASQSVDSYANSYLH (LCDR1; SEQ ID NO: 51), RGSTRES (LCDR2; SEQ ID NO: 38), QQSKESPLT (LCDR3; SEQ ID NO: 47), GYIFT-SYTMH (HCDR1; SEQ ID NO: 48), MGWINPNG-GLASYAQKFQG (HCDR2; SEQ ID NO: 49), SEITTE-QDY (HCDR3; SEQ ID NO: 50), [Clone 07A01]; or (c) the amino acid sequences RASQSVSSYAQSYLH (LCDR1; SEQ ID NO: 57), RASTRET (LCDR2; SEQ ID NO: 77), QQSKESPLT (LCDR3; SEQ ID NO: 47), GYTFT-SYSMH (HCDR1; SEQ ID NO: 78), MGWINPNG-GLTNYAQKFRG (HCDR2; SEQ ID NO: 79), EEIT-TEFDY (HCDR3; SEQ ID NO: 80), [Clone 09A12]; or (d) the amino acid sequences RASQSVSSYANSYLH (LCDR1; SEQ ID NO: 37), RGSTRES (LCDR2; SEQ ID NO: 38), QQSKSDPLT (LCDR3; SEQ ID NO: 76), GYTFTSYTMH (HCDR1; SEQ ID NO: 34), MGWINPNNGSTNYAQKFQG (HCDR2; SEQ ID NO: 81), SEITTDFDY (HCDR3; SEQ ID NO: 55), [Clone 09B08]; or (e) the amino acid sequences RASQSVESYAQSYLH (LCDR1; SEQ ID NO: 46), RGSTRES (LCDR2; SEQ ID NO: 38), QQSKEEPLT (LCDR3; SEQ ID NO: 82), GYIFTAYSMH (HCDR1; SEQ ID NO: 83), MGIIKPSNG-STNYAQKFQG (HCDR2; SEQ ID NO: 84), AEITTEFDY (HCDR3; SEQ ID NO: 85), [Clone 07C10]; or (f) the amino acid sequences RASQSVESYANSYLH (LCDR1; SEQ ID NO: 52), RGSTRES (LCDR2; SEQ ID NO: 38), QQYGSEPLT (LCDR3; SEQ ID NO: 53), GYIFT-SYTMH (HCDR1; SEQ ID NO: 48), MGWINPNGGST-SYAQKFQG (HCDR2; SEQ ID NO: 42), QEITTEFDY (HCDR3; SEQ ID NO: 36), [Clone 09E04]; or (g) the amino acid sequences RASQSVDSYANSYLH (LCDR1; SEQ ID NO: 51), RGSTRES (LCDR2; SEQ ID NO: 38), QQSKSEPLT (LCDR3; SEQ ID NO: 39), GYTFT-SYTMH (HCDR1; SEQ ID NO: 34), MGWINPSGGLAN-YAQKFQG (HCDR2; SEQ ID NO: 54), SEITTDFDY (HCDR3; SEQ ID NO: 55), [Clone 08G07]; or (h) the amino acid sequences RASQSVDSYANSYLH (LCDR1; SEQ ID NO: 51), RGSTRES (LCDR2; SEQ ID NO: 38), QQSKSEPLT (LCDR3; SEQ ID NO: 39), GYIFT-SYTMH (HCDR1; SEQ ID NO: 48), MGWIKPNNG-SASYAQKFQG (HCDR2; SEQ ID NO: 86), SEITTDFDY (HCDR3; SEQ ID NO: 55), [Clone 04E10]; or (i) the amino acid sequences RASQSVDSYANSYLH (LCDR1; SEQ ID NO: 51), RGSTRET (LCDR2; SEQ ID NO: 56), QQSKSDPLT (LCDR3; SEQ ID NO: 76), GYIFTAYSMH (HCDR1; SEQ ID NO: 83), MGWIKPNNGSTNYAQKFQG (HCDR2; SEQ ID NO: 87), TEITTEFDY (HCDR3; SEQ ID NO: 88), [Clone 08G12]; or (j) the amino acid sequences RASQSVSSYANSYLH (LCDR1; SEQ ID NO: 37), RGSTRES (LCDR2; SEQ ID NO: 38), QQSKSEPLT (LCDR3; SEQ ID NO: 39), GYTFTSYTMH (HCDR1; SEQ ID NO: 34), MGWINPNGGSTSYAQKFQG (HCDR2; SEQ ID NO: 42), QEITTEFDY (HCDR3; SEQ ID NO: 36), [Clone MH1]; or (k) the amino acid sequences RASQSVSSYAQSYLH (LCDR1; SEQ ID NO: 57), RGSTRET (LCDR2; SEQ ID NO: 56), QQSGSSPLT (LCDR3; SEQ ID NO: 89), GYTFTSYTMH (HCDR1; SEQ ID NO: 34), MGWINPNGGSTSYAQKFQG (HCDR2; SEQ ID NO: 42), QEITTEFDY (HCDR3; SEQ ID NO: 36), [Clone MH2]; or (l) the amino acid sequences RASQSVSSYAQSYLH (LCDR1; SEQ ID NO: 57), RGSTRET (LCDR2; SEQ ID NO: 56), QQYGSSPLT (LCDR3; SEQ ID NO: 90), GYTFTSYTMH (HCDR1; SEQ ID NO: 34), MGWINPNGGSTSYAQKFQG (HCDR2; SEQ ID NO: 42), QEITTEFDY (HCDR3; SEQ ID NO: 36), [Clone MH3]; or (m) the amino acid sequences RASQSVSSYANSYLH (LCDR1; SEQ ID NO: 37), RGSTRES (LCDR2; SEQ ID NO: 38), QQSKSEPLT (LCDR3; SEQ ID NO: 39), GYTFTSYTMH (HCDR1; SEQ ID NO: 34), MGWINPSGGSTSYAQKFQG (HCDR2; SEQ ID NO: 40), QEITTEFDY (HCDR3; SEQ ID NO: 36), [Clone MH4]; or (n) the amino acid sequences RASQSVSSYAQSYLH (LCDR1; SEQ ID NO: 57), RGSTRET (LCDR2; SEQ ID NO: 56), QQSGSSPLT (LCDR3; SEQ ID NO: 89), GYTFTSYTMH (HCDR1; SEQ ID NO: 34), MGWINPSGGSTSYAQKFQG (HCDR2; SEQ ID NO: 40), QEITTEFDY (HCDR3; SEQ ID NO: 36), [Clone MH5]; or (o) the amino acid sequences RASQSVSSYAQSYLH (LCDR1; SEQ ID NO: 57), RGSTRET (LCDR2; SEQ ID NO: 56), QQYGSSPLT (LCDR3; SEQ ID NO: 90), GYTFTSYTMH (HCDR1; SEQ ID NO: 34), MGWINPSGGSTSYAQKFQG (HCDR2; SEQ ID NO: 40), QEITTEFDY (HCDR3; SEQ ID NO: 36), [Clone MH6]; or (p) the amino acid sequences RASQSVSSYANSYLH (LCDR1; SEQ ID NO: 37), RGSTRES (LCDR2; SEQ ID NO: 38), QQSKSEPLT (LCDR3; SEQ ID NO: 39), GYTFTSYTMH (HCDR1; SEQ ID NO: 34), MGIINPSGGSTSYAQKFQG (HCDR2; SEQ ID NO: 35) QEITTEFDY (HCDR3; SEQ ID NO: 36), [Clone MH7]; or (q) the amino acid sequences RASQSVSSYAQSYLH (LCDR1; SEQ ID NO: 57), RGSTRET (LCDR2; SEQ ID NO: 56), QQSGSSPLT (LCDR3; SEQ ID NO: 89), GYTFTSYTMH (HCDR1; SEQ ID NO: 34), MGIINPSGGSTSYAQKFQG (HCDR2; SEQ ID NO: 35) QEITTEFDY (HCDR3; SEQ ID NO: 36), [Clone MH8]; or (r) the amino acid sequences RASQSVSSYAQSYLH (LCDR1; SEQ ID NO: 57), RGSTRET (LCDR2; SEQ ID NO: 56), QQYGSSPLT (LCDR3; SEQ ID NO: 90), GYTFTSYTMH (HCDR1; SEQ ID NO: 34), MGIINPSGGSTSYAQKFQG (HCDR2; SEQ ID NO: 35) QEITTEFDY (HCDR3; SEQ ID NO: 36), [Clone MH9]; or (s) the amino acid sequences RASQSVSSYANSYLH (LCDR1; SEQ ID NO: 37), RGSTRES (LCDR2; SEQ ID NO: 38), QQSKSEPLT (LCDR3; SEQ ID NO: 39), GYTFTSYAMH (HCDR1; SEQ ID NO: 41), MGWINPSGGSTSYAQKFQG (HCDR2; SEQ ID NO: 40), QEITTEFDY (HCDR3; SEQ ID NO: 36), [Clone MH10]; or (t) the amino acid sequences RASQSVSSYAQSYLH (LCDR1; SEQ ID NO: 57), RGSTRET (LCDR2; SEQ ID NO: 56), QQSGSSPLT (LCDR3; SEQ ID NO: 89), GYTFTSYAMH (HCDR1; SEQ ID NO: 41), MGWINPSGGSTSYAQKFQG (HCDR2; SEQ ID NO: 40), QEITTEFDY (HCDR3; SEQ ID NO: 36), [Clone MH11]; or (u) the amino acid sequences RASQSVSSYAQSYLH (LCDR1; SEQ ID NO: 57), RGSTRET (LCDR2; SEQ ID NO: 56), QQYGSSPLT (LCDR3; SEQ ID NO: 90), GYTFTSYAMH (HCDR1; SEQ ID NO: 41), MGWINPSGGSTSYAQKFQG (HCDR2; SEQ ID NO: 40), QEITTEFDY (HCDR3; SEQ ID NO: 36), [Clone MH12]; or (v) the amino acid sequences RASQSVSSYANSYLH (LCDR1; SEQ ID NO: 37), RGSTRET (LCDR2; SEQ ID NO: 56), QQSKSEPLT (LCDR3; SEQ ID NO: 39), GYTFTSYTMH (HCDR1; SEQ ID NO: 34), MGIINPSGGSTSYAQKFQG (HCDR2; SEQ ID NO: 35) QEITTEFDY (HCDR3; SEQ ID NO: 36), [Clone MH7-1]; or (w) the amino acid sequences RASQSVSSYANSYLH (LCDR1; SEQ ID NO: 37), RGSTRET (LCDR2; SEQ ID NO: 56), QQSKESPLT (LCDR3; SEQ ID NO: 47), GYTFTSYTMH (HCDR1; SEQ ID NO: 34), MGIINPSGGSTSYAQKFQG (HCDR2; SEQ ID NO: 35) QEITTEFDY (HCDR3; SEQ ID NO: 36), [Clone MH7-2]; or (x) the amino acid sequences RASQSVSSYAQSYLH (LCDR1; SEQ ID NO: 57), RGSTRET (LCDR2; SEQ ID NO: 56), QQSKESPLT (LCDR3; SEQ ID NO: 47), GYTFTSYTMH (HCDR1; SEQ ID NO: 34), MGIINPSGGSTSYAQKFQG (HCDR2; SEQ ID NO: 35) QEITTEFDY (HCDR3; SEQ ID NO: 36), [Clone MH7-3].

In some aspects, disclosed herein is an anti-C-MET antibody or an antigen-binding portion thereof, wherein the antibody comprises a heavy chain variable (VH) region and a light chain variable (VL) region, wherein In some aspects, the invention provides an anti-C-MET antibody or an antigen-binding portion thereof, wherein the antibody comprises a heavy chain variable (VH) region and a light chain variable (VL) region, wherein (a) the VH region amino acid sequence comprises HCDR1 of GYTFTSYTMH (SEQ ID NO: 34), HCDR2 of MGIINPSGGSTSYAQKFQG (SEQ ID NO: 35) and HCDR3 of QEITTEFDY (SEQ ID NO: 36); and the VL region amino acid sequence comprises LCDR1 of RASQSVSSYAQSYLH (SEQ ID NO: 57), LCDR2 of RGSTRET (SEQ ID NO: 56) and LCDR3 of QQSKESPLT (SEQ ID NO: 47);

(b) the VH region amino acid sequence comprises HCDR1 of GYTFTSYTMH (SEQ ID NO: 34), HCDR2 of MGIINPSGGSTSYAQKFQG (SEQ ID NO: 35) and HCDR3 of QEITTEFDY (SEQ ID NO: 36); and the VL region amino acid sequence comprises LCDR1 of RASQSVSSYANSYLH (SEQ ID NO: 37), LCDR2 of RGSTRET (SEQ ID NO: 56) and LCDR3 of QQSKESPLT (SEQ ID NO: 47);

(c) the VH region amino acid sequence comprises HCDR1 of GYTFTSYTMH (SEQ ID NO: 34), HCDR2 of MGIINPSGGSTSYAQKFQG (SEQ ID NO: 35) and HCDR3 of QEITTEFDY (SEQ ID NO: 36); and the VL region amino acid sequence comprises LCDR1 of RASQSVSSYANSYLH (SEQ ID NO: 37), LCDR2 of RGSTRET (SEQ ID NO: 56) and LCDR3 of QQSKSEPLT (SEQ ID NO: 39);

(d) the VH region amino acid sequence comprises HCDR1 of GYTFTSYTMH (SEQ ID NO: 34), HCDR2 of MGIINPSGGSTSYAQKFQG (SEQ ID NO: 35) and HCDR3 of QEITTEFDY (SEQ ID NO: 36); and the VL region amino acid sequence comprises LCDR1 of RASQSVSSYANSYLH (SEQ ID NO: 37), LCDR2 of RGSTRES (SEQ ID NO: 38) and LCDR3 of QQSKSEPLT (SEQ ID NO: 39);

(e) the VH region amino acid sequence comprises HCDR1 of GYTFTSYTMH (SEQ ID NO: 34), HCDR2 of MGWINPSGGLANYAQKFQG (SEQ ID NO: 54) and HCDR3 of SEITTDFDY (SEQ ID NO: 55); and the VL region amino acid sequence comprises LCDR1 of RASQSVDSYANSYLH (SEQ ID NO: 51), LCDR2 of RGSTRES (LCDR2; SEQ ID NO: 38) and LCDR3 of QQSKSEPLT (SEQ ID NO: 39);

(f) the VH region amino acid sequence comprises HCDR1 of GYTFTSYTMH (SEQ ID NO: 34), HCDR2 of MGWINPSGGSTSYAQKFQG (SEQ ID NO: 40) and HCDR3 of QEITTEFDY (SEQ ID NO: 36); and the VL region amino acid sequence comprises LCDR1 of RASQSVSSYANSYLH (SEQ ID NO: 37), LCDR2 of RGSTRES (SEQ ID NO: 38) and LCDR3 of QQSKSEPLT (SEQ ID NO: 39);

(g) the VH region amino acid sequence comprises HCDR1 of GYTFTSYAMH (SEQ ID NO: 41), HCDR2 of MGWINPSGGSTSYAQKFQG (SEQ ID NO: 40) and HCDR3 of QEITTEFDY (SEQ ID NO: 36); and the VL region amino acid sequence comprises LCDR1 of RASQSVSSYANSYLH (SEQ ID NO: 37), LCDR2 of RGSTRES (SEQ ID NO: 38) and LCDR3 of QQSKSEPLT (SEQ ID NO: 39);

(h) the VH region amino acid sequence comprises HCDR1 of GYTFTSYTMH (SEQ ID NO: 34), HCDR2 of MGWINPNGGSTSYAQKFQG (SEQ ID NO: 42) and HCDR3 of QEITTEFDY (SEQ ID NO: 36); and the VL region amino acid sequence comprises LCDR1 of RASQSVSSYANSYLH (SEQ ID NO: 37), LCDR2 of RGSTRES (SEQ ID NO: 38) and LCDR3 of QQSKSEPLT (SEQ ID NO: 39);

(i) the VH region amino acid sequence comprises HCDR1 of GYIFTSYSMH (SEQ ID NO: 43), HCDR2 of MGWINPSNGLANYAQKFQG (SEQ ID NO: 44) and HCDR3 of QEITTEFDI (SEQ ID NO: 45); and the VL region amino acid sequence comprises LCDR1 of RASQSVESYAQSYLH (SEQ ID NO: 46), LCDR2 of RGSTRES (SEQ ID NO: 38) and LCDR3 of QQSKSDPLT (SEQ ID NO: 76);

(j) the VH region amino acid sequence comprises HCDR1 of GYIFTSYTMH (SEQ ID NO: 48), HCDR2 of MGWINPNGGLASYAQKFQG (SEQ ID NO: 49) and HCDR3 of SEITTEQDY (SEQ ID NO: 50); and the VL region amino acid sequence comprises LCDR1 of RASQSVDSYANSYLH (SEQ ID NO: 51), LCDR2 of RGSTRES (SEQ ID NO: 38) and LCDR3 of QQSKESPLT (SEQ ID NO: 47); or (k) the VH region amino acid sequence comprises HCDR1 of GYIFTSYTMH (SEQ ID NO: 48), HCDR2 of MGWINPNGGSTSYAQKFQG (SEQ ID NO: 42) and HCDR3 of QEITTEFDY (SEQ ID NO: 36); and the VL region amino acid sequence comprises LCDR1 of RASQSVESYANSYLH (SEQ ID NO: 52)

In some aspects, disclosed herein is an anti-C-MET antibody or an antigen-binding portion thereof, wherein the antibody comprises a heavy chain variable (VH) region and a light chain variable (VL) region, wherein the VH region comprises any one of the VH region amino acid sequences in Table 10 and the VL region comprises any one of the VL region amino acid sequences in Table 10.

In some aspects, disclosed herein is an anti-C-MET antibody or an antigen-binding portion thereof, wherein the antibody comprises a heavy chain variable (VH) region and a light chain variable (VL) region, wherein (a) the VH region amino acid sequence comprises SEQ ID NO:1 and the VL region amino acid sequence comprises SEQ ID NO:2;

(b) the VH region amino acid sequence comprises SEQ ID NO:3 and the VL region amino acid sequence comprises SEQ ID NO:4;

(c) the VH region amino acid sequence comprises SEQ ID NO:5 and the VL region amino acid sequence comprises SEQ ID NO:6;

(d) the VH region amino acid sequence comprises SEQ ID NO:7 and the VL region amino acid sequence comprises SEQ ID NO:8; or (e) the VH region amino acid sequence comprises SEQ ID NO:9 and the VL region amino acid sequence comprises SEQ ID NO:10.

In some aspects, disclosed herein is an anti-C-MET antibody or an antigen-binding portion thereof, wherein the antibody comprises a heavy chain variable (VH) region and a light chain variable (VL) region, wherein (a) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:1 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:2;

(b) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:3 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:4;

(c) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:5 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:6;

(d) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:7 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:8; or (e) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:9 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:10.

In some aspects, the antibody or antigen-binding portion as defined herein may be isolated.

The antibody molecule or antigen-binding portion as defined herein may cross-compete for binding to C-MET with an antibody or antigen-binding portion thereof comprising the sets of CDRs disclosed herein. In some embodiments, the invention provides an isolated anti-C-MET antibody or an antigen-binding portion thereof, wherein the antibody or antigen-binding portion cross-competes for binding to C-MET with the antibody or antigen-binding portion comprising the sets of CDRs disclosed herein; and (a) comprises fully germline human framework amino acid sequences; (b) does not comprise a 'DS' isomerisation site in the LCDR1, (c) does not comprise a 'NS' deamidation site in the LCDR1, (d) does not comprise an exposed 'F' side chain in the LCDR1 that constitutes and oxidation risk, (e) does not comprise a 'NG' deamidation site in the HCDR2, (e) does not comprise a 'NN' deamidation site in the HCDR2, (f) does not comprise an exposed 'W' side chain in the HCDR2 that constitutes and oxidation risk, and/or (g) does not comprise a 'DP' acid hydrolysis site in the LCDR3; and/or (h) does not comprise a human T cell epitope sequence in the LCDR2; and/or (i) does not comprise a human T cell epitope sequence in the LCDR3; and/or (j) exhibits a higher isoelectric point in comparison to the isoelectric point of antibody h224G11; and/or (k) exhibits an isoelectric point of 8.0 or above as measured by isoelectric focusing, when in human IgG4(S228P) format. The amino acid sequences of antibody h224G11 may be found in Table 2.

The terms "cross-compete", "cross-competition", "cross-block", "cross-blocked" and "cross-blocking" are used interchangeably herein to mean the ability of an antibody or portion thereof to interfere with the binding directly or indirectly through allosteric modulation of the anti-C-MET antibodies of the invention to the target C-MET (e.g., human C-MET). The extent to which an antibody or portion thereof is able to interfere with the binding of another to the target, and therefore whether it can be said to cross-block or cross-compete according to the invention, can be determined using competition binding assays. One example of a binding competition assay is Homogeneous Time Resolved Fluorescence (HTRF). One particularly suitable quantitative cross-competition assay uses a FACS- or an AlphaScreen-based approach to measure competition between the labelled (e.g. His tagged, biotinylated or radioactive labelled) antibody or portion thereof and the other antibody or portion thereof in terms of their binding to the target. In general, a cross-competing antibody or portion thereof is, for example, one which will bind to the target in the cross-competition assay such that, during the assay and in the presence of a second antibody or portion thereof, the recorded displacement of the immunoglobulin single variable domain or polypeptide according to the invention is up to 100% (e.g. in a FACS based competition assay) of the maximum theoretical displacement (e.g. displacement by cold (e.g. unlabeled) antibody or fragment thereof that needs to be cross-blocked) by the potentially cross-blocking antibody or fragment thereof that is present in a given amount. Preferably, cross-competing antibodies or portions thereof have a recorded displacement that is between 10% and 100%, or between 50% and 100%.

The antibody molecule or antigen-binding portion as defined herein may be thermally stable. In some cases, an antibody molecule or antigen-binding portion may have substantially the same thermal stability as murine anti-C-MET antibody 224G11 or h224G11. In some cases, an antibody molecule or antigen-binding portion may be more thermally stable than murine anti-C-MET antibody 224G11 or h224G11. In some examples, an antibody molecule or antigen-binding portion may have a melting temperature (Tm) from about 77° C. to about 81° C. and may be in a human IgG4 format. In some aspects, an antibody molecule or antigen-binding portion may have a Tm from about 77.2° C. to about 80.6° C. and may be in a human IgG4 format. In some cases, an antigen-binding portion is a Fab. The melting temperature of an antibody molecule or antigen-binding portion thereof may be analysed by a differential scanning calorimetry (DSC) assay.

In some examples, the antibody molecule or antigen-binding portion as defined herein may have a higher isoelectric point (pI) than murine anti-C-MET antibody 224G11 or h224G11.

In some cases, the antibody molecule or antigen-binding portion thereof may have a pI greater than about pH 7.3 or greater than about pH 7.4. For example, the antibody molecule or antigen-binding portion thereof may have a pI from about pH 7.3 to about pH 8.5. The isoelectric point of an antibody molecule or antigen-binding portion thereof may be analysed by a protein charge variant assay.

The antibody molecule or antigen-binding portion as defined herein may comprise one or more substitutions, deletions and/or insertions which remove a post-translational modification (PTM) site, for example a glycosylation site (N-linked or O-linked), a deamination site, a phosphorylation site or an isomerisation/fragmentation site.

More than 350 types of PTM are known. Key forms of PTM include phosphorylation, glycosylation (N- and O-linked), sumoylation, palmitoylation, acetylation, sulfation, myristoylation, prenylation and methylation (of K and R residues). Statistical methods to identify putative amino acid sites responsible for specific PTMs are well known in the art (see Zhou et al., 2016, Nature Protocols 1: 1318-1321). Removal of such a site for example by substitution, deletion and/or insertion and then optionally testing (experimentally and/or theoretically) for (a) binding activity and/or (b) loss of the PTM is contemplated.

For example, the 224G11 murine LCDR3 (as defined herein, i.e. the amino acid sequence QQSKEDPLT (SEQ ID NO: 33)) has been identified to have a putative acid hydrolysis site at residues 6 and 7 (DP). Removal this site at equivalent positions in an LCDR3 of the invention, for example by substitution of D (such as to S, or E), is envisaged (as for example in clone MH7 and others found in Tables 3 and 4).

In a further example, the 224G11 murine LCDR1 (as defined herein, i.e. the amino acid sequence KSSESVDSY-ANSFLH (SEQ ID NO: 31)) has been identified to have a putative isomerisation site at residue 7 (D). Removal this site at equivalent positions in an LCDR1 of the invention, for example by substitution of D (such as to S, or E), is envisaged (as for example in clone MH7 and others found in Tables 3 and 4).

In a further example, the 224G11 murine LCDR1 (as defined herein, i.e. the amino acid sequence KSSESVDSY-ANSFLH (SEQ ID NO: 31)) has been identified to have a putative deamidation site at residue 11 (N). Removal this site at equivalent positions in an LCDR1 of the invention, for example by substitution of N (such as to Q), is envisaged (as for example in clone 04F09 and others found in Tables 3 and 4).

In a further example, the 224G11 murine LCDR1 (as defined herein, i.e. the amino acid sequence KSSESVDSY-ANSFLH (SEQ ID NO: 31)) has been identified to have a putative oxidation site at residue 13 (F), which is in a known solvent-exposed region of the CDR loop. Removal this site at equivalent positions in an LCDR1 of the invention, for example by substitution of F (such as to Y), is envisaged (as for example in clone MH7 and others found in Tables 3 and 4).

In a further example, the 224G11 murine HCDR2 (as defined herein, i.e. the amino acid sequence MGWIKPNNGLANYAQKFQG (SEQ ID NO: 26)) has been identified to have a putative oxidation site at residue 3 (W), which is in a known solvent-exposed region of the CDR loop. Removal this site at equivalent positions in an HCDR2 of the invention, for example by substitution of W (such as to I), is envisaged (as for example in clone MH7 and others found in Tables 3 and 4).

In a further example, the 224G11 murine HCDR2 (as defined herein, i.e. the amino acid sequence MGWIKPNNGLANYAQKFQG (SEQ ID NO: 26)) has been identified to have a putative deamidation site at residue 7 (N), which is in a known solvent-exposed region of the CDR loop. Removal this site at equivalent positions in an HCDR2 of the invention, for example by substitution of N (such as to S), is envisaged (as for example in clone MH7 and others found in Tables 3 and 4).

In a further example, the 224G11 murine HCDR2 (as defined herein, i.e. the amino acid sequence MGWIKPNNGLANYAQKFQG (SEQ ID NO: 26)) has been identified to have a putative deamidation site at residue 8 (N), which is in a known solvent-exposed region of the CDR loop. Removal this site at equivalent positions in an HCDR2 of the invention, for example by substitution of N (such as to G), is envisaged (as for example in clone MH7 and others found in Tables 3 and 4).

The antibody molecule or antigen-binding portion thereof may be human, humanized or chimeric.

The antibody molecule or antigen-binding portion thereof may comprise one or more human variable domain framework scaffolds into which the CDRs have been inserted. For example, the VH region, the VL region, or both the VH and the VL region may comprise one or more human framework region amino acid sequences.

The antibody molecule or antigen-binding portion thereof may comprise an IGHV1-46 human germline scaffold into which the corresponding HCDR sequences have been inserted. The antibody molecule or antigen-binding portion thereof may comprise a VH region that comprises an IGHV1-46 human germline scaffold amino acid sequence into which a set of corresponding HCDR1, HCDR2 and HCDR3 amino acid sequences have been inserted.

The antibody molecule or antigen-binding portion thereof may comprise an IGKV3-20 human germline scaffold into which the corresponding LCDR sequences have been inserted. The antibody molecule or antigen-binding portion thereof may comprise a VL region that comprises an IGKV3-20 human germline scaffold amino acid sequence into which a set of corresponding LCDR1, LCDR2 and LCDR3 amino acid sequences have been inserted.

The antibody molecule or antigen-binding portion thereof may comprise an IGHV1-46 human germline scaffold into which the corresponding HCDR sequences have been inserted and an IGKV3-20 human germline scaffold into which the corresponding LCDR sequences have been inserted. The antibody molecule or antigen-binding portion thereof may comprise a VH region that comprises an IGHV1-46 human germline scaffold amino acid sequence into which a set of corresponding HCDR1, HCDR2 and HCDR3 amino acid sequences have been inserted and a VL region that comprises an IGKV3-20 human germline scaffold amino acid sequence into which a set of corresponding LCDR1, LCDR2 and LCDR3 amino acid sequences have been inserted. The HCDR1, HCDR2, HCDR3, LCDR1, LCDR2 and LCDR3 amino acid sequences may be the HCDR1, HCDR2, HCDR3, LCDR1, LCDR2 and LCDR3 amino acid sequences of any one of the clones in Table 4 or 8 (with all six CDR sequences being from the same clone).

In some aspects, the antibody molecule or antigen-binding portion thereof may comprise an immunoglobulin constant region. In some embodiments, the immunoglobulin constant region is IgG1, IgG2, IgG3, IgG4, IgA1 or IgA2. In additional embodiments, the immunoglobulin constant region is IgG1, IgG2, IgG3, IgG4(S228P), IgA1 or IgA2. The antibody molecule or antigen-binding portion thereof may comprise an immunologically inert constant region. In some aspects, an anti-C-MET antibody or antigen-binding portion thereof may comprise an immunoglobulin constant region comprising a wild-type human IgG1 constant region, a human IgG1 constant region comprising the amino acid substitutions L234A, L235A and G237A or a human IgG1 constant region comprising the amino acid substitutions L234A, L235A, G237A and P331S. In some aspects, an anti-C-MET antibody or antigen-binding portion thereof may comprise an immunoglobulin constant region comprising a wild-type human IgG2 constant region or a wild-type human IgG4 constant region. In some aspects, an anti-C-MET antibody may comprise an immunoglobulin constant region comprising any one of the amino acid sequences in Table 11. The Fc region sequences in Table 11 begin at the CH1 domain. In some aspects, an anti-C-MET antibody may comprise an immunoglobulin constant region comprising an amino acid sequence of an Fc region of human IgG4, human IgG4(S228P), human IgG2, human IgG1, human IgG1-3M or human IgG1-4M. For example, the human IgG4(S228P) Fc region comprises the following substitution compared to the wild-type human IgG4 Fc region: S228P. For example, the human IgG1-3M Fc region comprises the following substitutions compared to the wild-type human IgG1 Fc region: L234A, L235A and G237A, while the human IgG1-4M Fc region comprises the following substitutions compared to the wild-type human IgG1 Fc region: L234A, L235A, G237A and P331S. In some aspects, a position of an amino acid residue in a constant region of an immunoglobulin molecule is numbered according to EU nomenclature (Ward et al., 1995 *Therap. Immunol.* 2:77-94). In some aspects, an immunoglobulin constant region may comprise an RDELT (SEQ ID NO:20) motif or an REEM (SEQ ID NO:21) motif (underlined in Table 11). The REEM (SEQ ID NO:21) allotype is found in a smaller human population than the RDELT (SEQ ID NO:20) allotype. In some aspects, an anti-C-MET antibody may comprise an immunoglobulin constant region comprising any one of SEQ ID NOS:11-17. In some aspects, an anti-C-MET antibody may comprise the six CDR amino acid sequences of any one of the clones in Table 4 or 8 and any one of the Fc region amino acid sequences in Table 11. In some aspects, an anti-C-MET antibody may comprise an immunoglobulin heavy chain constant region comprising any one of the Fc region amino acid sequences in Table 11 and an immunoglobulin light chain constant region that is a kappa light chain constant region or a lambda light chain constant region.

In some aspects, disclosed herein is an anti-C-MET antibody or an antigen-binding portion thereof, wherein the antibody comprises a heavy chain variable (VH) region, a light chain variable (VL) region and a heavy chain constant region, wherein (a) the VH region amino acid sequence comprises HCDR1 of GYTFTSYTMH (SEQ ID NO: 34), HCDR2 of MGIINPSGGSTSYAQKFQG (SEQ ID NO: 35) and HCDR3 of QEITTEFDY (SEQ ID NO: 36); the VL region amino acid sequence comprises LCDR1 of RASQSVSSYAQSYLH (SEQ ID NO: 57), LCDR2 of RGSTRET (SEQ ID NO: 56) and LCDR3 of QQSKESPLT (SEQ ID NO: 47); and the heavy chain constant region comprises any one of SEQ ID NOS:11-17;

(b) the VH region amino acid sequence comprises HCDR1 of GYTFTSYTMH (SEQ ID NO: 34), HCDR2 of MGIINPSGGSTSYAQKFQG (SEQ ID NO: 35) and HCDR3 of QEITTEFDY (SEQ ID NO: 36); the VL region amino acid sequence comprises LCDR1 of RASQSVSSYANSYLH (SEQ ID NO: 37), LCDR2 of RGSTRET (SEQ ID NO: 56) and LCDR3 of QQSKESPLT (SEQ ID NO: 47); and the heavy chain constant region comprises any one of SEQ ID NOS:11-17;

(c) the VH region amino acid sequence comprises HCDR1 of GYTFTSYTMH (SEQ ID NO: 34), HCDR2 of MGIINPSGGSTSYAQKFQG (SEQ ID NO: 35) and HCDR3 of QEITTEFDY (SEQ ID NO: 36); the VL region amino acid sequence comprises LCDR1 of RASQSVSSYANSYLH (SEQ ID NO: 37), LCDR2 of RGSTRET (SEQ ID NO: 56) and LCDR3 of QQSKESPLT (SEQ ID NO: 39); and the heavy chain constant region comprises any one of SEQ ID NOS:11-17;

(d) the VH region amino acid sequence comprises HCDR1 of GYTFTSYTMH (SEQ ID NO: 34), HCDR2 of MGIINPSGGSTSYAQKFQG (SEQ ID NO: 35) and HCDR3 of QEITTEFDY (SEQ ID NO: 36); the VL region amino acid sequence comprises LCDR1 of RASQSVSSYANSYLH (SEQ ID NO: 37), LCDR2 of RGSTRES (SEQ ID NO: 38) and LCDR3 of QQSKESPLT (SEQ ID NO: 39); and the heavy chain constant region comprises any one of SEQ ID NOS: 11-17;

(e) the VH region amino acid sequence comprises HCDR1 of GYTFTSYTMH (SEQ ID NO: 34), HCDR2 of MGWINPSGGLANYAQKFQG (SEQ ID NO: 54) and HCDR3 of SEITTDFDY (SEQ ID NO: 55); the VL region amino acid sequence comprises LCDR1 of RASQSVDSYANSYLH (SEQ ID NO: 51), LCDR2 of RGSTRES (LCDR2; SEQ ID NO: 38) and LCDR3 of QQSKESPLT (SEQ ID NO: 39); and the heavy chain constant region comprises any one of SEQ ID NOS:11-17;

(f) the VH region amino acid sequence comprises HCDR1 of GYTFTSYTMH (SEQ ID NO: 34), HCDR2 of MGWINPSGGSTSYAQKFQG (SEQ ID NO: 40) and HCDR3 of QEITTEFDY (SEQ ID NO: 36); the VL region amino acid sequence comprises LCDR1 of RASQSVSSYANSYLH (SEQ ID NO: 37), LCDR2 of RGSTRES (SEQ ID NO: 38) and LCDR3 of QQSKESPLT (SEQ ID NO: 39); and the heavy chain constant region comprises any one of SEQ ID NOS:11-17;

(g) the VH region amino acid sequence comprises HCDR1 of GYTFTSYAMH (SEQ ID NO: 41), HCDR2 of MGWINPSGGSTSYAQKFQG (SEQ ID NO: 40) and HCDR3 of QEITTEFDY (SEQ ID NO: 36); the VL region amino acid sequence comprises LCDR1 of RASQSVSSYANSYLH (SEQ ID NO: 37), LCDR2 of RGSTRES (SEQ ID NO: 38) and LCDR3 of QQSKSEPLT (SEQ ID NO: 39); and the heavy chain constant region comprises any one of SEQ ID NOS: 11-17;

(h) the VH region amino acid sequence comprises HCDR1 of GYTFTSYTMH (SEQ ID NO: 34), HCDR2 of MGWINPNGGSTSYAQKFQG (SEQ ID NO: 42) and HCDR3 of QEITTEFDY (SEQ ID NO: 36); the VL region amino acid sequence comprises LCDR1 of RASQSVSSYANSYLH (SEQ ID NO: 37), LCDR2 of RGSTRES (SEQ ID NO: 38) and LCDR3 of QQSKSEPLT (SEQ ID NO: 39); and the heavy chain constant region comprises any one of SEQ ID NOS: 11-17;

(i) the VH region amino acid sequence comprises HCDR1 of GYIFTSYSMH (SEQ ID NO: 43), HCDR2 of MGWINPSNGLANYAQKFQG (SEQ ID NO: 44) and HCDR3 of QEITTEFDI (SEQ ID NO: 45); the VL region amino acid sequence comprises LCDR1 of RASQSVESYAQSYLH (SEQ ID NO: 46), LCDR2 of RGSTRES (SEQ ID NO: 38) and LCDR3 of QQSKSDPLT (SEQ ID NO: 76); and the heavy chain constant region comprises any one of SEQ ID NOS: 11-17;

(j) the VH region amino acid sequence comprises HCDR1 of GYIFTSYTMH (SEQ ID NO: 48), HCDR2 of MGWINPNGGLASYAQKFQG (SEQ ID NO: 49) and HCDR3 of SEITTEQDY (SEQ ID NO: 50); the VL region amino acid sequence comprises LCDR1 of RASQSVDSYANSYLH (SEQ ID NO: 51), LCDR2 of RGSTRES (SEQ ID NO: 38) and LCDR3 of QQSKESPLT (SEQ ID NO: 47); and the heavy chain constant region comprises any one of SEQ ID NOS: 11-17; or (k) the VH region amino acid sequence comprises HCDR1 of GYIFTSYTMH (SEQ ID NO: 48), HCDR2 of MGWINPNGGSTSYAQKFQG (SEQ ID NO: 42) and HCDR3 of QEITTEFDY (SEQ ID NO: 36); the VL region amino acid sequence comprises LCDR1 of RASQSVESYANSYLH (SEQ ID NO: 52), LCDR2 of RGSTRES (SEQ ID NO: 38) and LCDR3 of QQYGSEPLT (SEQ ID NO: 53); and the heavy chain constant region comprises any one of SEQ ID NOS: 11-17.

In some aspects, disclosed herein is an anti-C-MET antibody or an antigen-binding portion thereof, wherein the antibody comprises a heavy chain variable (VH) region, a light chain variable (VL) region and a heavy chain constant region, wherein (a) the VH region amino acid sequence comprises or consists of SEQ ID NO:1; the VL region amino acid sequence comprises or consists of SEQ ID NO:2; and the heavy chain constant region comprises a wild-type human IgG4 constant region, a human IgG4 constant region comprising the amino acid substitution S228P, a wild-type human IgG2 constant region; a wild-type human IgG1 constant region or a human IgG1 constant region comprising the amino acid substitutions L234A, L235A and G237A;

(b) the VH region amino acid sequence comprises or consists of SEQ ID NO:3; the VL region amino acid sequence comprises or consists of SEQ ID NO:4; and the heavy chain constant region comprises a wild-type human IgG4 constant region, a human IgG4 constant region comprising the amino acid substitution S228P, a wild-type human IgG2 constant region; a wild-type human IgG1 constant region or a human IgG1 constant region comprising the amino acid substitutions L234A, L235A and G237A;
(c) the VH region amino acid sequence comprises or consists of SEQ ID NO:5; the VL region amino acid sequence comprises or consists of SEQ ID NO:6; and the heavy chain constant region comprises a wild-type human IgG4 constant region, a human IgG4 constant region comprising the amino acid substitution S228P, a wild-type human IgG2 constant region; a wild-type human IgG1 constant region or a human IgG1 constant region comprising the amino acid substitutions L234A, L235A and G237A;
(d) the VH region amino acid sequence comprises or consists of SEQ ID NO:7; the VL region amino acid sequence comprises or consists of SEQ ID NO:8; and the heavy chain constant region comprises a wild-type human IgG4 constant region, a human IgG4 constant region comprising the amino acid substitution S228P, a wild-type human IgG2 constant region; a wild-type human IgG1 constant region or a human IgG1 constant region comprising the amino acid substitutions L234A, L235A and G237A; or
(e) the VH region amino acid sequence comprises or consists of SEQ ID NO:9; the VL region amino acid sequence comprises or consists of SEQ ID NO:10; and the heavy chain constant region comprises a wild-type human IgG4 constant region, a human IgG4 constant region comprising the amino acid substitution S228P, a wild-type human IgG2 constant region; a wild-type human IgG1 constant region or a human IgG1 constant region comprising the amino acid substitutions L234A, L235A and G237A.

In some aspects, disclosed herein is an anti-C-MET antibody or an antigen-binding portion thereof, wherein the antibody comprises a heavy chain variable (VH) region, a light chain variable (VL) region and a heavy chain constant region, wherein
(a) the VH region amino acid sequence comprises or consists of SEQ ID NO:1; the VL region amino acid sequence comprises or consists of SEQ ID NO:2; and the heavy chain constant region comprises any one of SEQ ID NOS:11-17;
(b) the VH region amino acid sequence comprises or consists of SEQ ID NO:3; the VL region amino acid sequence comprises or consists of SEQ ID NO:4; and the heavy chain constant region comprises any one of SEQ ID NOS:11-17;
(c) the VH region amino acid sequence comprises or consists of SEQ ID NO:5; the VL region amino acid sequence comprises or consists of SEQ ID NO:6; and the heavy chain constant region comprises any one of SEQ ID NOS:11-17;
(d) the VH region amino acid sequence comprises or consists of SEQ ID NO:7; the VL region amino acid sequence comprises or consists of SEQ ID NO:8; and the heavy chain constant region comprises any one of SEQ ID NOS:11-17; or
(e) the VH region amino acid sequence comprises or consists of SEQ ID NO:9; the VL region amino acid sequence comprises or consists of SEQ ID NO:10; and the heavy chain constant region comprises any one of SEQ ID NOS:11-17.

The antibody molecule or antigen-binding portion thereof may be a Fab fragment, a F(ab)$_2$ fragment, an Fv fragment, a tetrameric antibody, a tetravalent antibody, a multispecific antibody (for example, a bispecific antibody), a domain-specific antibody, a single domain antibody, a monoclonal antibody or a fusion protein. In one embodiment, an antibody may be a bispecific antibody that binds specifically to a first antigen and a second antigen, wherein the first antigen is C-MET and the second antigen is not C-MET. Antibody molecules and methods for their construction and use are described, in for example Holliger & Hudson (2005, Nature Biotechnol. 23(9): 1126-1136).

In another aspect of the invention, there is provided an immunoconjugate comprising the antibody molecule or antigen-binding portion thereof of the invention as defined herein linked to a therapeutic agent.

Examples of suitable therapeutic agents include cytotoxins, radioisotopes, chemotherapeutic agents, immunomodulatory agents, anti-angiogenic agents, antiproliferative agents, pro-apoptotic agents, and cytostatic and cytolytic enzymes (for example RNAses). Further therapeutic agents include a therapeutic nucleic acid, such as a gene encoding an immunomodulatory agent, an anti-angiogenic agent, an anti-proliferative agent, or a pro-apoptotic agent. These drug descriptors are not mutually exclusive, and thus a therapeutic agent may be described using one or more of the above terms.

Examples of suitable therapeutic agents for use in immunoconjugates include the taxanes, maytansines, CC-1065 and the duocarmycins, the calicheamicins and other enediynes, and the auristatins. Other examples include the anti-folates, vinca alkaloids, and the anthracyclines. Plant toxins, other bioactive proteins, enzymes (i.e., ADEPT), radioisotopes, photosensitizers may also be used in immunoconjugates. In addition, conjugates can be made using secondary carriers as the cytotoxic agent, such as liposomes or polymers, Suitable cytotoxins include an agent that inhibits or prevents the function of cells and/or results in destruction of cells. Representative cytotoxins include antibiotics, inhibitors of tubulin polymerization, alkylating agents that bind to and disrupt DNA, and agents that disrupt protein synthesis or the function of essential cellular proteins such as protein kinases, phosphatases, topoisomerases, enzymes, and cyclins.

Representative cytotoxins include, but are not limited to, doxorubicin, daunorubicin, idarubicin, aclarubicin, zorubicin, mitoxantrone, epirubicin, carubicin, nogalamycin, menogaril, pitarubicin, valrubicin, cytarabine, gemcitabine, trifluridine, ancitabine, enocitabine, azacitidine, doxifluhdine, pentostatin, broxuhdine, capecitabine, cladhbine, decitabine, floxuhdine, fludarabine, gougerotin, puromycin, tegafur, tiazofuhn, adhamycin, cisplatin, carboplatin, cyclophosphamide, dacarbazine, vinblastine, vincristine, mitoxantrone, bleomycin, mechlorethamine, prednisone, procarbazine, methotrexate, flurouracils, etoposide, taxol, taxol analogs, platins such as cis-platin and carbo-platin, mitomycin, thiotepa, taxanes, vincristine, daunorubicin, epirubicin, actinomycin, authramycin, azaserines, bleomycins, tamoxifen, idarubicin, dolastatins/auristatins, hemiasterlins, esperamicins and maytansinoids.

Suitable immunomodulatory agents include anti-hormones that block hormone action on tumors and immunosuppressive agents that suppress cytokine production, downregulate self-antigen expression, or mask MHC antigens.

Also provided is a nucleic acid molecule encoding the antibody molecule or antigen-binding portion thereof of the invention as defined herein. A nucleic acid molecule may encode (a) the VH region amino acid sequence; (b) the VL region amino acid sequence; or (c) both the VH and the VL region amino acid sequences of an anti-C-MET antibody or an antigen-binding portion thereof described herein. In some aspects, the nucleic acid molecule as defined herein may be isolated.

Further provided is a vector comprising the nucleic acid molecule of the invention as defined herein. The vector may be an expression vector.

Also provided is a host cell comprising the nucleic acid molecule or the vector of the invention as defined herein. The host cell may be a recombinant host cell.

In a further aspect there is provided a method of producing an anti-C-MET antibody and/or an antigen-binding portion thereof, comprising culturing the host cell of the invention under conditions that result in expression and/or production of the antibody and/or the antigen-binding portion thereof, and isolating the antibody and/or the antigen-binding portion thereof from the host cell or culture.

In another aspect of the invention there is provided a pharmaceutical composition comprising the antibody molecule or antigen-binding portion thereof of the invention as defined herein, or the nucleic acid molecule of the invention as defined herein, or the vector of the invention as defined herein.

The invention also provides a method for inhibiting C-MET signalling in a cell, the method comprising contacting the cell with an anti-C-MET antibody molecule or antigen-binding portion thereof described herein. In some embodiments, an anti-C-MET antibody molecule or antigen-binding portion of the invention locks C-MET into a non-activating monomeric form.

Further provided is a method for enhancing an immune response in a subject, comprising administering to the subject an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein. In some embodiments, an anti-C-MET antibody molecule or antigen-binding portion of the invention engages a subject's immune cells via antibody effector-function mediated engagement.

In a further aspect there is provided a method for treating or preventing cancer in a subject, comprising administering to the subject an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

For example, the cancer may be Gastrointestinal Stromal cancer (GIST), pancreatic cancer, melanoma, breast cancer, lung cancer, bronchial cancer, colorectal cancer, prostate cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, or cancer of hematological tissues.

The invention also provides an antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein, for use in the treatment of cancer.

In another aspect the invention provides the antibody molecule, or antigen-binding portion thereof, or the immunoconjugate, or the nucleic acid molecule, or the vector for use, or the method of treatment of the invention as defined herein, for separate, sequential or simultaneous use in a combination combined with a second therapeutic agent, for example an anti-cancer agent.

In a further aspect there is provided the use of an antibody molecule or antigen-binding portion thereof of the invention as defined herein, or an immunoconjugate of the invention as defined herein, or a nucleic acid molecule of the invention as defined herein, or a vector of the invention as defined herein, or a pharmaceutical composition of the invention as defined herein, in the manufacture of a medicament for the treatment of cancer.

The invention also provides a method for treating or preventing an autoimmune disease or an inflammatory disease in a subject, comprising administering to the subject an effective amount of the antibody molecule or antigen-binding portion thereof as defined herein, or the immunoconjugate as defined here, or the nucleic acid molecule as defined herein, or the vector as defined herein, or the pharmaceutical composition as defined herein.

For example, the autoimmune disease or inflammatory disease may be arthritis, asthma, multiple sclerosis, psoriasis, Crohn's disease, inflammatory bowel disease, lupus, Grave's disease and Hashimoto's thyroiditis, or ankylosing spondylitis.

Also provided is an antibody molecule or antigen-binding portion thereof as defined herein, or the immunoconjugate as defined herein, or the nucleic acid molecule as defined herein, or the vector as defined herein, or the pharmaceutical composition as defined herein, for use in the treatment of an autoimmune disease or an inflammatory disease.

Further provided is the use of an antibody molecule or antigen-binding portion thereof as defined herein, or an immunoconjugate as defined herein, or a nucleic acid molecule as defined herein, or a vector as defined herein, or a pharmaceutical composition as defined herein, in the manufacture of a medicament for the treatment of an autoimmune disease or an inflammatory disease.

The invention also provides a method for treating or preventing a cardiovascular disease or a fibrotic disease in a subject, comprising administering to the subject an effective amount of the antibody molecule or antigen-binding portion thereof as defined herein, or the immunoconjugate as defined here, or the nucleic acid molecule as defined herein, or the vector as defined herein, or the pharmaceutical composition as defined herein.

Also provided is an antibody molecule or antigen-binding portion thereof as defined herein, or the immunoconjugate as defined herein, or the nucleic acid molecule as defined herein, or the vector as defined herein, or the pharmaceutical composition as defined herein, for use in the treatment of a cardiovascular disease or a fibrotic disease.

Further provided is the use of an antibody molecule or antigen-binding portion thereof as defined herein, or an immunoconjugate as defined herein, or a nucleic acid molecule as defined herein, or a vector as defined herein, or a pharmaceutical composition as defined herein, in the manufacture of a medicament for the treatment of a cardiovascular disease or a fibrotic disease.

The cardiovascular disease in any aspect of the invention may for example be coronary heart disease or atherosclerosis.

The fibrotic disease in any aspect of the invention may be, for example, myocardial infarction, angina, osteoarthritis, pulmonary fibrosis, asthma, cystic fibrosis or bronchitis.

In one embodiment, the invention provides an anti-C-MET antibody or an antigen-binding portion thereof comprising the amino acid sequences disclosed herein for use in therapy.

The pharmaceutical composition of the invention may comprise a pharmaceutically acceptable excipient, carrier or diluent. A pharmaceutically acceptable excipient may be a compound or a combination of compounds entering into a pharmaceutical composition which does not provoke secondary reactions and which allows, for example, facilitation of the administration of the anti-C-MET antibody molecule, an increase in its lifespan and/or in its efficacy in the body or an increase in its solubility in solution. These pharmaceutically acceptable vehicles are well known and will be adapted by the person skilled in the art as a function of the mode of administration of the anti-C-MET antibody molecule.

In some embodiments, the anti-C-MET antibody molecule may be provided in a lyophilised form for reconstitution prior to administration. For example, lyophilised antibody molecules may be re-constituted in sterile water and mixed with saline prior to administration to an individual.

The anti-C-MET antibody molecules will usually be administered in the form of a pharmaceutical composition, which may comprise at least one component in addition to the antibody molecule. Thus pharmaceutical compositions may comprise, in addition to the anti-C-MET antibody molecule, a pharmaceutically acceptable excipient, carrier, buffer, stabilizer or other materials well known to those skilled in the art. Such materials should be non-toxic and should not interfere with the efficacy of the anti-C-MET antibody molecule. The precise nature of the carrier or other material will depend on the route of administration, which may be by bolus, infusion, injection or any other suitable route, as discussed below.

For parenteral, for example sub-cutaneous or intra-venous administration, e.g. by injection, the pharmaceutical composition comprising the anti-C-MET antibody molecule may be in the form of a parenterally acceptable aqueous solution which is pyrogen-free and has suitable pH, isotonicity and stability. Those of relevant skill in the art are well able to prepare suitable solutions using, for example, isotonic vehicles, such as Sodium Chloride Injection, Ringe's Injection, Lactated Ringer's Injection. Preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g. Zn-protein complexes); and/or non-ionic surfactants, such as TWEEN™, PLURONICS™ or polyethylene glycol (PEG).

A pharmaceutical composition comprising an anti-C-MET antibody molecule may be administered alone or in combination with other treatments, either simultaneously or sequentially dependent upon the condition to be treated.

An anti-C-MET antibody molecule as described herein may be used in a method of treatment of the human or animal body, including prophylactic or preventative treatment (e.g. treatment before the onset of a condition in an individual to reduce the risk of the condition occurring in the individual; delay its onset; or reduce its severity after onset). The method of treatment may comprise administering the anti-C-MET antibody molecule to an individual in need thereof.

Administration is normally in a "therapeutically effective amount", this being sufficient to show benefit to a patient. Such benefit may be at least amelioration of at least one symptom. The actual amount administered, and rate and time-course of administration, will depend on the nature and severity of what is being treated, the particular mammal being treated, the clinical condition of the individual patient, the cause of the disorder, the site of delivery of the composition, the method of administration, the scheduling of administration and other factors known to medical practitioners. Prescription of treatment, e.g. decisions on dosage etc., is within the responsibility of general practitioners and other medical doctors and may depend on the severity of the symptoms and/or progression of a disease being treated. Appropriate doses of antibody molecules are well known in the art (Ledermann J. A. et al., 1991, Int. J. Cancer 47: 659-664; Bagshawe K. D. et al., 1991, Antibody, Immunoconjugates and Radiopharmaceuticals 4: 915-922). Specific dosages may be indicated herein or in the Physician's Desk Reference (2003) as appropriate for the type of medicament being administered may be used. A therapeutically effective amount or suitable dose of an antibody molecule may be determined by comparing its in vitro activity and in vivo activity in an animal model. Methods for extrapolation of effective dosages in mice and other test animals to humans are known. The precise dose will depend upon a number of factors, including whether the antibody is for prevention or for treatment, the size and location of the area to be treated, the precise nature of the antibody (e.g. whole antibody, fragment) and the nature of any detectable label or other molecule attached to the antibody.

A typical antibody dose will be in the range 100 μg to 1 g for systemic applications, and 1 μg to 1 mg for topical applications. An initial higher loading dose, followed by one or more lower doses, may be administered. Typically, the antibody will be a whole antibody, e.g. the IgG4(S228P) or IgG4 isotype. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician. The treatment schedule for an individual may be dependent on the pharmocokinetic and pharmacodynamic properties of the antibody composition, the route of administration and the nature of the condition being treated.

Treatment may be periodic, and the period between administrations may be about two weeks or more, e.g. about three weeks or more, about four weeks or more, about once a month or more, about five weeks or more, or about six weeks or more. For example, treatment may be every two to four weeks or every four to eight weeks. Treatment may be given before, and/or after surgery, and/or may be administered or applied directly at the anatomical site of surgical treatment or invasive procedure. Suitable formulations and routes of administration are described above.

In some embodiments, anti-C-MET antibody molecules as described herein may be administered as sub-cutaneous injections. Sub-cutaneous injections may be administered using an auto-injector, for example for long or short-term prophylaxis/treatment.

In some embodiments, the therapeutic effect of the anti-C-MET antibody molecule may persist for several multiples of the antibody half-life in serum, depending on the dose. For example, the therapeutic effect of a single dose of the anti-C-MET antibody molecule may persist in an individual for 1 month or more, 2 months or more, 3 months or more, 4 months or more, 5 months or more, or 6 months or more.

The invention also provides a method of producing an antibody molecule which specifically binds to human C-MET and optionally also to cynomolgus monkey C-MET or an antigen-binding portion thereof, comprising the steps of:
(1) grafting anti-C-MET CDRs from a non-human source into a human v-domain framework to produce a humanized anti-C-MET antibody molecule or antigen-binding portion thereof;
(2) generating a phage library of clones of the humanized anti-C-MET antibody molecule or antigen-binding portion thereof comprising one or more mutations in the CDRs;
(3) selecting the phage library for binding to human C-MET and optionally also to cynomolgus monkey C-MET;
(4) screening clones from the selection step (3) having binding specificity to human C-MET and optionally also to cynomolgus monkey C-MET; and
(5) producing an antibody molecule which specifically binds to human C-MET and optionally also to cynomolgus monkey C-MET, or an antigen-binding portion thereof from clones selected from step (4).

The method may comprise a further step of producing additional clones based on the clones selected in step (4), for example based on further exploratory mutagenesis at specific positions in the CDRs of the clones selected in step (4), to enhance humanization and/or minimise human T cell epitope content and/or improve manufacturing properties in the antibody molecule or antigen-binding portion thereof produced in step (5).

Refinements applicable to the above method are as described in Example 1 below.

As used herein, the term "C-MET" refers to the MET protein and variants thereof that retain at least part of the biological activity of C-MET. In some cases, as used herein, C-MET includes all mammalian species of native sequence C-MET, including human, rat, mouse and chicken. The term "C-MET" may be used to include variants, isoforms and species homologs of human C-MET. Antibodies of the invention may cross-react with C-MET from species other than human, in particular C-MET from cynomolgus monkey (*Macaca fascicularis*). Examples of human and cynomolgus C-MET amino acid sequences are provided in Table 12. In certain embodiments, the antibodies may be completely specific for human C-MET and may not exhibit non-human cross-reactivity.

As used herein, an "antagonist" as used in the context of the antibody of the invention or an "anti-C-MET antagonist antibody" (interchangeably termed "anti-C-MET antibody") refers to an antibody which is able to bind to C-MET and inhibit C-MET biological activity and/or downstream pathway(s) mediated by C-MET signalling. An anti-C-MET antagonist antibody encompasses antibodies that can block, antagonize, suppress or reduce (including significantly) C-MET biological activity, including downstream pathways mediated by C-MET signalling, such as receptor binding and/or elicitation of a cellular response to C-MET. For the purposes of the present invention, it will be explicitly understood that the term "anti-C-MET antagonist antibody" encompass all the terms, titles, and functional states and characteristics whereby C-MET itself, and C-MET biological activity, or the consequences of the activity or biological activity, are substantially nullified, decreased, or neutralized in any meaningful degree.

The antibody "specifically binds" "specifically interacts", "preferentially binds", "binds" or "interacts" with C-MET if it binds with greater affinity, avidity, more readily and/or with greater duration than it binds to other receptors.

An "antibody molecule" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody molecule" encompasses not only intact polyclonal or monoclonal antibodies, but also any antigen binding fragment (for example, an "antigen-binding portion") or single chain thereof, fusion proteins comprising an antibody, and any other modified configuration of the immunoglobulin molecule that comprises an antigen recognition site including, for example without limitation, scFv, single domain antibodies (for example, shark and camelid antibodies), maxibodies, minibodies, intrabodies, diabodies, triabodies, tetrabodies, v-NAR and bis-scFv.

An "antibody molecule" encompasses an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), for example IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

The term "antigen binding portion" of an antibody molecule, as used herein, refers to one or more fragments of an intact antibody that retain the ability to specifically bind to C-MET. Antigen binding functions of an antibody molecule can be performed by fragments of an intact antibody. Examples of binding fragments encompassed within the term "antigen binding portion" of an antibody molecule include Fab; Fab'; F(ab')2; an Fd fragment consisting of the VH and CH1 domains; an Fv fragment consisting of the VL and VH domains of a single arm of an antibody; a single domain antibody (dAb) fragment, and an isolated complementarity determining region (CDR).

The term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. The Fc region of an immunoglobulin generally comprises two constant domains, CH2 and CH3. As is known in the art, an Fc region can be present in dimer or monomeric form.

A "variable region" of an antibody refers to the variable region of the antibody light chain or the variable region of the antibody heavy chain, either alone or in combination. As known in the art, the variable regions of the heavy and light chain each consist of four framework regions (FRs) connected by three complementarity determining regions (CDRs) also known as hypervariable regions, and contribute to the formation of the antigen binding site of antibodies. When choosing FR to flank CDRs, for example when humanizing or optimizing an antibody, FRs from antibodies which contain CDR sequences in the same canonical class are preferred.

The CDR definitions used in the present application combine the domains used in the many disparate, often conflicting schemes that have been created in the field, which are based on the combination of immunoglobulin repertoire analyses and structural analyses of antibodies in isolation and in their co-crystals with antigens (see review by Swindells et al., 2016, abYsis: Integrated Antibody Sequence and Structure-Management, Analysis, and Prediction. J Mol Biol. [PMID: 27561707; Epub 22 Aug. 2016]). The CDR definition used herein (a "Unified" definition) incorporates the lessons of all such prior insights and includes all appropriate loop positions required to sample the full residue landscape that potentially mediates target-binding complementarity.

Table 1 shows the amino acid sequences of the 224G11 murine anti-C-MET antibody CDRs as defined herein (a "Unified" scheme), in comparison to well-known alternative systems for defining the same CDRs.

As used herein the term "conservative substitution" refers to replacement of an amino acid with another amino acid which does not significantly deleteriously change the functional activity. A preferred example of a "conservative substitution" is the replacement of one amino acid with another amino acid which has a value ≥0 in the following BLOSUM 62 substitution matrix (see Henikoff & Henikoff, 1992, PNAS 89: 10915-10919):

A "humanized" antibody molecule refers to a form of non-human (for example, murine) antibody molecules, or antigen-binding portion thereof, that are chimeric immunoglobulins, immunoglobulin chains, or fragments thereof (such as Fv, Fab, Fab', F(ab')2 or other antigen-binding sub-sequences of antibodies) that contain minimal sequence derived from non-human immunoglobulin. Humanized antibodies may be human immunoglobulins (recipient antibody) in which residues from a CDR of the recipient are replaced by residues from a CDR of a non-human species (donor antibody) such as mouse, rat, or rabbit having the desired specificity, affinity, and capacity.

"Human antibody or fully human antibody" refers to an antibody molecule, or antigen-binding portion thereof, derived from transgenic mice carrying human antibody genes or from human cells.

The term "chimeric antibody" is intended to refer to an antibody molecule, or antigen-binding portion thereof, in which the variable region sequences are derived from one species and the constant region sequences are derived from another species, such as an antibody molecule in which the variable region sequences are derived from a mouse antibody and the constant region sequences are derived from a human antibody.

"Antibody-drug conjugate" and "immunoconjugate" refer to an antibody molecule, or antigen-binding portion thereof, including antibody derivatives that binds to C-MET, which is conjugated to cytotoxic, cytostatic and/or therapeutic agents.

Antibody molecules of the invention, or antigen-binding portion thereof, can be produced using techniques well known in the art, for example recombinant technologies, phage display technologies, synthetic technologies or combinations of such technologies or other technologies readily known in the art.

The term "isolated molecule" (where the molecule is, for example, a polypeptide, a polynucleotide, or an antibody) is a molecule that by virtue of its origin or source of derivation

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | -1 | -2 | -2 | 0 | -1 | -1 | 0 | -2 | -1 | -1 | -1 | -1 | -2 | -1 | 1 | 0 | -3 | -2 | 0 |
| R | -1 | 5 | 0 | -2 | -3 | 1 | 0 | -2 | 0 | -3 | -2 | 2 | -1 | -3 | -2 | -1 | -1 | -3 | -2 | -3 |
| N | -2 | 0 | 6 | 1 | -3 | 0 | 0 | 0 | 1 | -3 | -3 | 0 | -2 | -3 | -2 | 1 | 0 | -4 | -2 | -3 |
| D | -2 | -2 | 1 | 6 | -3 | 0 | 2 | -1 | -1 | -3 | -4 | -1 | -3 | -3 | -1 | 0 | -1 | -4 | -3 | -3 |
| C | 0 | -3 | -3 | -3 | 9 | -3 | -4 | -3 | -3 | -1 | -1 | -3 | -1 | -2 | -3 | -1 | -1 | -2 | -2 | -1 |
| Q | -1 | 1 | 0 | 0 | -3 | 5 | 2 | -2 | 0 | -3 | -2 | 1 | 0 | -3 | -1 | 0 | -1 | -2 | -1 | -2 |
| E | -1 | 0 | 0 | 2 | -4 | 2 | 5 | -2 | 0 | -3 | -3 | 1 | -2 | -3 | -1 | 0 | -1 | -3 | -2 | -2 |
| G | 0 | -2 | 0 | -1 | -3 | -2 | -2 | 6 | -2 | -4 | -4 | -2 | -3 | -3 | -2 | 0 | -2 | -2 | -3 | -3 |
| H | -2 | 0 | 1 | -1 | -3 | 0 | 0 | -2 | 8 | -3 | -3 | -1 | -2 | -1 | -2 | -1 | -2 | -2 | 2 | -3 |
| I | -1 | -3 | -3 | -3 | -1 | -3 | -3 | -4 | -3 | 4 | 2 | -3 | 1 | 0 | -3 | -2 | -1 | -3 | -1 | 3 |
| L | -1 | -2 | -3 | -4 | -1 | -2 | -3 | -4 | -3 | 2 | 4 | -2 | 2 | 0 | -3 | -2 | -1 | -2 | -1 | 1 |
| K | -1 | 2 | 0 | -1 | -3 | 1 | 1 | -2 | -1 | -3 | -2 | 5 | -1 | -3 | -1 | 0 | -1 | -3 | -2 | -2 |
| M | -1 | -1 | -2 | -3 | -1 | 0 | -2 | -3 | -2 | 1 | 2 | -1 | 5 | 0 | -2 | -1 | -1 | -1 | -1 | 1 |
| F | -2 | -3 | -3 | -3 | -2 | -3 | -3 | -3 | -1 | 0 | 0 | -3 | 0 | 6 | -4 | -2 | -2 | 1 | 3 | -1 |
| P | -1 | -2 | -2 | -1 | -3 | -1 | -1 | -2 | -2 | -3 | -3 | -1 | -2 | -4 | 7 | -1 | -1 | -4 | -3 | -2 |
| S | 1 | -1 | 1 | 0 | -1 | 0 | 0 | 0 | -1 | -2 | -2 | 0 | -1 | -2 | -1 | 4 | 1 | -3 | -2 | -2 |
| T | 0 | -1 | 0 | -1 | -1 | -1 | -1 | -2 | -2 | -1 | -1 | -1 | -1 | -2 | -1 | 1 | 5 | -2 | -2 | 0 |
| W | -3 | -3 | -4 | -4 | -2 | -2 | -3 | -2 | -2 | -3 | -2 | -3 | -1 | 1 | -4 | -3 | -2 | 11 | 2 | -3 |
| Y | -2 | -2 | -2 | -3 | -2 | -1 | -2 | -3 | 2 | -1 | -1 | -2 | -1 | 3 | -3 | -2 | -2 | 2 | 7 | -1 |
| V | 0 | -3 | -3 | -3 | -1 | -2 | -2 | -3 | -3 | 3 | 1 | -2 | 1 | -1 | -2 | -2 | 0 | -3 | -1 | 4. |

The term "monoclonal antibody" (Mab) refers to an antibody, or antigen-binding portion thereof, that is derived from a single copy or clone, including for example any eukaryotic, prokaryotic, or phage clone, and not the method by which it is produced. Preferably, a monoclonal antibody of the invention exists in a homogeneous or substantially homogeneous population.

(1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

The term "epitope" refers to that portion of a molecule capable of being recognized by and bound by an antibody molecule, or antigen-binding portion thereof, at one or more of the antibody molecule's antigen-binding regions. Epitopes can consist of defined regions of primary secondary or tertiary protein structure and includes combinations of secondary structural units or structural domains of the target recognised by the antigen binding regions of the antibody, or antigen-binding portion thereof. Epitopes can likewise consist of a defined chemically active surface grouping of molecules such as amino acids or sugar side chains and have specific three-dimensional structural characteristics as well as specific charge characteristics. The term "antigenic epitope" as used herein, is defined as a portion of a polypeptide to which an antibody molecule can specifically bind as determined by any method well known in the art, for example, by conventional immunoassays, antibody competitive binding assays or by x-ray crystallography or related structural determination methods (for example NMR).

The term "binding affinity" or "KD" refers to the dissociation rate of a particular antigen-antibody interaction. The KD is the ratio of the rate of dissociation, also called the "off-rate ($k_{off}$)", to the association rate, or "on-rate ($k_{on}$)". Thus, $K_D$ equals $k_{off}/k_{on}$, and is expressed as a molar concentration (M). It follows that the smaller the $K_D$, the stronger the affinity of binding. Therefore, a $K_D$ of 1 µM indicates weak binding affinity compared to a $K_D$ of 1 nM. KD values for antibodies can be determined using methods well established in the art. One method for determining the KD of an antibody is by using surface plasmon resonance (SPR), typically using a biosensor system such as a Biacore® system.

The term "potency" is a measurement of biological activity and may be designated as $IC_{50}$, or effective concentration of an antibody or antibody drug conjugate to the antigen C-MET to inhibit 50% of activity measured in a C-MET activity assay as described herein.

The phrase "effective amount" or "therapeutically effective amount" as used herein refers to an amount necessary (at dosages and for periods of time and for the means of administration) to achieve the desired therapeutic result. An effective amount is at least the minimal amount, but less than a toxic amount, of an active agent which is necessary to impart therapeutic benefit to a subject.

The term "inhibit" or "neutralize" as used herein with respect to bioactivity of an antibody molecule of the invention means the ability of the antibody to substantially antagonize, prohibit, prevent, restrain, slow, disrupt, eliminate, stop, reduce or reverse for example progression or severity of that which is being inhibited including, but not limited to, a biological activity or binding interaction of the antibody molecule to C-MET.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The term "treating", as used herein, unless otherwise indicated, means reversing, alleviating, inhibiting the progress of, delaying the progression of, delaying the onset of, or preventing the disorder or condition to which such term applies, or one or more symptoms of such disorder or condition. The term "treatment", as used herein, unless otherwise indicated, refers to the act of treating as defined above. The term "treating" also includes adjuvant and neoadjuvant treatment of a subject. For the avoidance of doubt, reference herein to "treatment" includes reference to curative, palliative and prophylactic treatment. For the avoidance of doubt, references herein to "treatment" also include references to curative, palliative and prophylactic treatment.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. Any example(s) following the term "e.g." or "for example" is not meant to be exhaustive or limiting.

The practice of the present invention will employ, unless otherwise indicated, conventional techniques of molecular biology (including recombinant techniques), microbiology, cell biology, biochemistry and immunology, which are within the skill of the art.

Particular non-limiting embodiments of the present invention will now be described with reference to accompanying drawings.

Example 1. Generation of Optimized Anti-C-MET Therapeutic Antibodies

Introduction

In this example, we successfully generate a panel of antagonistic, optimized anti-C-MET antibodies. These anti-C-MET antibodies are well expressed, biophysically stable, highly soluble and of maximized amino acid sequence identity to preferred human germlines.

Materials and Methods

C-MET Library Generation and Selection

The C-MET Fab repertoire was assembled by mass oligo synthesis and PCR. The amplified Fab repertoire was then cloned via restriction-ligation into a phagemid vector, transformed into *E. coli* TG-1 cells, and the phage repertoire rescued essentially as previously described in detail (Finlay et al., 2011, Methods Mol Biol 681: 383-401).

Phage selections were performed by coating streptavidin magnetic microbeads with biotinylated C-MET target protein (either human or cyno), washing the beads thrice with PBS and resuspending in PBS pH7.4 plus 5% skim milk protein. These beads were coated at 100 nM target protein in round 1 of selection, followed by reduced antigen concentrations in three successive rounds. In each round, phage were eluted using trypsin before re-infection into TG1 cells.

Periplasmic Extracts Production (Small-Scale)

Production of soluble Fabs in individual *E. coli* clones was performed. *E. coli* TG1 cells in logarhythmic growth phase were induced with isopropyl 1-thio-β-D-galactopyranoside. Periplasmic extracts containing soluble Fab were generated by a freeze/thaw cycle: Bacterial cell pellets were frozen at −20° C. for overnight and then thawed at room temperature and resuspended in PBS pH 7.4. The supernatants containing the soluble Fab were collected after shaking at room temperature and centrifugation.

IgG Expression and Purification

Mammalian codon-optimized synthetic genes encoding the heavy and light chain variable domains of the lead panel anti-C-MET antibodies plus the h224G11 and grafted (Graft) were cloned into mammalian expression vectors comprising IgG4(S228P) ('IgG4(S228P)'; human IgG4 containing S228P mutation in the hinge that stabilises the tertiary structure of the molecule) and human $C_K$ domains, respectively. Co-transfection of heavy and light chain containing vector in mammalian expression system was performed, followed by protein A-based purification of the IgG, quantification and QC on denaturing and non-denaturing SDS-PAGE.

Direct binding ELISA for Fab and IgG

Binding and cross-reactivity of the lead panel to the recombinant proteins was initially assessed by binding ELISA. The human C-MET human Fc tagged recombinant protein and the cynomolgus monkey C-MET human Fc tagged recombinant protein were coated to the surface of MaxiSorp™ flat-bottom 96 well plate at 1 μg/ml. The purified IgG samples were titrated in two fold serial dilutions starting from 500 nM to 0.98 nM and allowed to bind to the coated antigens. The Fabs were detected using mouse anti-c-myc antibody followed by donkey anti-mouse IgG conjugated to horseradish peroxidase. The IgGs were detected using the mouse anti-human IgG conjugated to horseradish peroxidase. Binding signals were visualized with 3,3',5,5'-Tetramethylbenzidine Substrate Solution (TMB) and the absorbance measured at 450 nm. IgG binding analysis via ELISA on negatively charged biomolecular surfaces to calculate off-target binding and PK risk were performed as previously described (see Avery et al., 2018, MAbs 10 (2), 244-255).

AlphaScreen Epitope Competition Assay for IgG4(S228P) Antibodies

The AlphaScreen assay (Perkin Elmer) was performed in a 25 μl final volume in 384-well white microtiter plates (Greiner). The reaction buffer contained 1×PBS pH 7.3 (Oxoid, Cat. nr. BR0014G) and 0.05% (v/v) Tween® 20 (Sigma, Cat. nr. P9416). Purified IgG samples were titrated in three fold serial dilutions starting at 50 nM final concentration and incubated with biotinylated human C-MET-His (Acrobiosystems) at 1 nM final concentration for 20 minutes at room temperature. The parental IgG and the anti-human IgG4(S228P) Acceptor beads at were added and the mix was incubated for 1 hour at room temperature. Followed by addition of the Streptavidin Donor beads and incubation for 30 minutes at room temperature. The emission of light was measured in the EnVision multilabel plate reader (Perkin Elmer) and analysed using the EnVision manager software. Values were reported as Counts Per Second (CPS) and corrected for crosstalk.

Biacore® Analyses of IgG Affinity for Monomeric Human and Cyno C-MET in Solution Affinity (KD) of purified IgGs was determined via SPR with antigen in-solution on a Biacore® 3000 (GE). A mouse anti-human antibody (CH1 specific) was immobilized on a CM5 Sensor Chip to a level of 2000 RU in acetate buffer at pH 4.5 using amine coupling following the Wizard instructions for two channels. One channel was used for background signal correction. The standard running buffer HBS-EP pH 7.4 was used. Regeneration was performed with a single injection of 10 μl of 10 mM Glycine at pH 1.5 at 20 μl/minute. IgG samples were injected for 2 minutes at 50 nM at 30 μl/min followed by and off-rate of 60 seconds. The monomeric antigen (human C-MET His tagged or cynomolgus monkey C-MET His tag) was injected in two fold serial dilutions from 100 nM down to 6 nM, for 2 minutes at 30 μl/min followed by an off-rate of 300 seconds. The obtained sensorgrams were analysed using the Biacore® 3000 evaluation (BIAevaluation) software. The KD was calculated by simultaneous fitting of the association and dissociation phases to a 1:1 Langmuir binding model.

Flow Cytometry of IgGs

Purified IgGs were tested in FACs for binding to human and cyno C-MET expressed on CHO-K1 stable cell lines and CHO-K1 wild-type cells. The IgG samples were titrated in three-fold serial dilutions starting at 500 nM to 0.08 nM. Binding of IgGs was detected with a mouse anti-human IgG conjugated to FITC. Results were analyzed by examining the Mean Fluorescence Intensity (MFI) of 10000 cells per sample in the BL-1 channel detector of a flow cytometer (Attune™ NxT Acoustic Focusing Cytometer, Invitrogen/ThermoFisher Scientific). The EC50 values were calculated using the MFI values in GraphPad Prism software (GraphPad Software, La Jolla, Calif.) and 4 parameters.

Antibody v-Domain T Cell Epitope Content: In Silico Analyses

In silico technologies (Abzena, Ltd.), which are based on identifying the location of T cell epitopes in therapeutic antibodies and proteins, were used for assessing potential immunogenicity in antibody v-domains. iTope™ was used to analyse the VL and VH sequences of key leads for peptides with promiscuous high affinity binding to human MHC class II. Promiscuous high affinity MHC class II binding peptides are thought to correlate with the presence of T cell epitopes that are high risk indicators for clinical immunogenicity of drug proteins. The iTope™ software predicts favourable interactions between amino acid side chains of a peptide and specific binding pockets (in particular pocket positions; p1, p4, p6, p7 and p9) within the open-ended binding grooves of 34 human MHC class II alleles. These alleles represent the most common HLA-DR alleles found world-wide with no weighting attributed to those found most prevalently in any particular ethnic population. Twenty of the alleles contain the 'open' p1 configuration and 14 contain the 'closed' configuration where glycine at position 83 is replaced by a valine. The location of key binding residues is achieved by the in silico generation of 9mer peptides that overlap by eight amino acids spanning the test protein sequence. This process successfully discriminates with high accuracy between peptides that either bind or do not bind MHC class II molecules.

In addition, the sequences were analysed using TCED™ (T Cell Epitope Database™) search for matches to T cell epitopes previously identified by in vitro human T cell epitope mapping analyses of other protein sequences. The TCED™ is used to search any test sequence against a large (>10,000 peptides) database of peptides derived from unrelated protein and antibody sequences.

Differential Scanning Calorimetry (DSC) Analysis

The Tm of test articles was analysed using a MicroCal PEAQ-DSC (Malvern Instruments, Malvern, UK) running version 1.22 software. The samples were heated at a rate of 200° C./hour over a range of 20–110° C. Thermal data was normalised based on protein concentration. The Tm of the protein was determined from the heating scan data.

Charge Variant Assay

Charge variant profiling of test articles was determined by Protein Charge Variant Assay on a LabChip GXII Touch HT (PerkinElmer, Beaconsfield, UK), according to the manufacturer's protocol.

Isoelectric Focusing Assay

IEF analysis for the lead IgG4(S228P) proteins was performed to assess possible differences in pI. Electrophoresis was performed using an Invitrogen™ Novex™ pH 3-10 IEF Protein Gel, using Novex™ IEF Sample Buffer pH 3-10, Novex™ IEF Anode and Cathode Buffers. pI values were estimated based on the IEF pI marker values (Serva). Brentuximab and Infliximab IgG1s were included as controls.

Results and Discussion

CDR Grafting onto Preferred Human Germline v-Genes

The CDRs of an antagonistic murine anti-C-MET IgG 224G11 (224G11; see WO2011151412A1 and Table 2) were initially introduced to human germline immunoglobulin v-domain framework sequence scaffolds using CDR grafting. To bias our engineering efforts towards final lead therapeutic IgG compounds with optimal drug-like properties, we chose to graft the CDRs of the parental antibody onto "preferred" germline scaffolds IGHV1-46 and IGKV3-20, which are known to have good solubility, high physical stability and are used at high frequency in the expressed human antibody repertoire.

Those scaffolds and grafted CDR definitions are outlined in Table 2. The heavy and light chain sequences for chimeric anti-C-MET antibody m224G11 and humanized h224G11 are also shown in Table 2. While this process of CDR grafting is well known, it is still problematic to predict whether a given set of human v-domain sequences will act as suitable acceptor frameworks for non-human CDR grafting. The use of unsuitable frameworks can lead to the loss of target binding function, protein stability issues or even impaired expression of the final IgG. The IGHV1-46/IGKV3-20 graft was therefore taken forward as the template for CDR mutagenesis and selection of improved clones.

Library Generation and Screening

The CDR-grafted IGKV3-20/IGHV1-46 v-domain sequences were combined into a Fab phage display format and a mutagenesis library cassette was generated by oligo synthesis and assembly. The final Fab library was ligated into a phage display vector and transformed into E. coli via electroporation to generate $2.5 \times 10^9$ independent clones. Library build quality was verified by sequencing 96 clones, across both v-domains. This sequencing data showed that the positions encoding either the murine or human germline residue at each position of variance had been effectively sampled at a frequency of approximately 50% (or e.g. 33% in positions where 3 amino acids where encoded). Libraries were rescued using helper phage M13 and selections performed on biotinylated human and cynomolgus monkey C-MET-Fc proteins in multiple separate branches.

Figure 1B:
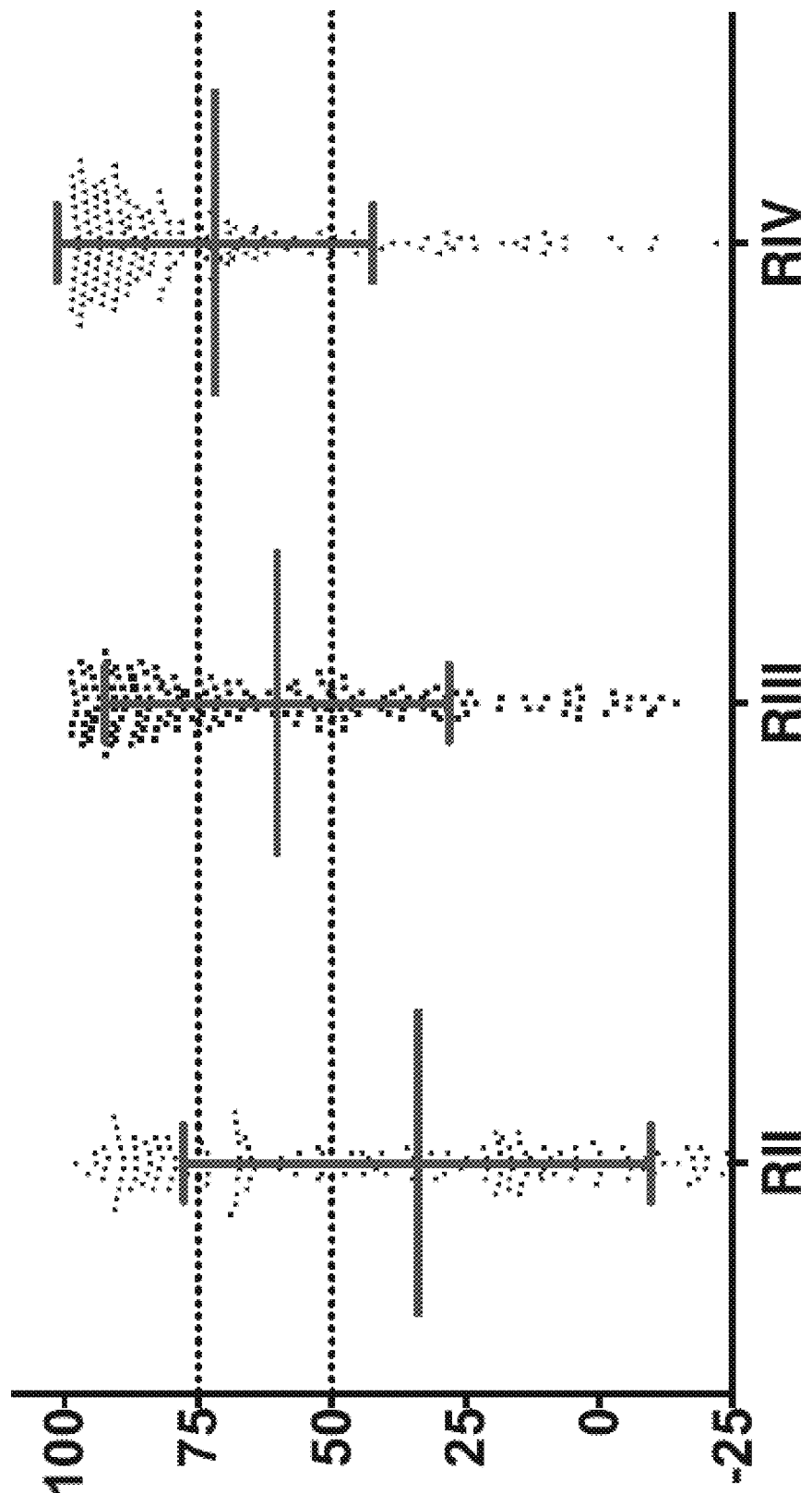

Post-selection screening and DNA sequencing revealed the presence of 131 unique, human and cyno C-MET-binding Fab clones that exhibited strong binding to human and cyno C-MET in ELISA (FIG. 1A) and >50% inhibition of 224G11 IgG4(S228P) binding to human C-MET in Alphascreen assay (FIG. 1B). Amongst these 131 clones, the framework sequences remained fully germline while humanizing mutations were also observed in all CDRs (Table 3). Lead clones were ranked based on level of CDR germlining versus ELISA and Alphascreen signals for binding to both human and cyno C-MET-Fc. The v-domains of the 9 top clones from this ranking were then sub-cloned into IgG expression vectors for further testing as below (Table 4).

Figure 2A:
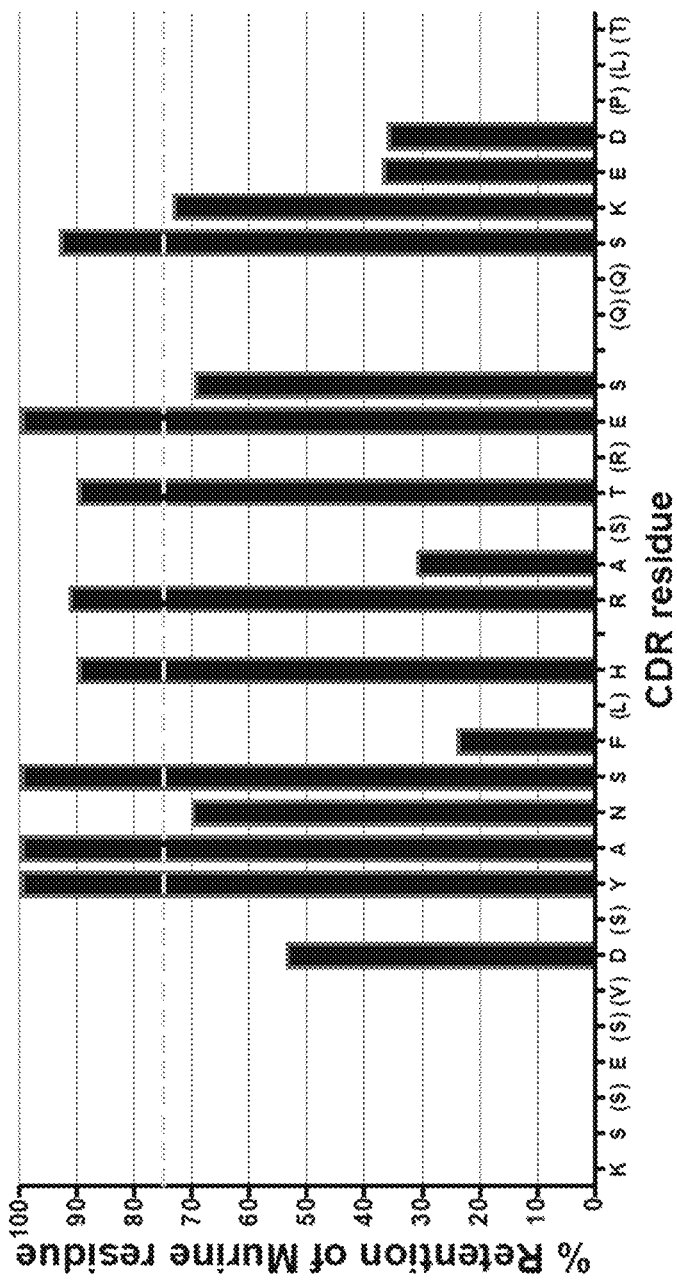
FIG. 2A-FIG. 2B. Analysis of CDR residue tolerance for mutation to germline. A plot of murine amino acid retention frequencies in the CDRs of the ELISA-positive population of 131 unique Fab clones that demonstrated human and cyno CMET cross-reactivity is shown for VL (SEQ ID NOs: 58-60) (FIG. 2A) and VH (SEQ ID NOs: 61-63) (FIG. 2B) domains, respectively. Only those residues targeted for human/murine residue mutagenesis are plotted, other than in the HCDR3. CDR residues noted in parentheses on the X-axes were identical to those found in the human germlines used for grafting (IGKV3-20 and IGHV1-46). Those residues in the CDRs that are not in parentheses, but whose values are set at 0, were mutated to human germline during the grafting process. In both plots the dashed line in grey at 75% represents the cut off for tolerance of murine residue replacement by human germline.
Figure 2B:
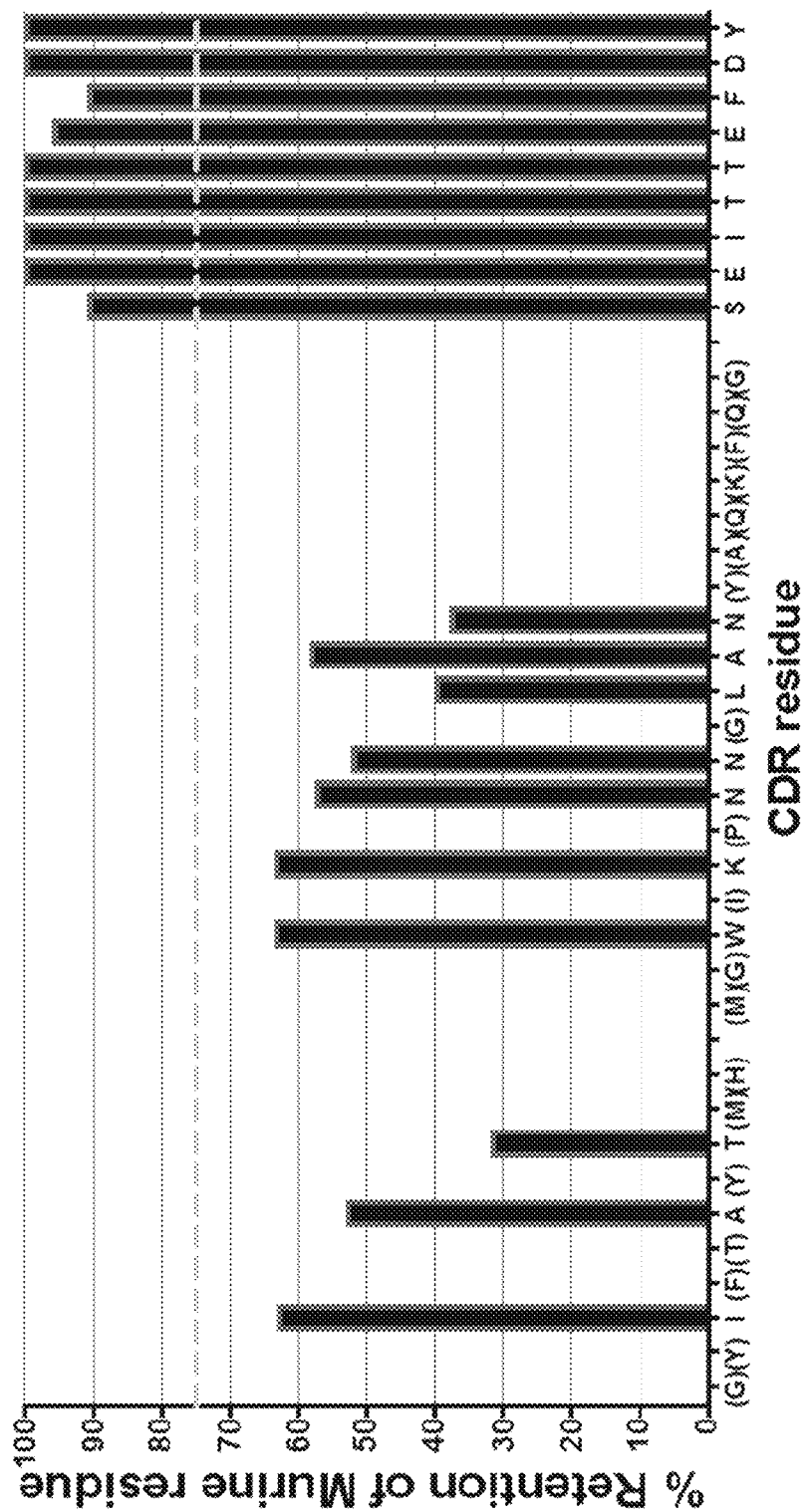

While germ-lining mutations were observed in all CDRs for the lead clones derived directly from library selections, it remained possible that sequence analyses might allow further clones to be designed to have maximal humanization. The 131 sequence-unique hits with binding signals against human and cyno protein were therefore used to analyse the retention frequency for murine amino acids in the CDRs of this functionally characterized population. Positional amino acid retention frequency was expressed as a percentage found in the VL and VH domains (FIGS. 2A&B, respectively). Murine residues with RF<75% were regarded as positions that are possibly not essential to the target-binding paratope and are likely to be open to germ-lining, in a series of combinatorial designs (Table 4). In a surprising finding, none of the 10 murine residues in the HCDR1 and HCDR2 exhibited retention frequency above 75% (FIG. 2A). This analysis strongly suggested that the entire VH sequence outside the HCDR3 could possibly be rendered germline identity to IGHV1-46. In the $V_L$ domain, in contrast, 8 of 16 murine CDR residues derived from the h224G11 sequence were retained with frequencies >75% (FIG. 3A).

Designs containing combinations of those murine residues with RF>75% were given the prefix "MH" (MH=Maximally Humanized). In total 4 designer $V_H$ and 3 designer $V_L$ domains were generated. These constructs were co-transfected in a matrixed fashion to create 12 final designer IgGs in total (Table 4). The MH and library-derived clone v-domains were generated by gene synthesis and (along with the control antibodies), cloned into human expression vectors for production in IgG4(S228P) format. All IgGs were readily expressed and purified from transient transfections of mammalian cells.

Lead IgG Specificity and Potency Characteristics

Figure 3:
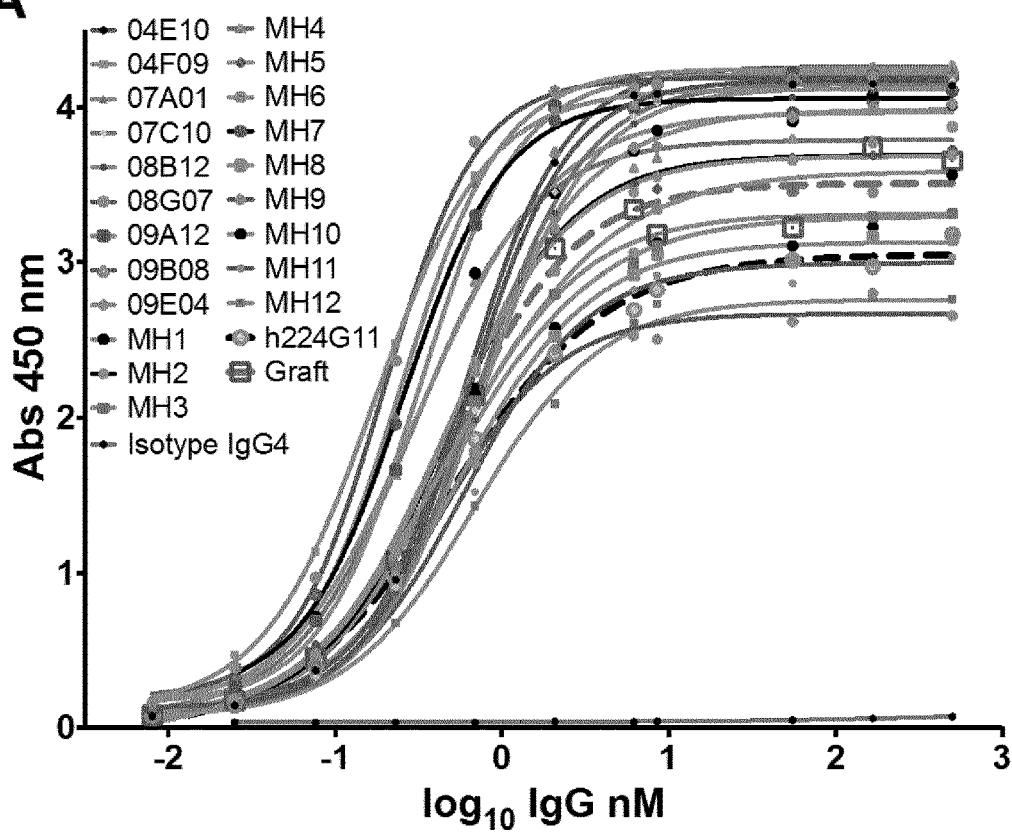
FIG. 3A-FIG. 3B. Direct titration ELISA for IgG binding to human and cyno C-MET-Fc proteins. Humanized h224G11, Grafted clone (Graft), library-derived and designer clones in human IgG4(S228P) format were titrated (in nM) in a direct binding ELISA against human (FIG. 3A) and cyno (FIG. 3B) C-MET-Fc proteins. All clones other than Isotype IgG4 control demonstrated binding activity against both orthologs of C-MET, with approximately equivalent or improved human and cyno C-MET binding.
Figure 3:
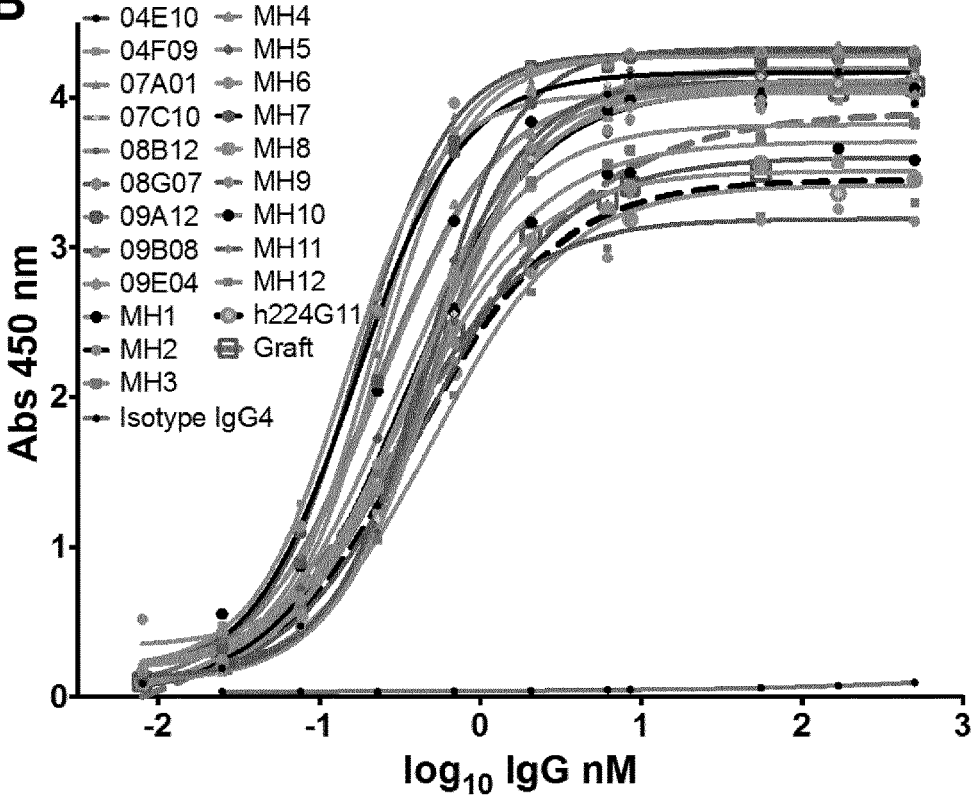

The purified IgGs described above were then tested for binding to human and cyno C-MET-Fc in direct titration ELISA format (FIGS. 3A&B). This analysis demonstrated that all library derived and designer (MH) clones retained binding activity for human and cyno C-MET that was equivalent to, or improved over, the h224G11 IgG4(S228P).

Figure 4:
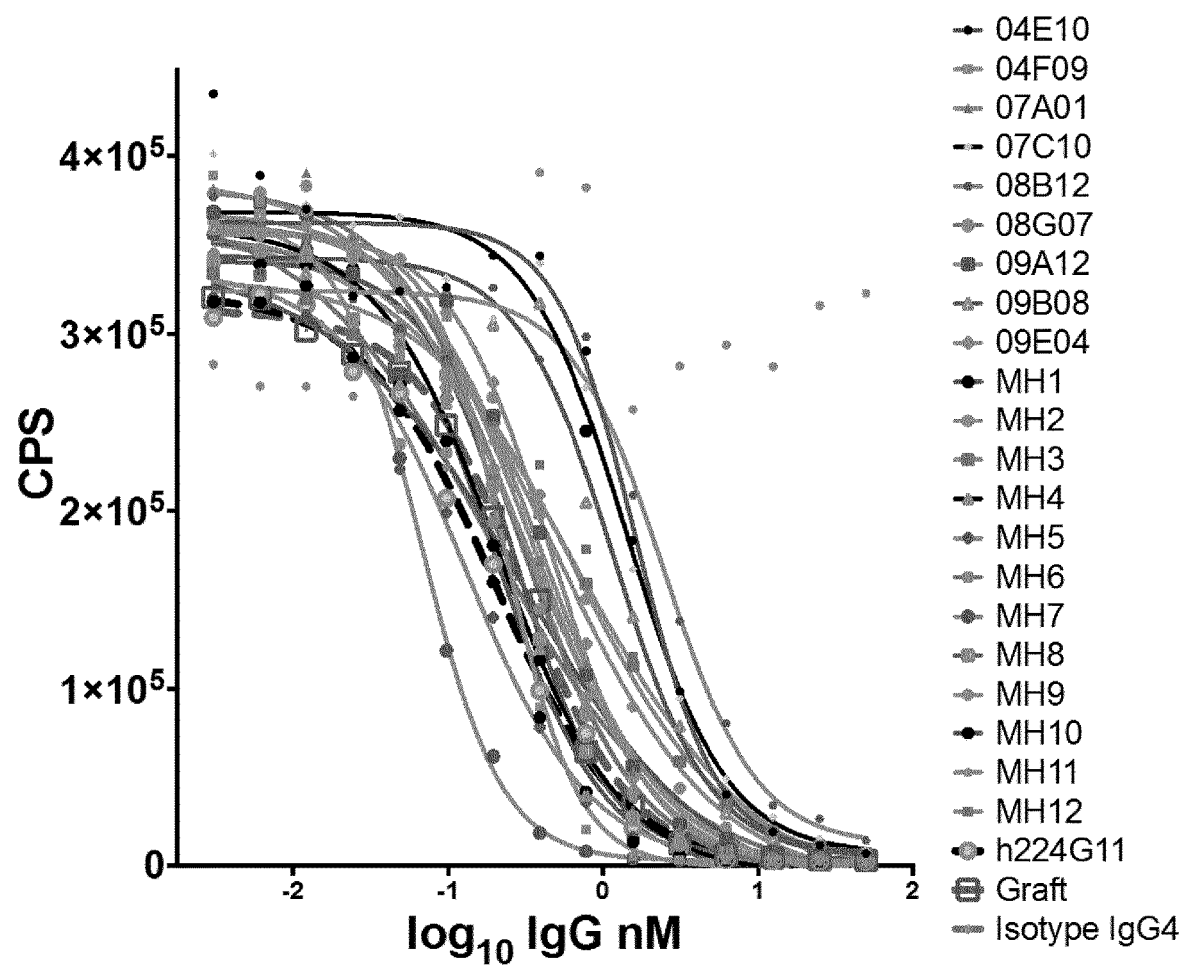
FIG. 4. Epitope competition analysis of IgG4(S228P) proteins in Alphascreen. Anti-C-MET IgG4(S228P) clones were applied in an epitope competition assay using Alphascreen technology. In this assay, library-derived and designer IgGs were analysed for their retention of the parental 224G11 epitope by competing for 224G11 IgG4 (S228P) binding to human C-MET protein, in solution. All clones analysed showed strong, concentration-dependent neutralisation of 224G11 binding to C-MET.

An Alphascreen assay was established to allow the testing of IgGs for epitope competition with h224G11 IgG binding to biotinylated monomeric human C-MET. In this assay, the top-performing library-derived and designer IgGs were more effectively differentiated. While all clones exhibited full, concentration-dependent neutralisation, and the majority of clones exhibited equivalent or improved competition for the h224G11 epitope over h224G11 (FIG. 4), some exhibited less potent epitope competition including: 08G12, 04E10, 09G08, 07C10.

Biacore® analyses of binding affinity were performed for all IgGs to solution-phase, monomeric human and cyno C-MET proteins. In all cases, accurate 1:1 binding affinities with low $Chi^2$ values were obtained (Table 5). These analyses showed that library-derived clones which consistently gave the highest EC50 and IC50 values in Fab and IgG ELISA and Alphascreen assays also showed highest affinity binding to human and cyno C-MET. Unexpectedly, library-derived clones 08G07, 04F09, 09E04, 07A01 and designer clones MH4 and MH7 all exhibited significantly improved binding affinities for human C-MET in comparison to h224G11 (Table 5). Importantly, these improvements in affinity were recapitulated in cyno binding, with each of these clones exhibiting affinities within 2-fold of the human C-MET affinity. Affinity differentials of less than 3-fold between human and cyno target orthologs are highly beneficial in pre-clinical drug development analyses as they allow significantly better design and interpretation of e.g. monkey safety, PK and PD modelling experiments. The Biacore® analyses also showed that the reduced epitope competition potency observed for clones 08G12, 04E10, 09G08, 07C10 in the Alphascreen assay (FIG. 4) was driven by reduced human C-MET binding affinity, rather than any alteration in binding epitope.

In addition, comparison of the affinities of MH clones confirmed the influence of the LCDR3 in maintaining binding affinity, as mutations of the residues 'SK' at positions 3 and 4 both resulted in approximately 10 to 20-fold loss of KD for clones MH8 and MH9 in comparison to clone MH7, against both human and cyno C-MET (Table 5). Comparison of clones MH4 and MH10 also confirmed that the mutation of HCDR1 residue 8 (T to A) led to an approximately 2-fold reduction in binding affinity for human C-MET in clone MH10, but no significant reduction in affinity for cyno C-MET (Table 5). Importantly, however, this T>A mutation in clone MH10 rendered the HCDR1 fully germline for the human germline sequence IGHV1-3. As IGHV1-3 and IGHV1-46 are sequence-identical 10 amino acids in either N or C-terminal directions from the T>A mutation, this rendered the HCDR1 sequence fully deimmunised for human t cell epitopes due to thymic tolerance (human t-cell epitopes being based on core 9-mer amino acid sequence).

The findings outlined above confirmed that the MH7 clone could fully retain (and improve over) the binding affinity, epitope specificity and species cross-reactivity of h224G11, while retaining only a single non-germline amino acid in the VH domain (excluding the HCDR3, for which there is no corresponding germline). In addition, the fully germlined HCDR2 of MH7 removed 3 potential amino acid development liability sequences found in the h224G11 antibody: A putative oxidation risk at position 3 (W), plus two deamidation risk motifs at positions 7 and 8 (both N). In the light chain of MH7, three additional development liability sequences found in h224G11 were removed: a 'DS' aspartic acid isomerisation motif in LCDR1 position 7, and oxidation risk at LCDR1 position 13 (F) and a 'DP' acid hydrolysis motif in LCDR3 at position 6. These improvements in primary sequence are of direct consequence in both manufacturing and clinical development of an antibody therapeutic as they are all potential protein degradation risk motifs, leading to intrinsic product heterogeneity. Such risk motifs can lead to costly development issues where multiple process modifications must be made to maximise intact antibody yield and to minimise product heterogeneity. Degradation motifs are also a clinical development risk, as accelerated antibody breakdown in the body can reduce both half-life and potency of the molecule.

Flow Cytometric Analyses of Lead IgG Binding Specificity at the Cell Membrane

Figure 5:
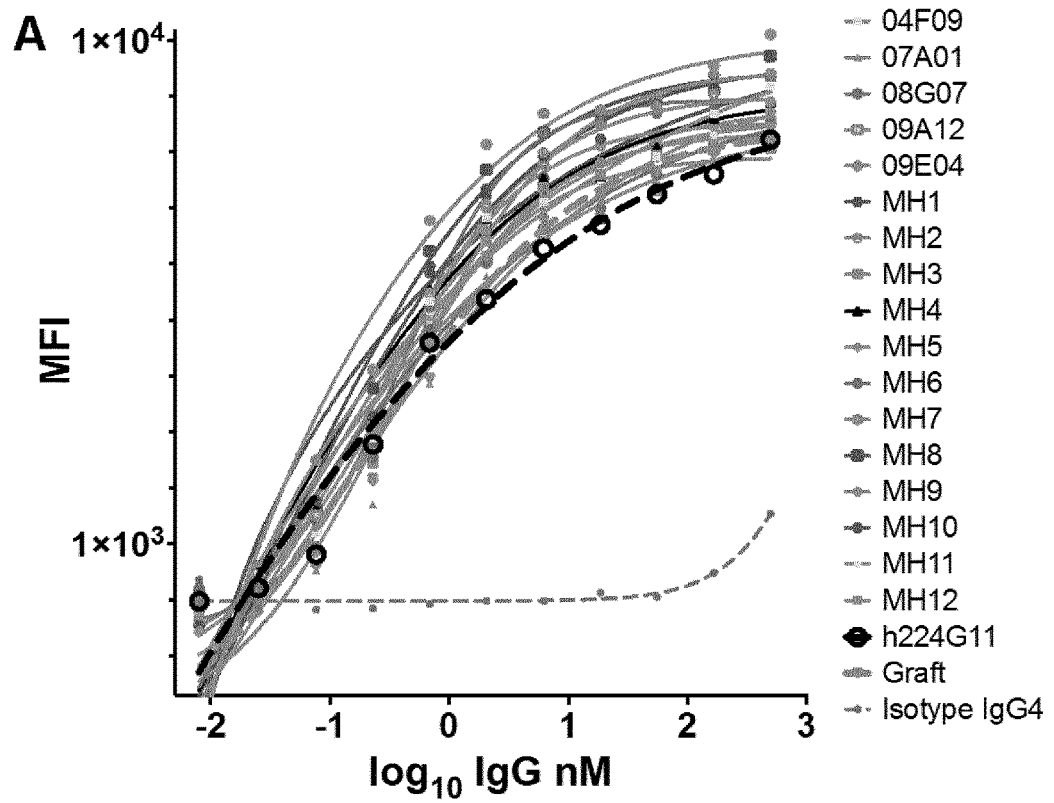
FIG. 5A-FIG. 5B. Flow cytometric binding to human and cyno C-MET+CHO-K1 cells for library-derived and primary designer leads. Anti-C-MET controls h224G11 and Graft, library-derived and designer leads in IgG4(S228P) format were examined for specific binding on human C-MET-transfected CHO-K1 cells (FIG. 5A) and cyno C-MET-transfected CHO-K1 cells (FIG. 5B). IgGs were tested at concentrations ranging from 500-0.08 nM. Concentration-dependent binding was observed against both human and cyno cell lines for all C-MET-specific antibodies but not isotype control IgG4.
Figure 5:
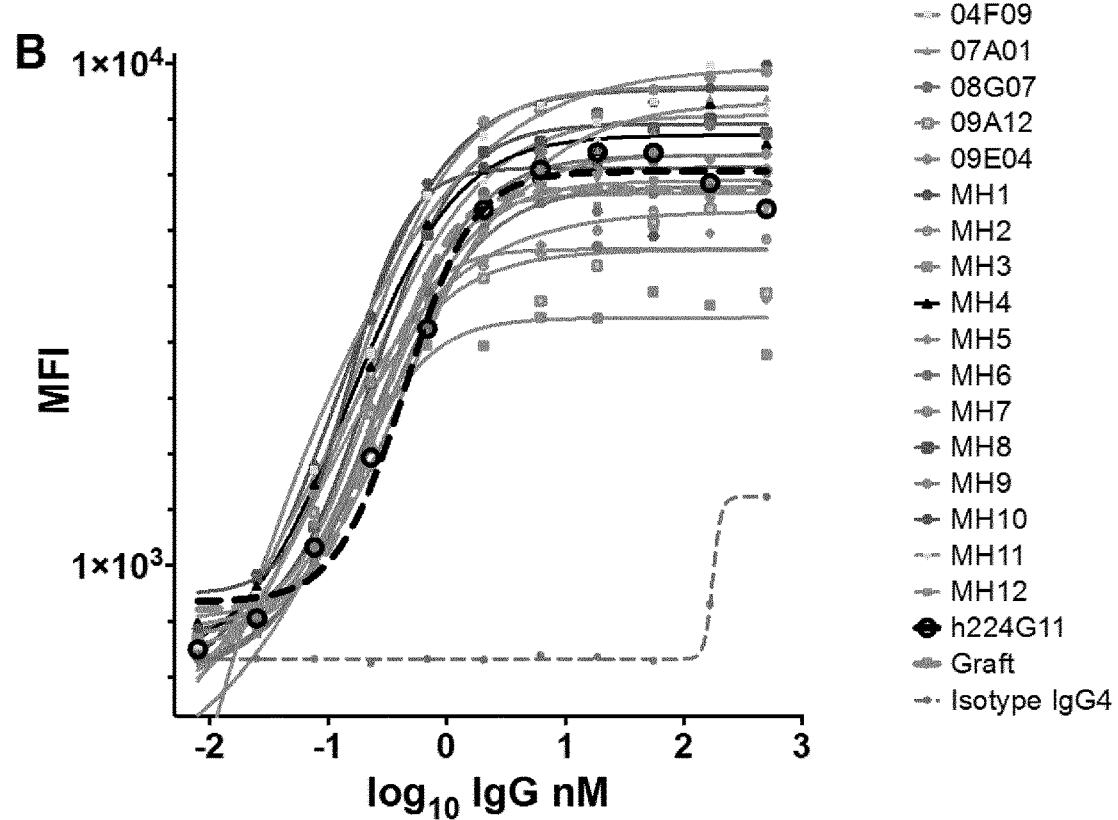

Antibodies to C-MET were analysed for concentration-dependent binding at the cell surface via flow cytometry. CHO-K1 cells were stably transfected with either human or cyno C-MET full-length cDNAs. Anti-C-MET IgGs and an isotype control IgG4(S228P) were then all tested in IgG4(S228P) format, over a concentration range of 500-0.08 nM for binding to human (FIG. 5A) and cyno (FIG. 5B) CHO-K1 cells. All IgGs other than the isotype control showed concentration-dependent binding to human and cyno C-MET+ cells, equivalent to, or improved over h224G11, with a maximum MFI in each case being >10-fold higher than observed background signals for Isotype IgG4. Several clones, including MH1, MH4, MH7 and MH10 exhibited stronger binding profiles and improved EC50 values for binding to both human and cyno+ CHO-K1 cells, in comparison to h224G11 (Table 6).

Antibody v-Domain T Cell Epitope Analyses

In silico technologies (Abzena, Ltd.), which are based on identifying the location of T cell epitopes in therapeutic antibodies and proteins, were used for assessing the immunogenicity of both the h224G11 and lead antibody v-domains. Analysis of the v-domain sequences was performed with overlapping 9mer peptides (with each overlapping the last peptide by 8 residues) which were tested against each of the 34 MHC class II allotypes. Each 9mer was scored based on the potential 'fit' and interactions with the MHC class II molecules. The peptide scores calculated by the software lie between 0 and 1. Peptides that produced a high mean binding score (>0.55 in the iTope™ scoring function) were highlighted and, if >50% of the MHC class II binding peptides (i.e. 17 out of 34 alleles) had a high binding affinity (score >0.6), such peptides were defined as 'high affinity' MHC class II binding peptides which are considered a high risk for containing CD4+ T cell epitopes. Low affinity MHC class II binding peptides bind a high number of alleles (>50%) with a binding score >0.55 (but without a majority >0.6). Further analysis of the sequences was performed using the TCED™. The sequences were used to interrogate the TCED™ by BLAST search in order to identify any high sequence homology between peptides (T cell epitopes) from unrelated proteins/antibodies that stimulated T cell responses in previous in vitro T cell epitope mapping studies performed at Abzena Ltd.

Peptides were grouped into four classes: High Affinity Foreign ('HAF'—high immunogenicity risk), Low Affinity Foreign ('LAF'—lower immunogenicity risk), TCED+ (previously identified epitope in TCED™ database), and Germline Epitope ('GE'-human germline peptide sequence with high MHC Class II binding affinity). Germline Epitope 9mer peptides are unlikely to have immunogenic potential due to T cell tolerance, as validated by previous studies with a wide range of germline peptides. Importantly, such germline v-domain epitopes (aided further by similar sequences in the human antibody constant regions) also compete for MHC Class II occupancy at the membrane of antigen presenting cells, reducing the risk of foreign peptide presentation being sufficient to achieve the 'activation threshold' required for T cell stimulation. High GE content is therefore a beneficial quality in clinical development of an antibody therapeutic.

As shown in Table 7, the h224G11 v-domains sequences were found to contain significant foreign epitope risk despite having been humanized onto germline framework sequences.

In the VL domain, h224G11 was found to contain two HAF peptide motifs ('LLIYRASTR' (SEQ ID NO: 91) and 'IYRASTRES' (SEQ ID NO: 92), both containing LCDR2 residues) and one LAF motif ('VAVYYCQQS' (SEQ ID NO: 93)). In the VH domain, h224G11 was also found to contain two HAF peptide motifs ('IFTAYTMH' (SEQ ID NO: 94), containing HCDR1 residues, and 'VYYCARSEI' (SEQ ID NO: 95), containing HCDR3 residues) and one LAF motif ('MGWIKPNNG' (SEQ ID NO: 96), containing HCDR2 residues).

Key lead v-domains exhibited significant beneficial changes in peptide epitope content in comparison to h224G11 (Table 7). As the v-domain engineering process undertaken here had successfully selected for antibodies that maintained anti-MET potency without the need for many of the murine residues included in the CDRs of h224G11 (Table 2, Table 4), multiple HAF and LAF epitopes found in the v-domains of h224G11 were ablated in library-derived and designer leads, leading to reduced HAF and/or LAF content (Table 7). GE epitope content was also found to be significantly increased in the VH regions of lead clones, and TCED+ epitopes were not observed in any lead clone (Table 7). These findings were exemplified by the clone MH7, where the near-complete germlining of the VH domain CDRs 1 and 2 not only removed several development liability sequences (as described above), but also ablated the HAF peptide motif 'IFTAYTMHW' (SEQ ID NO: 97), and the LAF motif 'MGWIKPNNG' (SEQ ID NO: 96), while instating two new GEs that span the framework two and HCDR2 CLEWMGIINP (SEQ ID NO: 97)' and 'MGI-INPSGG' (SEQ ID NO: 98)). Clone MH7 was therefore left with only a single potential foreign epitope in its VH domain (Table 7).

Importantly, it was observed that the extensive mutagenesis performed in the LCDR1, which removed development liability motifs in several leads (Table 4) did not generate any T cell epitope risk motifs. Multiple foreign epitopes found in the h224G11 VL sequence were also eliminated by germlining mutations found in the CDRs of lead clones. For example, a HAF peptide 'IYRASTRES' (SEQ ID NO: 92) found in the LCDR2 of h224G11 was found to be ablated in all lead clones that contained the mutation S>T at position 9 (Table 4). Similarly, a LAF peptide motif in the LCDR3 of h224G11 was ablated in the LCDR3 sequences 'QQYGSE-PLT' (SEQ ID NO: 53) and 'QQSKESPLT' (SEQ ID NO: 47), as found in multiple library-derived and designer clones (Table 4). As the clones MH7 and 07A01 both contained multiple CDR sequences with reduced immunogenic potential, and demonstrated maintained epitope specificity and affinity improvements over h224G11 (Table 5, FIG. 4), the findings above allowed the design of second-generation maximally deimmunised clones MH7-1, MH7-2 and MH7-3 (Table 7, Table 8). Clone MH7-3 not only improved the predicted immunogenicity of clone MH7, but also removed the final CDR amino acid liability motif (a deamidation risk site), by converting the amino acids 'NS' at positions 11 and 12 of LCDR1 with the motif 'QS' (Table 8).

Analyses of Second-Generation Designer Clones

Figure 6:
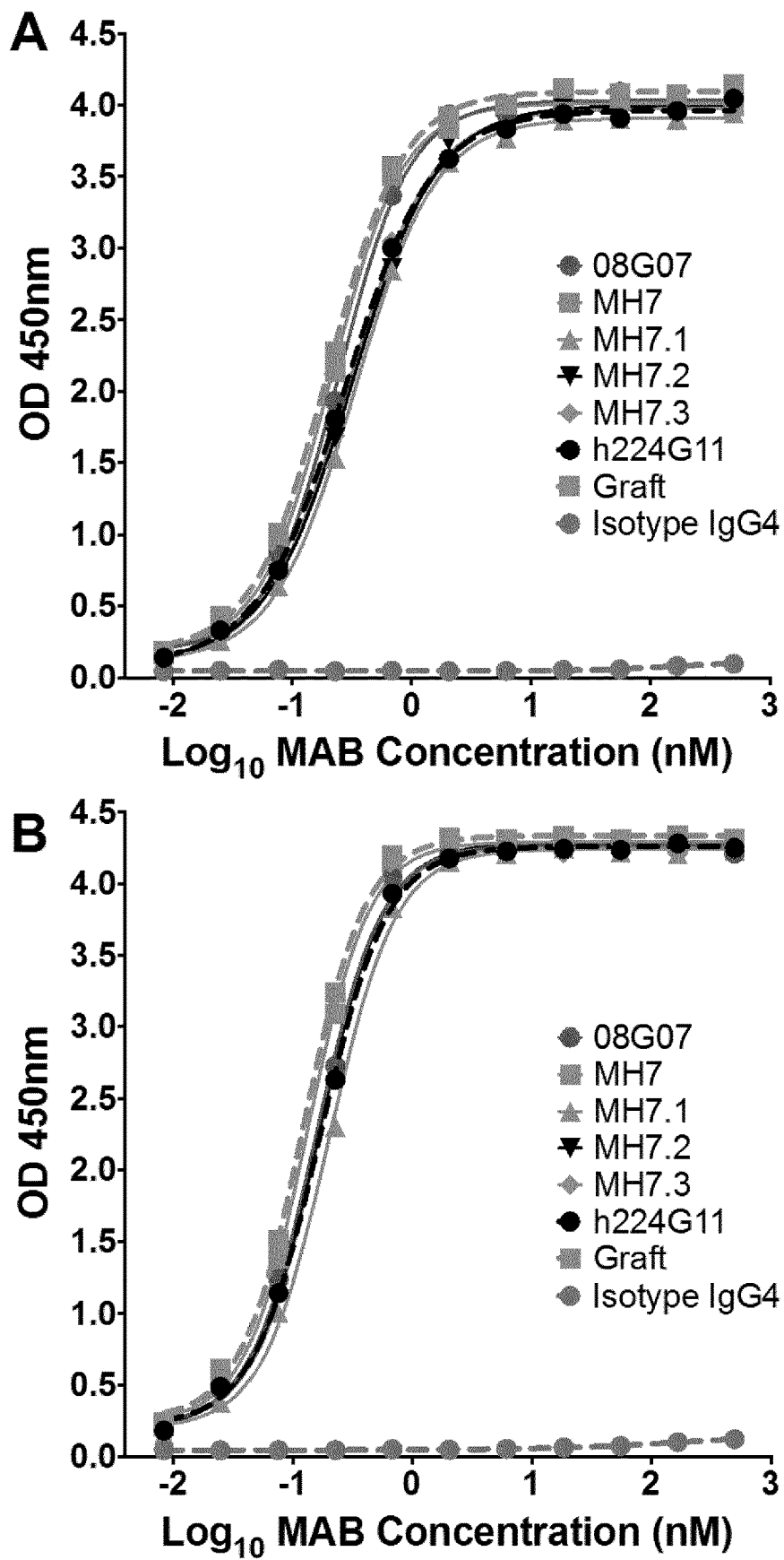
FIG. 6A-FIG. 6B. Direct titration ELISA for IgG binding to human and cyno C-MET-Fc proteins. Humanized h224G11, Grafted clone (Graft) and clones 08G07, MH7, MH7-1, MH7-2, MH7-3 in human IgG4(S228P) format were titrated (in nM) in a direct binding ELISA against human (FIG. 6A) and cyno (FIG. 6B) C-MET-Fc proteins. All clones other than Isotype IgG4 control demonstrated binding activity against both orthologs of C-MET, with approximately equivalent or improved human and cyno C-MET binding.

Clones MH7-1, MH7-2 and MH7-3 were readily expressed and purified as IgG4(S22P) and were then tested for binding to human and cyno C-MET-Fc in direct titration ELISA format (FIG. 6A, 6B). This analysis demonstrated that all 3 clones retained full binding activity for human and cyno C-MET that was equivalent to, or improved over, the h224G11, Grafted, MH7 and 08G07 IgG4(S228P) proteins.

Figure 7:
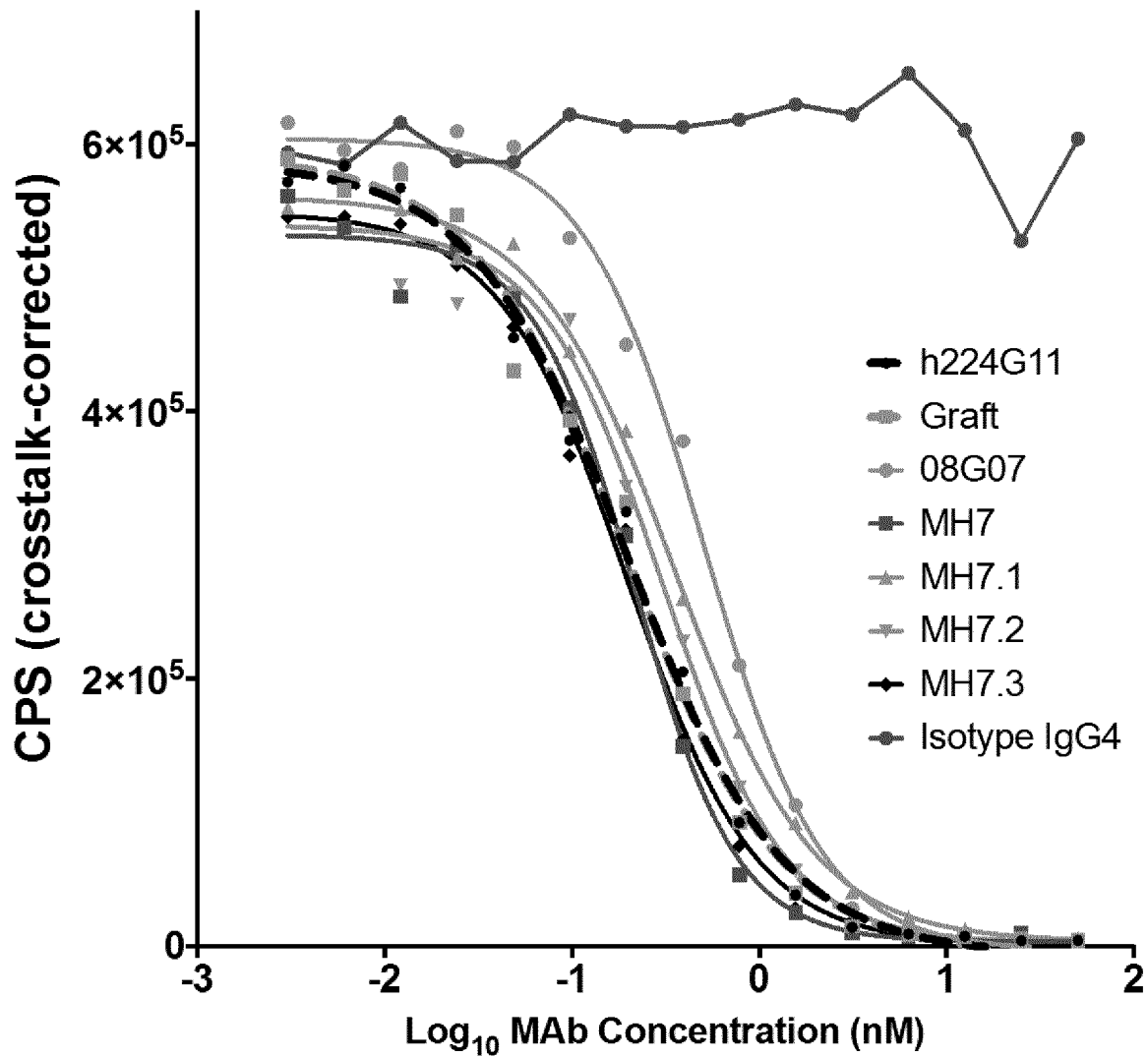
FIG. 7. Epitope competition analysis of IgG4(S228P) proteins in Alphascreen. Anti-Humanized h224G11, Grafted clone (Graft) and clones 08G07, MH7, MH7-1, MH7-2, MH7-3 in human IgG4(S228P) format were titrated (in nM) in an epitope competition assay using Alphascreen technology. In this assay, library-derived and designer IgGs were analysed for their retention of the parental 224G11 epitope by competing for 224G11 IgG4(S228P) binding to human C-MET protein, in solution. All clones analysed showed strong, concentration-dependent neutralisation of 224G11 binding to C-MET.

The Alphascreen assay, as described above, was then used to allow the testing of IgGs for epitope competition with h224G11 IgG binding to biotinylated monomeric human C-MET. This analysis demonstrated that all 3 clones retained full epitope reactivity that was equivalent to h224G11 (FIG. 7).

Figure 8A:
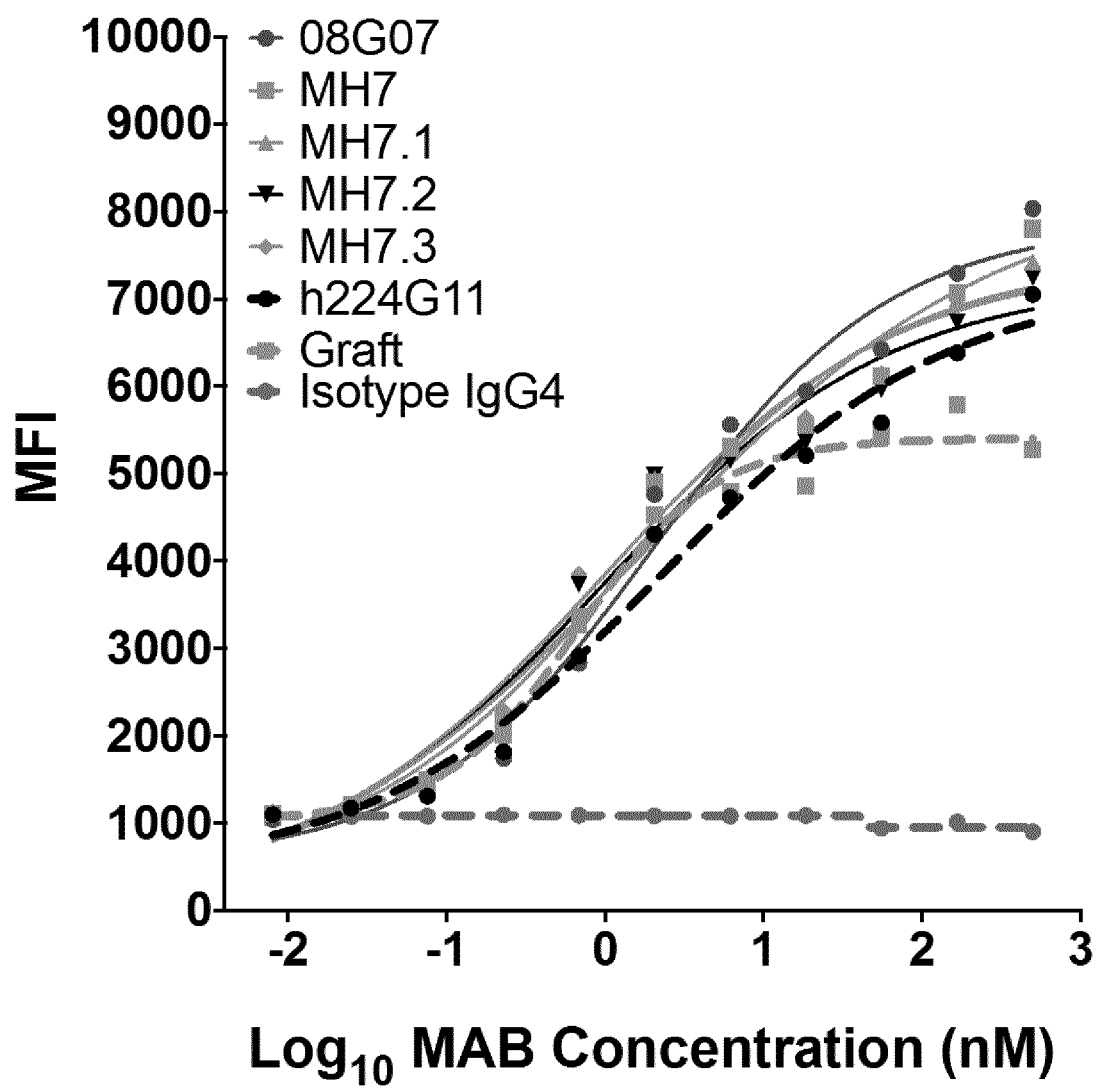
FIG. 8A-FIG. 8C. Flow cytometric binding to human and cyno C-MET+CHO-K1 cells for library-derived and primary designer leads. Humanized h224G11, Grafted clone (Graft) and clones 08G07, MH7, MH7-1, MH7-2, MH7-3 in human IgG4(S228P) format were were examined for specific binding on human C-MET-transfected (FIG. 8A), cyno C-MET-transfected (FIG. 8B) and untransfected (FIG. 8C) CHO-K1 cells. IgGs were tested at concentrations ranging from 500-0.08 nM. Concentration-dependent binding was observed against both human and cyno cell lines for all C-MET-specific antibodies but not isotype control IgG4.
Figure 8B:
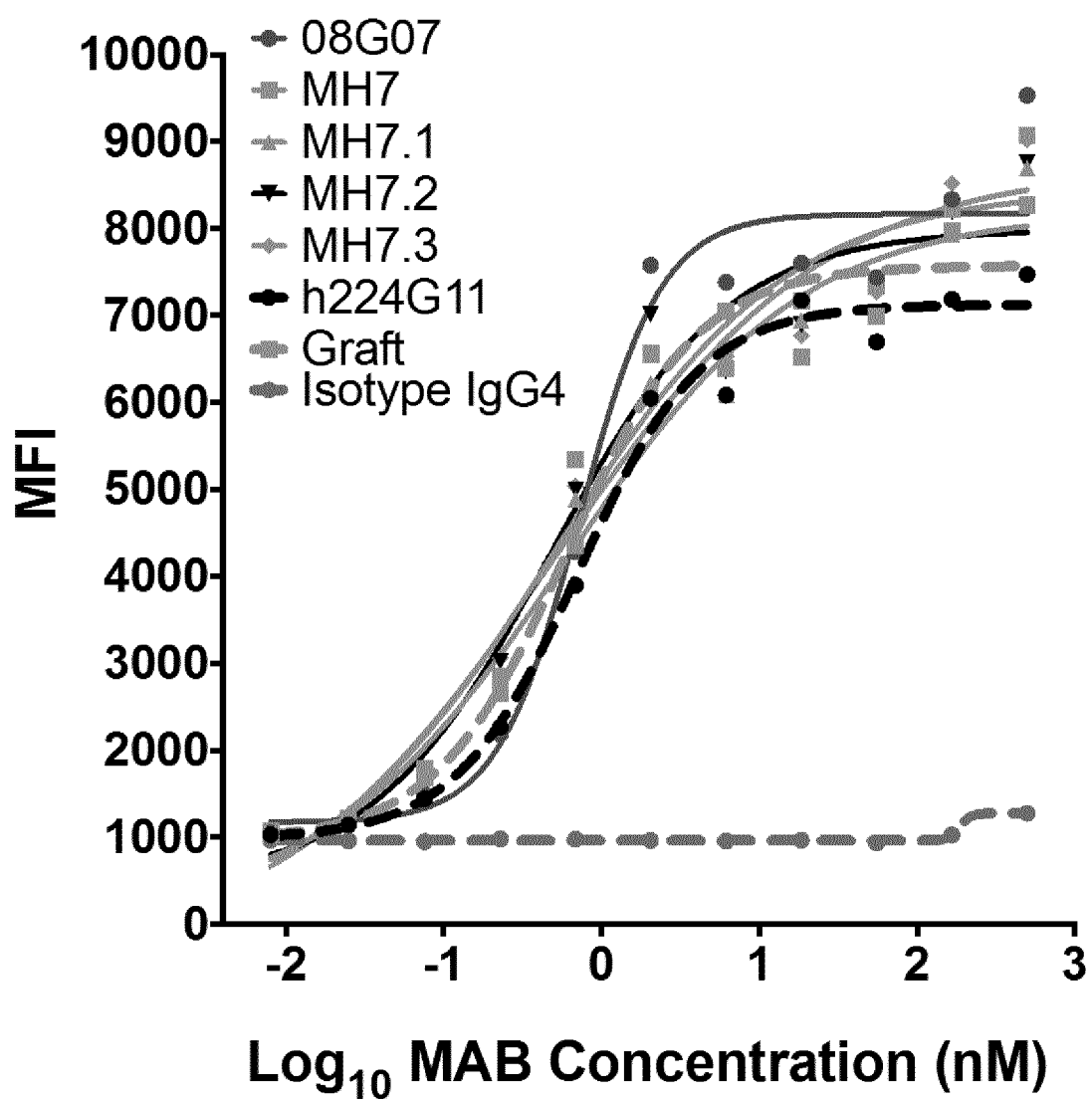
Figure 8C:
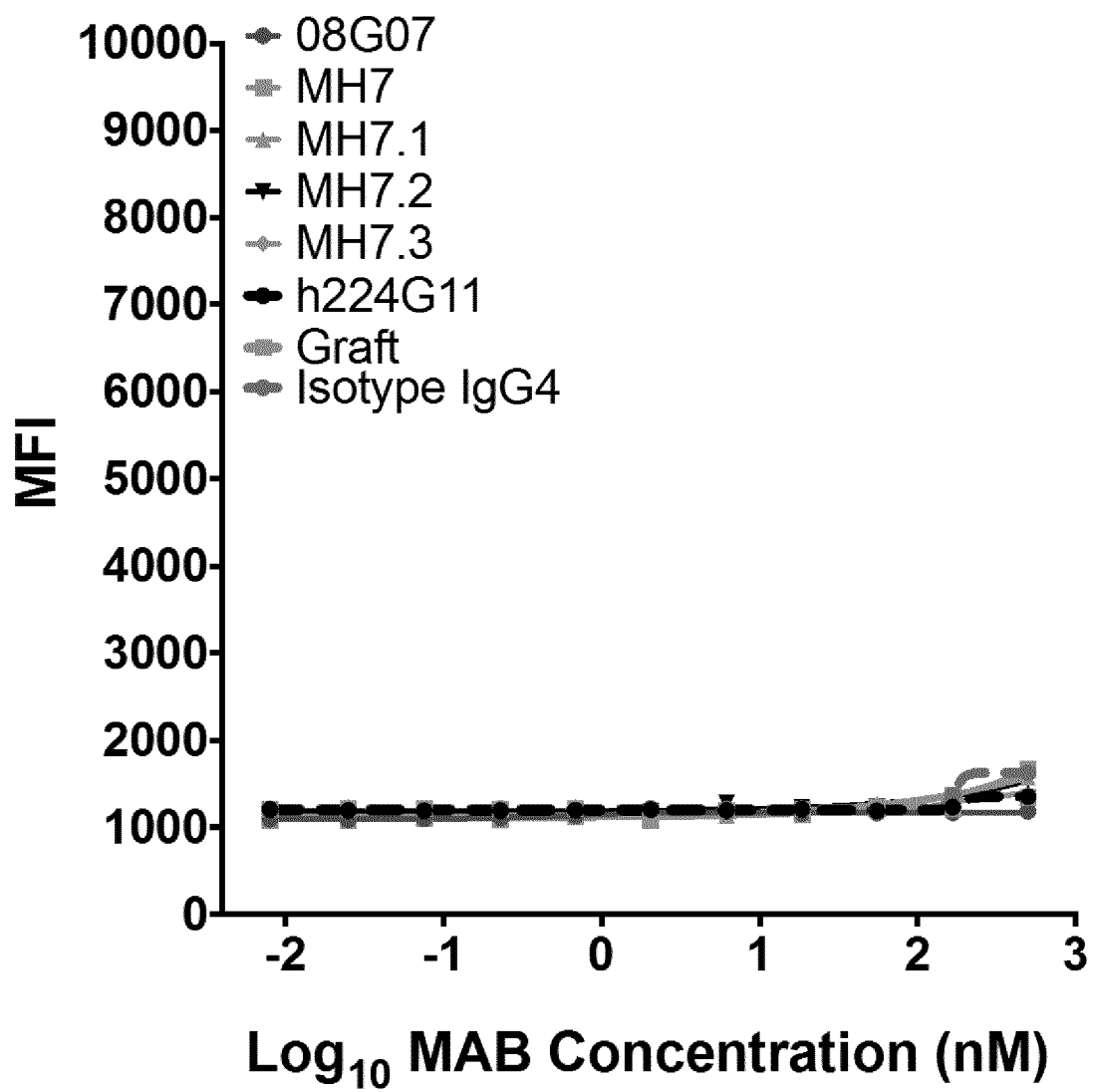
Figure 9:
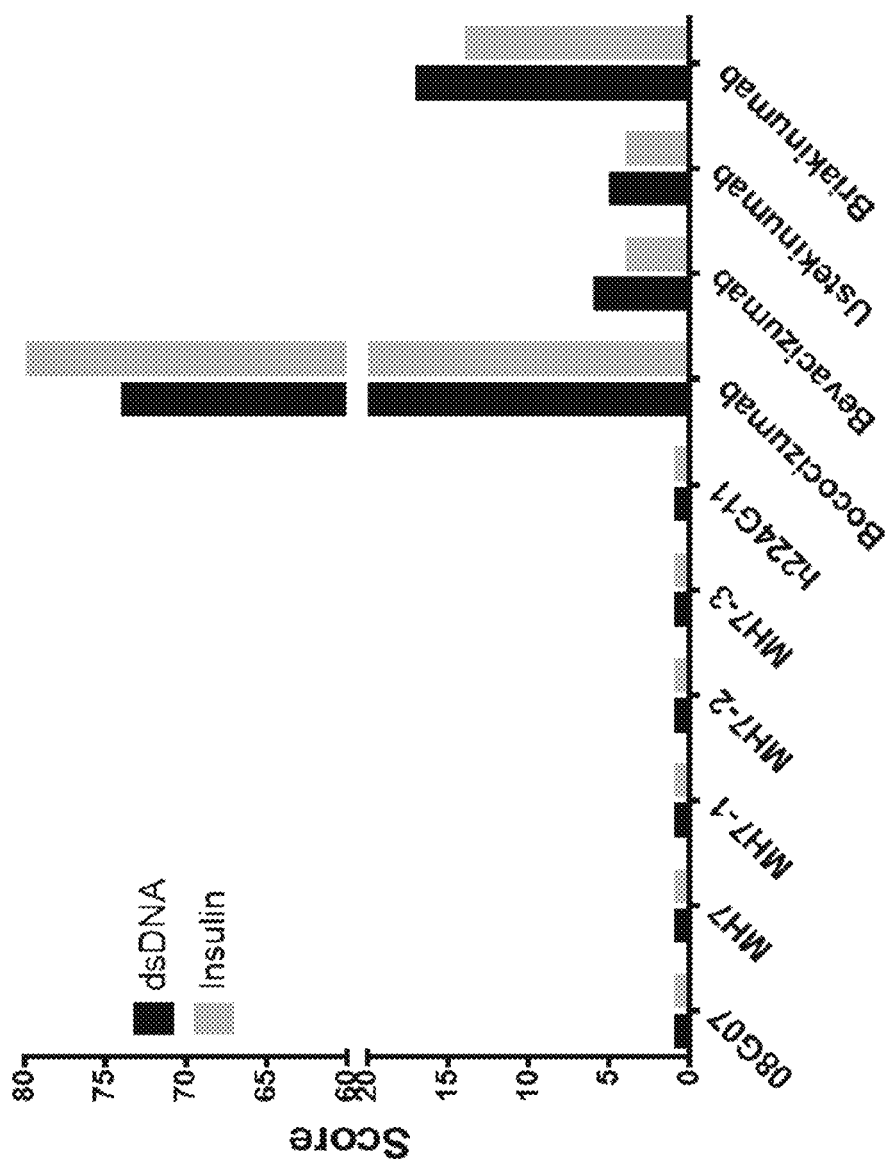
FIG. 9. Development risk ELISAs. Humanized h224G11 and clones 08G07, MH7, MH7-1, MH7-2, MH7-3 in human IgG4(S228P) format were examined for nonspecific binding to the negatively charged biomolecules Insulin and double-stranded DNA (dsDNA). All lead clones demonstrated binding scores of 1.0, significantly lower than either of the negative control IgG1 Ustekinumab and Bevacizumab analogs. Strong off-target binding to insulin or dsDNA, as observed for Bococizumab and Briakinumab analogues, has been shown to be a high-risk indicator of poor pharmacokinetics of therapeutic antibodies.

In flow cytometric analyses, clones 08G07, MH7, MH7-1, MH7-2, MH7-3, h224G11, Grafted, and an isotype control IgG were each tested in IgG4(S228P) format, over a concentration range of 500-0.08 nM for binding to human (FIG. 8A), cyno (FIG. 8B) and untransfected (FIG. 8C) CHO-K1 cells. All IgGs other than the isotype control showed concentration-dependent binding to human and cyno C-MET+ cells, equivalent to, or improved over h224G11, with a maximum MFI in each case being >10-fold higher than observed background signals for Isotype IgG4. No binding was observed for any IgG against untransfected cells.

In polyreactivity ELISAs designed to identify the risk of poor PK in humans (Avery et al. Mabs, 2018), clones 08G07, MH7, MH7-1, MH7-2, MH7-3 and h224G11 all demonstrated baseline signals (all reactivity scores 1.0) against both insulin and dsDNA. These signals were lower than those of the negative control, clinically-approved antibodies Bevacizumab and Ustekinumab (scores 4.0-6.0). Positive control antibodies Briakinumab and Bococizumab, which suffered from short PK in humans, both exhibited strong positive signals >15.0.

In Biacore® analyses of binding affinity to the purified recombinant ectodomain, clones MH7-1, MH7-2, MH7-3 all retained high binding affinity to both human and cyno orthologs of C-MET (Table 9).

Charge Variant Analysis

Figure 10A:
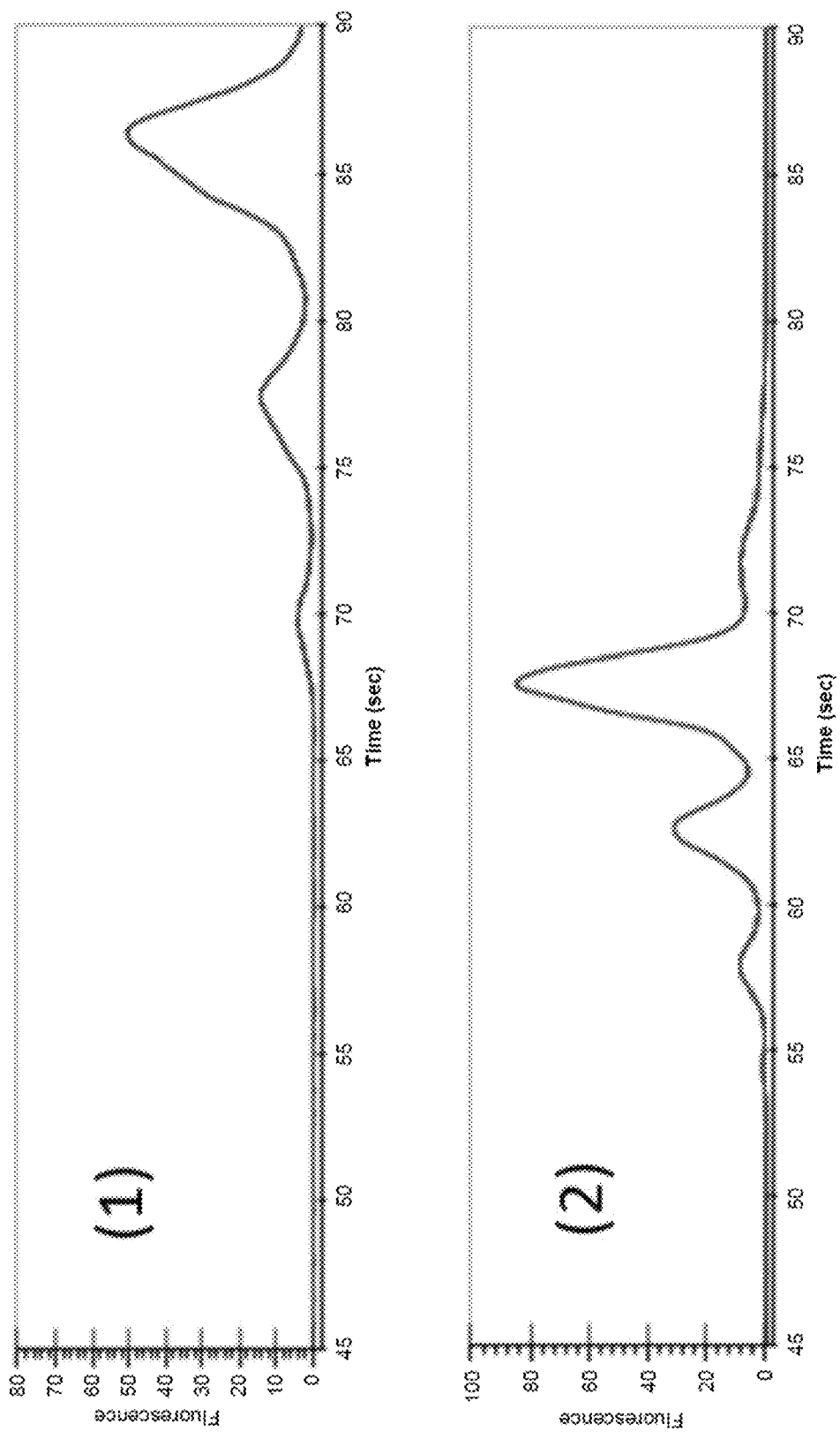
FIG. 10A-FIG. 10C. Charge variant profiles of IgGs. Protein Charge Variant Assay data for the following antibodies in IgG4(S228P) form are shown.
Figure 10B:
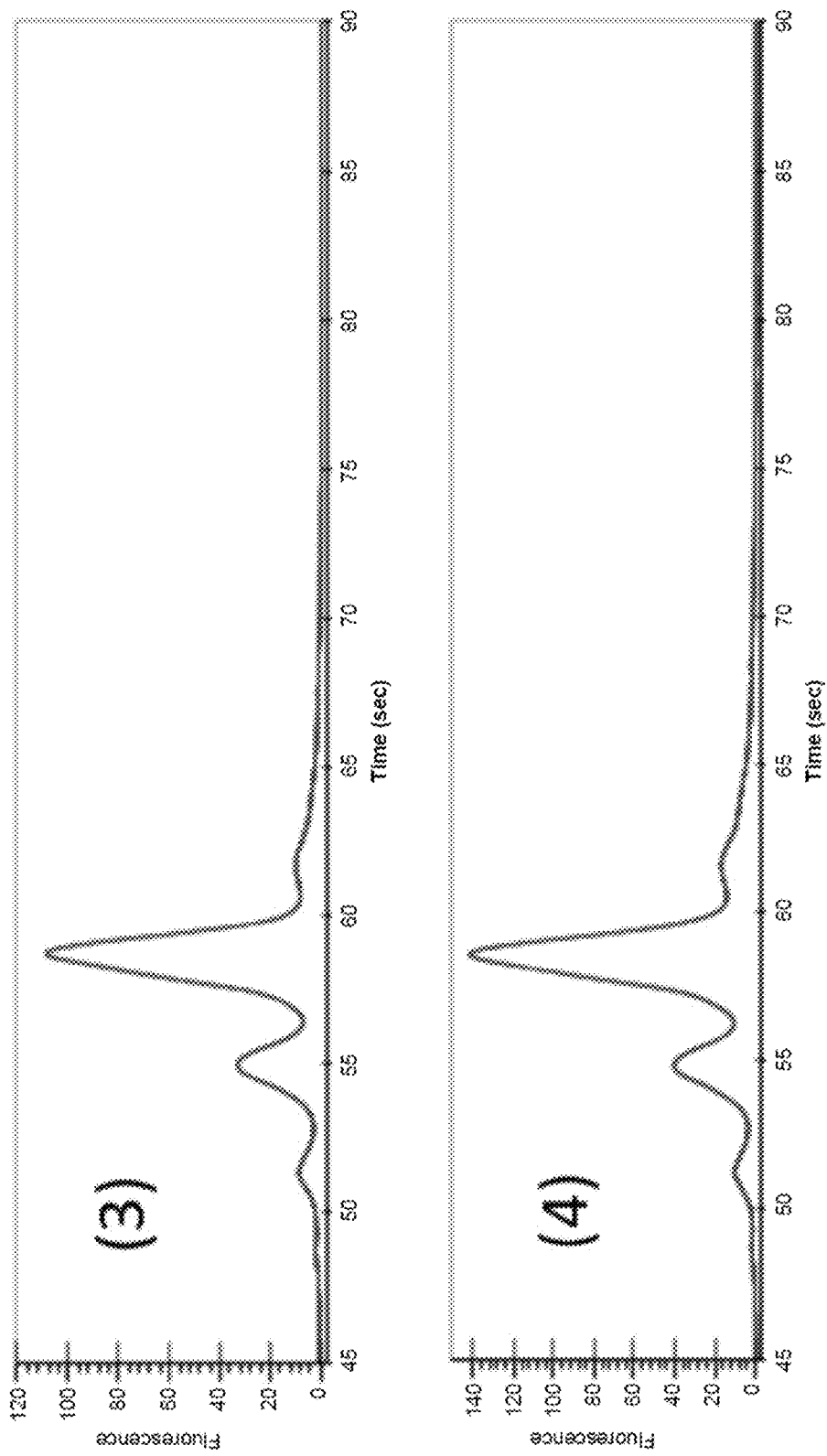
Figure 10C:
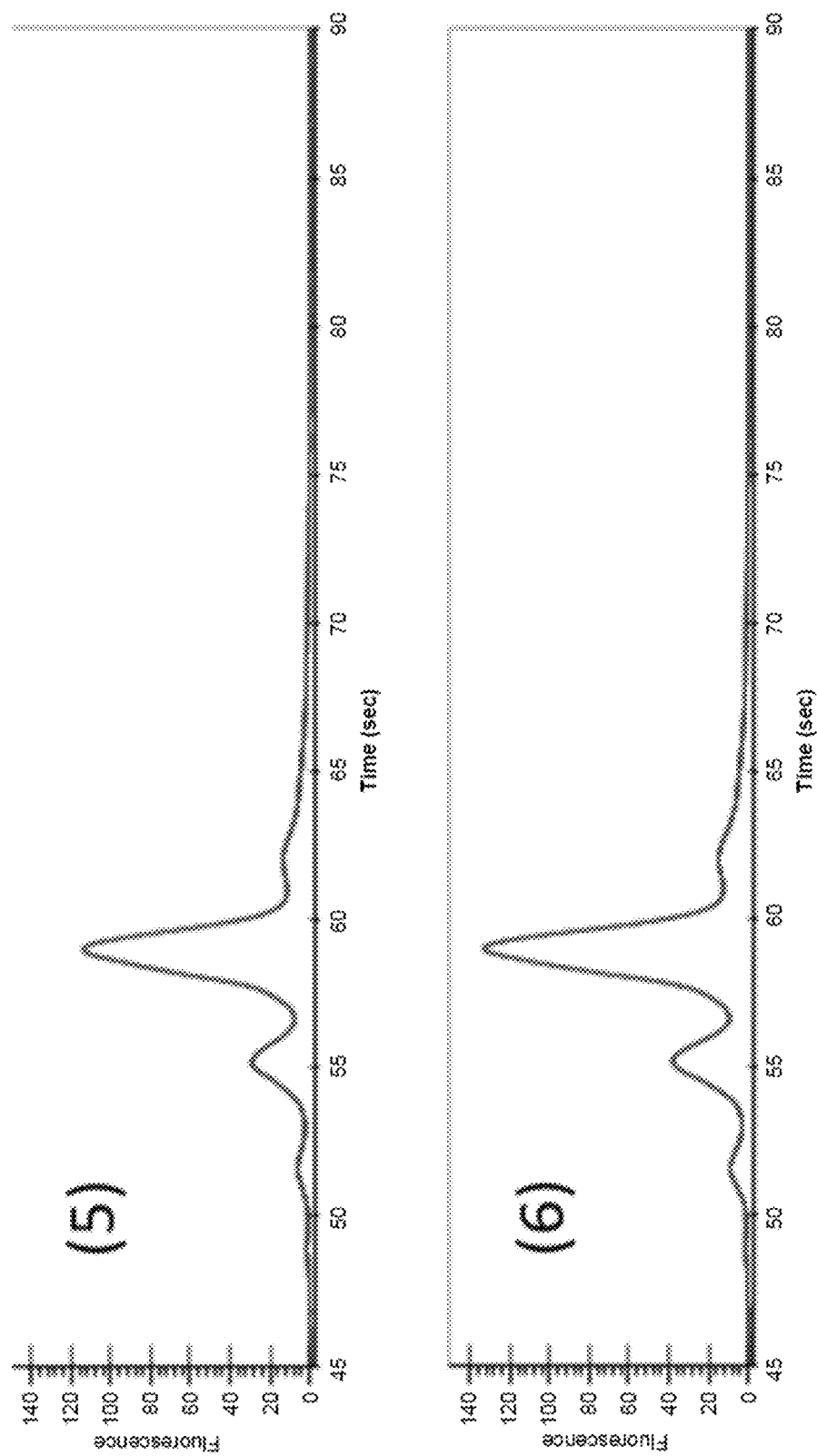

Charge heterogeneity analysis is important in the characterisation of monoclonal antibodies because it provides information about product quality, uniformity and stability. Heterogeneity in recombinant proteins can be caused by enzymatic post-translational modifications (such as glycosylation, lysine truncation) or chemical modifications during purification and storage (such as oxidation or deamidation). Protein Charge Variant Assays such as LabChip® GXII Touch HT allow identification of basic and acidic protein variants relative to the main peak. This microfluidics chip technology electrophoretically separates protein charge variants after fluorescent labelling. The charge variant profiles of six antibodies in IgG4(S228P) form (08G07, MH7, MH7-1, MH7-2, MH7-3 and h224G11), analysed using this method, are depicted in FIG. 10. Unusually for a human IgG, the IgG4 form of h224G11 did not achieve full resolution in the available assay, due to it having a low apparent pI (manufacturer's recommended pI range of main isoform being 7.0 to 9.5), hence only 3 isoforms were identified when this protein was analysed as other, more acidic isoforms (pI<7.0) were likely impossible to resolve (FIG. 10). In contrast, clones 08G07, MH7, MH7-1, MH7-2, MH7-3 in IgG4 form displayed a more homogeneous, well resolved, less complex profile, with the main isoform counting for more than 60% of the total protein. The profiles shown in FIG. 10 suggest that the pI of the main isoform of h224G11 IgG4 is close to 7.0, while those of the clones 08G07, MH7, MH7-1, MH7-2 and MH7-3 IgG4s are all significantly higher, due to the reduction in number of negatively-charged residues in their primary CDR sequence in comparison to h224G11. In addition, the lowered content of deamidation risk motifs in the CDRs of clones 08G07, MH7, MH7-1, MH7-2 and MH7-3, in comparison with h224G11, may further reduce the presence of −ve charge (acidic) variants. This unexpected marked increase in the pI of the lead clones in IgG4 form, over h224G11, is potentially highly beneficial in clinical formulation. The pH of buffers used for antibody liquid formulations is preferred to be at acidic pH, such as pH6, to minimise the progression of e.g. deamidation events during storage. To minimise the risk of antibody aggregation in solution, it is therefore beneficial for the final antibody to have a main functional pI in the basic range, above pH7.4 and preferably above pH8.0.

Figure 11:
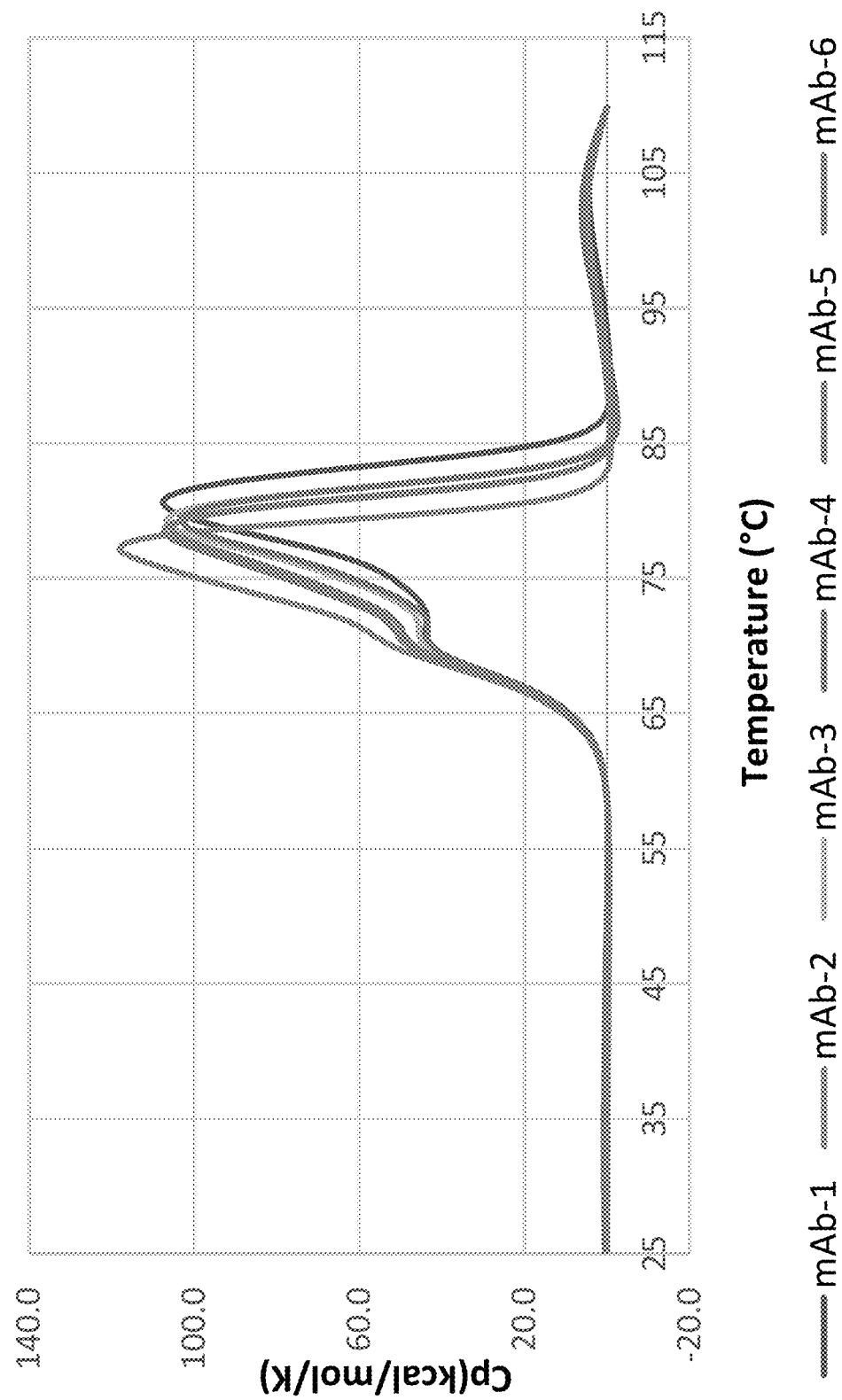
FIG. 11. Differential Scanning calorimetry (DSC) of IgGs. DSC assay data for the following antibodies in IgG4 (S228P) form are shown: (mAb-1) h224G11, (mAb-2) 08G07, (mAb-3) MH7, (mAb-4) MH7-1, (mAb-5) MH7-2 and (mAb-6) MH7-3.

In addition, the antibodies 08G07, MH7, MH7-1, MH7-2, MH7-3 and h224G11 in IgG4(S228P) form were all analysed in a DSC assay to establish their thermal stability, a surrogate measurement for overall physical stability of the molecule (FIG. 11). All 6 IgGs were found to have highly similar, thermally stable Fab structures, with Tm values spanning a narrow range (77.2-80.6° C.).

Figure 12:
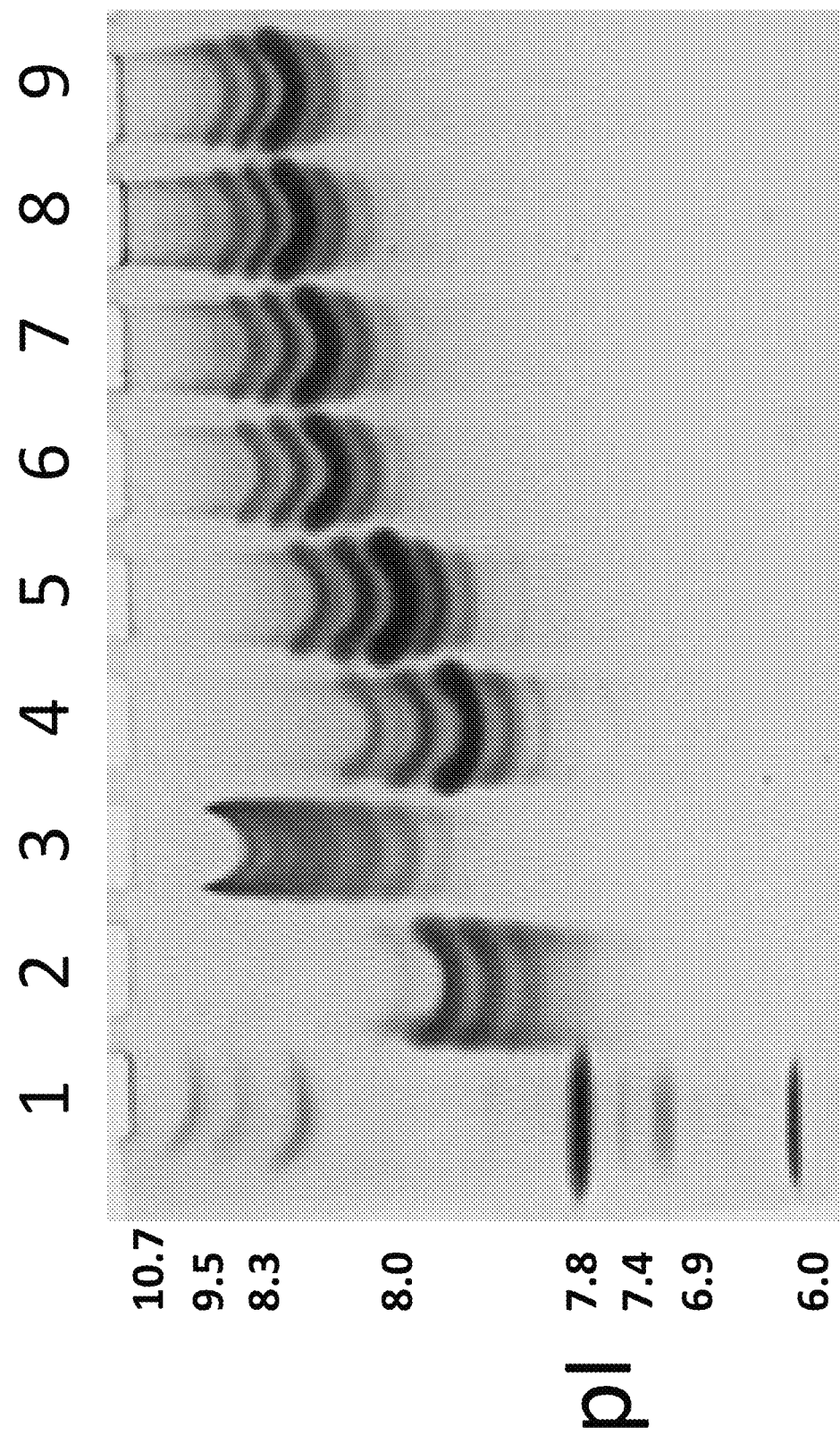
FIG. 12. Isoelectric Focusing analysis. IEF Assay data for the following protein samples are shown: (1) IEF Marker SERVALYT™ 3-10, (2) Brentuximab IgG1, (3) Infiximab IgG1, (4) h224G11 IgG4(S228P), (5) 08G07 IgG4(S228P), (6) MH7 IgG4(S228P), (7) MH7-1 IgG4(S228P), (8) MH7-2 IgG4(S228P) and (9) MH7-3 IgG4(S228P).

As the full spread of charge isoforms of h224G11 could not be resolved via the charge variant assay, the pI characteristics of h224G11 and lead clones 08G07, MH7, MH7-1, MH7-2 and MH7-3 were examined experimentally via Isoelectric Focusing (IEF). Control IgG1 proteins Brentuximab and Infliximab were also included and demonstrated the expected profiles (FIG. 12). In this analysis, the findings of the charge variant assay were confirmed, with clone h224G11 exhibiting a significantly lower pI range than observed for 08G07, MH7, MH7-1, MH7-2 and MH7-3 (FIG. 12). For clone h224G11, it's IgG4(S228P) protein exhibited visible charge isoforms (bands on IEF) across the pI range 7.4 to ~8.2. Charge isoforms in the range of 7.4 are not only a formulation risk, but are also at risk of poor solubility in blood, as their pI is the same as mammalian blood pH, leading to possible in vivo aggregation in man. Lead clone 08G07, in contrast, exhibited visible isoforms from >7.8 to ~8.3 (FIG. 12). Importantly, clones MH7, MH7-1, MH7-2 and MH7-3 all improved yet further over 08G07. Indeed, the progressive improvement in pI of clones was evident up to clone MH7.3, which exhibited a range of visible isoforms from pI 8.0 to >8.3 with a main isoform at 8.3 (FIG. 12). As the v-domain framework regions of all lead clones are identical, this finding illustrated again that the application of non-human mutagenesis and removal of negatively charged residues and asparagines in the CDRs specifically drove not only reduced risk of post-translational modifications in CDR loops, but significantly improved the overall true pI values of lead clones, improving the formulation quality and potential in vivo performance of all clones 08G07, MH7, MH7-1, MH7-2 and MH7-3.

The combined analyses outlined herein demonstrated that, surprisingly, deep sampling of both germline and non-germline amino acids in the CDRs of these antibodies allowed the simultaneous optimisation of both immunogenicity risk and chemical stability risks in the final molecules, without significantly compromising the potency or biophysical stability of the final molecules.

Although the present invention has been described with reference to preferred or exemplary embodiments, those skilled in the art will recognize that various modifications and variations to the same can be accomplished without departing from the spirit and scope of the present invention and that such modifications are clearly contemplated herein. No limitation with respect to the specific embodiments disclosed herein and set forth in the appended claims is intended nor should any be inferred.

All documents, or portions of documents, cited herein, including but not limited to patents, patent applications, articles, books, and treatises, are hereby expressly incorporated by reference in their entirety for any purpose. In the event that one or more of the incorporated documents or portions of documents define a term that contradicts that term's definition in the application, the definition that appears in this application controls. However, mention of any reference, article, publication, patent, patent publication, and patent application cited herein is not, and should not be taken as an acknowledgment, or any form of suggestion, that they constitute valid prior art or form part of the common general knowledge in any country in the world.

TABLE 1

Amino acid sequences of 224G11 anti-C-MET CDRs as defined here ("Unified" scheme) in comparison to alternative definitions.

| Scheme | HCDR1 | HCDR2 | HCDR3 | LCDR1 | LCDR2 | LCDR3 |
|---|---|---|---|---|---|---|
| Unified | GYIFTAYTMH (SEQ ID NO: 100) | MGWIKPNNGLANYAQKFQG (SEQ ID NO: 106) | SEITTEFDY (SEQ ID NO: 113) | KSSESVDSYANSFLH (SEQ ID NO: 117) | RASTRES (SEQ ID NO: 121) | QQSKEDPLT (SEQ ID NO: 123) |
| Kabat | AYTMH (SEQ ID NO: 101) | WIKPNNGLANYAQKFQG (SEQ ID NO: 107) | SEITTEFDY (SEQ ID NO: 113) | KSSESVDSYANSFLH (SEQ ID NO: 117) | RASTRES (SEQ ID NO: 121) | QQSKEDPLT (SEQ ID NO: 123) |
| Chotia | GYIFTAY (SEQ ID NO: 102) | KPNNGL (SEQ ID NO: 108) | SEITTEFDY (SEQ ID NO: 113) | KSSESVDSYANSFLH (SEQ ID NO: 117) | RASTRES (SEQ ID NO: 121) | QQSKEDPLT (SEQ ID NO: 123) |
| IMGT | GYIFTAYT (SEQ ID NO: 103) | IKPNNGLA (SEQ ID NO: 109) | ARSEITTEFDY (SEQ ID NO: 114) | ESVDSYANSF (SEQ ID NO: 118) | RAS (SEQ ID NO: ) | QQSKEDPLT (SEQ ID NO: 123) |
| AHo | ASGYIFTAYTMH (SEQ ID NO: 104) | IKPNNGLANYAQKFQG (SEQ ID NO: 110) | SEITTEFD (SEQ ID NO: 115) | SSESVDSYANSF (SEQ ID NO: 119) | RASTRES (SEQ ID NO: 121) | SKEDPL (SEQ ID NO: 124) |
| AbM | GYIFTAYTMH (SEQ ID NO: 100) | WIKPNNGLAN (SEQ ID NO: 111) | SEITTEFDY (SEQ ID NO: 113) | KSSESVDSYANSFLH (SEQ ID NO: 117) | RASTRES (SEQ ID NO: 121) | QQSKEDPLT (SEQ ID NO: 123) |
| Contact | TAYTMH (SEQ ID NO: 105) | MGWIKPNNGLAN (SEQ ID NO: 112) | ARSEITTEFD (SEQ ID NO: 116) | VDSYANSFLHWY (SEQ ID NO: 120) | LLIYRASTRE (SEQ ID NO: 122) | QQSKEDPL (SEQ ID NO: 125) |

TABLE 2

Amino acid sequence of h224G11 anti-C-MET v-domains and human germline CDR grafts.

| V DOMAIN | Human germline[1] | Amino acid sequence[2] |
|---|---|---|
| h224G11-VH | IGHV1-2 | QVQLVQSGAEVKKPGASVKVSCKASGYIFTAYTMHWVRQAPGQGLEWMGWIKPNNGLANYAQKFQGRVTMTRDTSIS TAYMELSRLRSDDTAVYYCARSEITTEFDYWGQGTLVTVSS (SEQ ID NO: 126) |
| VH graft | IGHV1-46[3] | QVQLVQSGAEVKKPGASVKVSCKASGYIFTAYTMHWVRQAPGQGLEWMGWIKPNNGLANYAQKFQGRVTMTRDTSTS TVYMELSSLRSEDTAVYYCARSEITTEFDYWGQGTLVTVSS (SEQ ID NO: 127) |
| h224G11-VL | IGKV4-1 | DIVMTQSPDSLAVSLGERATINCKSSESVDSYANSFLHWYQQKPGQPPKLLIYRASTRESGVPDRFSGSGSGTDFTL TISSLQAEDVAVYYCQQSKEDPLTFGGGTKVEIK (SEQ ID NO: 128) |
| VL graft | IGKV3-20[3] | EIVLTQSPGTLSLSPGERATLSCRASQSVDSYANSFLHWYQQKPGQAPRLLIYRASTRESGIPDRFSGSGSGTDFTL TISRLEPEDFAVYYCQQSKEDPLTFGGGTKVEIK (SEQ ID NO: 129) |

[1] Human germline definitions used for grafting, based on IMGT system.
[2] CDR residues are in bold and underlined. As noted above, the "Unified" CDR definitions used in this manuscript are an expanded definition in comparison to the classical Kabat definition. Each sequence above shows the framework regions (FRs) and the CDRs in the following order: FR1-CDR1-FR2-CDR2-FR3-CDR3-FR4.
[3] Grafts are fully germline in the framework regions, used as the template for CDR mutant library construction.

TABLE 3

Amino acid sequences of unique CDRs from 131 unique anti-C-MET v-domains.

| LCDR1 | LCDR2 | LCDR3 | HCDR1 | HCDR2 | HCDR2 | HCDR3 |
|---|---|---|---|---|---|---|
| RASQSVDSYANSFLA (SEQ ID NO: 130) | AASTRES (SEQ ID NO: 143) | QQSGEDPLTF (SEQ ID NO: 150) | GYIFTAYSMH (SEQ ID NO: 83) | MGIIKPNGGLASYAQKFQG (SEQ ID NO: 174) | MGIIKPSGGSTNYAQKFQG (SEQ ID NO: 193) | AEITTEFDY (SEQ ID NO: 85) |
| RASQSVDSYANSFLH (SEQ ID NO: 131) | AGSTRES (SEQ ID NO: 144) | QQSGEPLTF (SEQ ID NO: 151) | GYIFTAYYMH (SEQ ID NO: 168) | MGIIKPNGGSTNYAQKFQG (SEQ ID NO: 175) | MGIIKPSNGASYAQKFQG (SEQ ID NO: 215) | BEITTEFDY (SEQ ID NO: 80) |
| RASQSVDSYANSYLA (SEQ ID NO: 132) | AGSTRET (SEQ ID NO: 145) | QQSGESPLTF (SEQ ID NO: 152) | GYIFTSYSMH (SEQ ID NO: 43) | MGIIKPNNGSTSYAQKFQG (SEQ ID NO: 176) | MGIIKPSGGLANYAQKFQG (SEQ ID NO: 216) | HEITTEFDY (SEQ ID NO: 238) |
| RASQSVDSYANSYLH (SEQ ID NO: 51) | RASSRES (SEQ ID NO: 146) | QQSGSDPLTF (SEQ ID NO: 153) | GYIFTSYTMH (SEQ ID NO: 48) | MGIIKPSNGSTNYAQKFQG (SEQ ID NO: 84) | MGIIKPSNGSASYAQKFQG (SEQ ID NO: 217) | MEITTEFDY (SEQ ID NO: 239) |
| RASQSVDSYAQSFLH (SEQ ID NO: 133) | RASSRET (SEQ ID NO: 147) | QQSGSEPLTF (SEQ ID NO: 154) | GYIFTSYYMH (SEQ ID NO: 169) | MGIIKPSNGSTSYAQKFQG (SEQ ID NO: 177) | MGIINPNGGLASYAQKFQG (SEQ ID NO: 218) | QEITTEFDI (SEQ ID NO: 45) |
| RASQSVDSYAQSYLA (SEQ ID NO: 134) | RASTRET (SEQ ID NO: 77) | QQSGSRPLTF (SEQ ID NO: 155) | GYTFTAYSMH (SEQ ID NO: 170) | MGIINPNGGSASYAQKFQG (SEQ ID NO: 178) | MGIINPNGGSASYAQKFQG (SEQ ID NO: 219) | QEITTEFDY (SEQ ID NO: 36) |
| RASQSVDSYAQSYLH (SEQ ID NO: 135) | RGSSRES (SEQ ID NO: 148) | QQSGSSPLTF (SEQ ID NO: 156) | GYTFTAYTMH (SEQ ID NO: 171) | MGIINPSGGLANYAQKFQG (SEQ ID NO: 179) | MGIINPNNGLANYAQKFQG (SEQ ID NO: 220) | QEITTELDY (SEQ ID NO: 240) |
| RASQSVESYANSFLA (SEQ ID NO: 136) | RGSSRET (SEQ ID NO: 149) | QQSKEEPLTF (SEQ ID NO: 157) | GYTFTAYYMH (SEQ ID NO: 172) | MGIINPSGGSTNYAQKFQG (SEQ ID NO: 180) | MGIINPSGGLASYAQKFQG (SEQ ID NO: 221) | SEITTDFDY (SEQ ID NO: 55) |
| RASQSVESYANSYLA (SEQ ID NO: 137) | RGSTRES (SEQ ID NO: 38) | QQSKESPLTF (SEQ ID NO: 158) | GYTFTSYSMH (SEQ ID NO: 78) | MGIINPSGGSTSYAQKFQG (SEQ ID NO: 35) | MGIINPSGGLASYAQKFQG (SEQ ID NO: 222) | SEITTEEDY (SEQ ID NO: 241) |
| RASQSVESYANSYLH (SEQ ID NO: 52) | RGSTRET (SEQ ID NO: 56) | QQSKSDPLTF (SEQ ID NO: 159) | GYTFTSYTMH (SEQ ID NO: 34) | MGWIKPNGGSTNYAQKFQG (SEQ ID NO: 181) | MGIINPSNGLANYAQKFQG (SEQ ID NO: 223) | SEITTEFDA (SEQ ID NO: 242) |
| RASQSVESYAQSFLH (SEQ ID NO: 138) | | QQSKSEPLTF (SEQ ID NO: 160) | GYTFTSYYMH (SEQ ID NO: 173) | MGWIKPNNGSASYAQKFQG (SEQ ID NO: 86) | MGIINPSNGSTNYAQKFQG (SEQ ID NO: 224) | SEITTEFDE (SEQ ID NO: 243) |
| RASQSVESYAQSYLH (SEQ ID NO: 46) | | QQSKSSPLTF (SEQ ID NO: 161) | | MGWIKPSGGSTYAQKFQG (SEQ ID NO: 182) | MGWIKPNGGLTSYAQKFQG (SEQ ID NO: 225) | SEITTEFDF (SEQ ID NO: 244) |
| | | | | | MGWIKPNNGLTSYAQKFQG (SEQ ID NO: 226) | |

TABLE 3-continued

Amino acid sequences of unique CDRs from 131 unique anti-C-MET v-domains.

| LCDR1 | LCDR2 | LCDR3 | HCDR1 | HCDR2 | HCDR2 | HCDR2 | HCDR3 |
|---|---|---|---|---|---|---|---|
| RASQSVSSYANSFLH (SEQ ID NO: 139) | | QQYGSDPLTF (SEQ ID NO: 162) | | MGWIKPSNGLASYAQKFQG (SEQ ID NO: 183) | MGWIKPNGGLANYAQKFQG (SEQ ID NO: 205) | MGWIKPNNGSANYAQKFQG (SEQ ID NO: 227) | SEITTEFDI (SEQ ID NO: 245) |
| RASQSVSSYANSYLA (SEQ ID NO: 140) | | QQYGSEPLTF (SEQ ID NO: 163) | | MGWIKPSNGSANYAQKFQG (SEQ ID NO: 184) | MGWIKPNGGSASYAQKFQG (SEQ ID NO: 206) | MGWIKPNNGSTNYAQKFQG (SEQ ID NO: 87) | SEITTEFDK (SEQ ID NO: 246) |
| RASQSVSSYANSYLH (SEQ ID NO: 37) | | QQYKEEPLTF (SEQ ID NO: 164) | | MGWIKPSNGSASYAQKFQG (SEQ ID NO: 185) | MGWIKPNGGSTSYAQKFQG (SEQ ID NO: 207) | MGWIKPSGGLTSYAQKFQG (SEQ ID NO: 228) | SEITTEFDL (SEQ ID NO: 247) |
| RASQSVSSYAQSFLA (SEQ ID NO: 141) | | QQYKESPLTF (SEQ ID NO: 165) | | MGWIKPSNGSTSYAQKFQG (SEQ ID NO: 186) | MGWIKPNNGSTSYAQKFQG (SEQ ID NO: 208) | MGWIKPSNGLTSYAQKFQG (SEQ ID NO: 229) | SEITTEFDM (SEQ ID NO: 248) |
| RASQSVSSYAQSFLH (SEQ ID NO: 142) | | QQYKSDPLTF (SEQ ID NO: 166) | | MGWINPNGGLTNYAQKFRG (SEQ ID NO: 79) | MGWINPNGGLASYAQKFQG (SEQ ID NO: 49) | MGWIKPSNGSTNYAQKFQG (SEQ ID NO: 230) | SEITTEFDQ (SEQ ID NO: 249) |
| RASQSVSSYAQSYLH (SEQ ID NO: 57) | | QQYKSSPLTF (SEQ ID NO: 167) | | MGWINPNGGLTSYAQKFQG (SEQ ID NO: 187) | MGWINPNGGLTNYAQKFQG (SEQ ID NO: 209) | MGWINPNGGSASYAQKFQG (SEQ ID NO: 231) | SEITTEFDS (SEQ ID NO: 250) |
| | | | | MGWINPNNGLANYAQKFQG (SEQ ID NO: 188) | MGWINPNGGSTNYAQKFQG (SEQ ID NO: 210) | MGWINPNNGLTNYAQKFQG (SEQ ID NO: 232) | SEITTEFDV (SEQ ID NO: 251) |
| | | | | MGWINPNNGLASYAQKFQG (SEQ ID NO: 189) | MGWINPNGGSTSYAQKFQG (SEQ ID NO: 42) | MGWINPNNGSANYAQKFQG (SEQ ID NO: 233) | SEITTEFDW (SEQ ID NO: 252) |
| | | | | MGWINPSGGLASYAQKFQG (SEQ ID NO: 190) | MGWINPNNGSTNYAQKFQG (SEQ ID NO: 81) | MGWINPNNGSASYAQKFQG (SEQ ID NO: 234) | SEITTELDY (SEQ ID NO: 253) |
| | | | | MGWINPSGGSASYAQKFQG (SEQ ID NO: 191) | MGWINPNNGSTSYAQKFQG (SEQ ID NO: 211) | MGWINPSGGLANYAQKFQG (SEQ ID NO: 54) | SEITTEQDY (SEQ ID NO: 50) |
| | | | | MGWINPSGGSTSYAQKFQG (SEQ ID NO: 40) | MGWINPSGGLTSYAQKFQG (SEQ ID NO: 212) | MGWINPSGGLTNYAQKFQG (SEQ ID NO: 235) | SEITTEWDY (SEQ ID NO: 254) |
| | | | | MGWINPSNGLANYAQKFQG (SEQ ID NO: 44) | MGWINPSGGANYAQKFQG (SEQ ID NO: 213) | MGWINPSNGSASYAQKFQG (SEQ ID NO: 236) | TEITTEFDY (SEQ ID NO: 88) |

TABLE 3-continued

Amino acid sequences of unique CDRs from 131 unique anti-C-MET v-domains.

| LCDR1 | LCDR2 | LCDR3 | HCDR1 | HCDR2 | HCDR2 | HCDR2 | HCDR3 |
|---|---|---|---|---|---|---|---|
| | | | | MGWINPSNGLTNYAQKFQG (SEQ ID NO: 192) | MGWINPSGGSTNYAQKFQG (SEQ ID NO: 214) | MGWINPSNGSTSYAQKFQG (SEQ ID NO: 237) | VEITTEFDL (SEQ ID NO: 255) |

TABLE 4

Amino acid sequences of CDRs of unique, library-derived and designer, human/cyno cross-reactive anti-C-MET IgGs.

| CLONE | LCDR1 | LCDR2 | LCDR3 | HCDR1 | HCDR2 | HCDR3 |
|---|---|---|---|---|---|---|
| 04F09 | RASQSVESYAQSYLH (SEQ ID NO: 46) | RGSTRES (SEQ ID NO: 38) | QQSKSDPLT (SEQ ID NO: 76) | GYIFTSYSMH (SEQ ID NO: 43) | MGWINPSNGLANYAQKFQG (SEQ ID NO: 44) | QEITTEFDI (SEQ ID NO: 45) |
| 07A01 | RASQSVDSYANSYLH (SEQ ID NO: 51) | RGSTRES (SEQ ID NO: 38) | QQSKESPLT (SEQ ID NO: 47) | GYIFTSYTMH (SEQ ID NO: 48) | MGWINPNGGLASYAQKFQG (SEQ ID NO: 49) | SEITTEQDY (SEQ ID NO: 50) |
| 09A12 | RASQSVSSYAQSYLH (SEQ ID NO: 57) | RASTRET (SEQ ID NO: 77) | QQSKESPLT (SEQ ID NO: 47) | GYTFTSYSMH (SEQ ID NO: 78) | MGWINPNGGLTNYAQKFRG (SEQ ID NO: 79) | EEITTEFDY (SEQ ID NO: 80) |
| 09B08 | RASQSVDSYANSYLH (SEQ ID NO: 51) | RGSTRES (SEQ ID NO: 38) | QQSKSDPLT (SEQ ID NO: 76) | GYTFTSYTMH (SEQ ID NO: 34) | MGWINPNNGSTNYAQKFQG (SEQ ID NO: 81) | SEITTDFDY (SEQ ID NO: 55) |
| 07C10 | RASQSVESYAQSYLH (SEQ ID NO: 46) | RGSTRES (SEQ ID NO: 38) | QQSKEEPLT (SEQ ID NO: 82) | GYIPTAYSMH (SEQ ID NO: 83) | MGIIKPSNGSTNYAQKFQG (SEQ ID NO: 84) | AEITTEFDY (SEQ ID NO: 85) |
| 09E04 | RASQSVDSYANSYLH (SEQ ID NO: 52) | RGSTRES (SEQ ID NO: 38) | QQYGSEPLT (SEQ ID NO: 53) | GYIFTSYTMH (SEQ ID NO: 48) | MGWINPNGGSTSYAQKFQG (SEQ ID NO: 42) | QEITTEFDY (SEQ ID NO: 36) |
| 08G07 | RASQSVDSYANSYLH (SEQ ID NO: 51) | RGSTRES (SEQ ID NO: 38) | QQSKSEPLT (SEQ ID NO: 39) | GYTFTSYTMH (SEQ ID NO: 34) | MGWINPSGGLANYAQKFQG (SEQ ID NO: 54) | SEITTDFDY (SEQ ID NO: 55) |
| 04E10 | RASQSVDSYANSYLH (SEQ ID NO: 51) | RGSTRES (SEQ ID NO: 38) | QQSKSEPLT (SEQ ID NO: 39) | GYIFTSYTMH (SEQ ID NO: 48) | MGWIKPNNGSASYAQKFQG (SEQ ID NO: 86) | SEITTEEDY (SEQ ID NO: 241) |
| 08B12 | RASQSVDSYANSYLH (SEQ ID NO: 51) | RGSTRET (SEQ ID NO: 56) | QQSKSDPLT (SEQ ID NO: 76) | GYIPTAYSMH (SEQ ID NO: 83) | MGWIKPNNGSTNYAQKFQG (SEQ ID NO: 87) | TEITTEFDY (SEQ ID NO: 88) |
| MH1 | RASQSVSSYANSYLH (SEQ ID NO: 37) | RGSTRES (SEQ ID NO: 38) | QQSKSEPLT (SEQ ID NO: 39) | GYTFTSYTMH (SEQ ID NO: 34) | MGWINPNGGSTSYAQKFQG (SEQ ID NO: 42) | QEITTEFDY (SEQ ID NO: 36) |
| MH2 | RASQSVSSYAQSYLH (SEQ ID NO: 57) | RGSTRET (SEQ ID NO: 56) | QQSGSSPLT (SEQ ID NO: 89) | GYTFTSYTMH (SEQ ID NO: 34) | MGWINPNGGSTSYAQKFQG (SEQ ID NO: 42) | QEITTEFDY (SEQ ID NO: 36) |
| MH3 | RASQSVSSYAQSYLH (SEQ ID NO: 57) | RGSTRET (SEQ ID NO: 56) | QQYGSSPLT (SEQ ID NO: 90) | GYTFTSYTMH (SEQ ID NO: 34) | MGWINPNGGSTSYAQKFQG (SEQ ID NO: 42) | QEITTEFDY (SEQ ID NO: 36) |

TABLE 4-continued

Amino acid sequences of CDRs of unique, library-derived and designer, human/cyno cross-reactive anti-C-MET IgGs.

| CLONE | LCDR1 | LCDR2 | LCDR3 | HCDR1 | HCDR2 | HCDR3 |
|---|---|---|---|---|---|---|
| MH4 | RASQSVSSYANSYLH (SEQ ID NO: 37) | RGSTRES (SEQ ID NO: 38) | QQSKSEPLT (SEQ ID NO: 39) | GYTFTSYTMH (SEQ ID NO: 34) | MGWINPSGGSTSYAQKFQG (SEQ ID NO: 40) | QEITTEFDY (SEQ ID NO: 36) |
| MH5 | RASQSVSSYAQSYLH (SEQ ID NO: 57) | RGSTRET (SEQ ID NO: 56) | QQSGSSPLT (SEQ ID NO: 89) | GYTFTSYTMH (SEQ ID NO: 34) | MGWINPSGGSTSYAQKFQG (SEQ ID NO: 40) | QEITTEFDY (SEQ ID NO: 36) |
| MH6 | RASQSVSSYAQSYLH (SEQ ID NO: 57) | RGSTRET (SEQ ID NO: 56) | QQYGSSPLT (SEQ ID NO: 90) | GYTFTSYTMH (SEQ ID NO: 34) | MGWINPSGGSTSYAQKFQG (SEQ ID NO: 40) | QEITTEFDY (SEQ ID NO: 36) |
| MH7 | RASQSVSSYANSYLH (SEQ ID NO: 37) | RGSTRES (SEQ ID NO: 38) | QQSKSEPLT (SEQ ID NO: 39) | GYTFTSYTMH (SEQ ID NO: 34) | MGIINPSGGSTSYAQKFQG (SEQ ID NO: 35) | QEITTEFDY (SEQ ID NO: 36) |
| MH8 | RASQSVSSYAQSYLH (SEQ ID NO: 57) | RGSTRET (SEQ ID NO: 56) | QQSGSSPLT (SEQ ID NO: 89) | GYTFTSYTMH (SEQ ID NO: 34) | MGIINPSGGSTSYAQKFQG (SEQ ID NO: 35) | QEITTEFDY (SEQ ID NO: 36) |
| MH9 | RASQSVSSYAQSYLH (SEQ ID NO: 57) | RGSTRET (SEQ ID NO: 56) | QQYGSSPLT (SEQ ID NO: 90) | GYTFTSYTMH (SEQ ID NO: 34) | MGIINPSGGSTSYAQKFQG (SEQ ID NO: 35) | QEITTEFDY (SEQ ID NO: 36) |
| MH10 | RASQSVSSYANSYLH (SEQ ID NO: 37) | RGSTRES (SEQ ID NO: 38) | QQSKSEPLT (SEQ ID NO: 39) | GYTFTSYAMH (SEQ ID NO: 41) | MGWINPSGGSTSYAQKFQG (SEQ ID NO: 40) | QEITTEFDY (SEQ ID NO: 36) |
| MH11 | RASQSVSSYAQSYLH (SEQ ID NO: 57) | RGSTRET (SEQ ID NO: 56) | QQSGSSPLT (SEQ ID NO: 89) | GYTFTSYAMH (SEQ ID NO: 41) | MGWINPSGGSTSYAQKFQG (SEQ ID NO: 40) | QEITTEFDY (SEQ ID NO: 36) |
| MH12 | RASQSVSSYAQSYLH (SEQ ID NO: 57) | RGSTRET (SEQ ID NO: 56) | QQYGSSPLT (SEQ ID NO: 90) | GYTFTSYAMH (SEQ ID NO: 41) | MGWINPSGGSTSYAQKFQG (SEQ ID NO: 40) | QEITTEFDY (SEQ ID NO: 36) |

TABLE 5

Biacore ® affinity values for IgG binding to human and cyno monomeric C-MET.

| Clone name | Human C-MET | | | | Cyno C-MET | | | |
|---|---|---|---|---|---|---|---|---|
| | ka (1/Ms) | kd (1/s) | Chi2 | KD (nM) | ka (1/Ms) | kd (1/s) | Chi2 | KD (nM) |
| Graft | 9.90E+04 | 3.70E−05 | 0.836 | 0.37 | 2.30E+05 | 5.20E−05 | 0.089 | 0.22 |
| h224G11 | 9.00E+04 | 4.20E−05 | 0.795 | 0.47 | 2.50E+05 | 1.10E−04 | 0.742 | 0.46 |
| 08G07 | 6.34E+04 | 7.54E−06 | 0.191 | 0.12 | 1.00E+05 | 2.40E−05 | 1.15 | 0.24 |
| 04F09 | 1.40E+05 | 1.80E−05 | 0.966 | 0.13 | 2.90E+05 | 5.60E−05 | 0.203 | 0.19 |
| 09E04 | 8.50E+04 | 1.60E−05 | 0.545 | 0.18 | 1.70E+05 | 6.40E−05 | 1.04 | 0.39 |
| 07A01 | 5.60E+04 | 1.30E−05 | 0.139 | 0.24 | 9.40E+04 | 1.60E−05 | 1.6 | 0.17 |
| MH4 | 8.70E+04 | 2.50E−05 | 1.62 | 0.28 | 2.60E+05 | 4.90E−05 | 0.099 | 0.19 |
| MH7 | 9.80E+04 | 2.90E−05 | 0.882 | 0.3 | 2.70E+05 | 5.20E−05 | 0.121 | 0.19 |
| MH10 | 7.10E+04 | 4.40E−05 | 0.496 | 0.63 | 1.80E+05 | 3.60E−05 | 1.07 | 0.2 |
| MH1 | 9.47E+04 | 7.11E−05 | 0.689 | 0.75 | 1.80E+05 | 2.60E−05 | 1.21 | 0.14 |
| 07C10 | 1.20E+05 | 9.40E−05 | 0.03 | 0.78 | 6.50E+04 | 2.10E−04 | 0.213 | 3.2 |
| 09B08 | 3.70E+04 | 4.10E−05 | 0.064 | 1.1 | 6.00E+04 | 1.20E−05 | 0.135 | 0.2 |
| 04E10 | 3.10E+04 | 5.00E−05 | 0.055 | 1.6 | 4.90E+04 | 1.10E−04 | 0.099 | 2.2 |
| MH5 | 7.70E+04 | 1.50E−04 | 0.883 | 2 | 1.70E+05 | 2.10E−04 | 1.63 | 1.3 |
| 09A12 | 7.40E+04 | 1.50E−04 | 0.671 | 2 | 1.60E+05 | 2.30E−04 | 0.919 | 1.5 |
| MH8 | 6.60E+04 | 1.50E−04 | 0.638 | 2.2 | 1.60E+05 | 2.10E−04 | 0.736 | 1.3 |
| MH2 | 7.30E+04 | 1.80E−04 | 1.2 | 2.5 | 2.40E+05 | 2.10E−04 | 0.068 | 0.87 |
| MH11 | 6.20E+04 | 1.60E−04 | 0.323 | 2.6 | 1.50E+05 | 1.80E−04 | 0.589 | 1.2 |
| MH12 | 5.60E+04 | 3.70E−04 | 0.134 | 6.5 | 1.10E+05 | 4.30E−04 | 1.29 | 4 |
| MH9 | 5.90E+04 | 3.90E−04 | 0.164 | 6.6 | 1.10E+05 | 4.80E−04 | 1.89 | 4.3 |
| MH03 | 6.80E+04 | 5.10E−04 | 0.505 | 7.6 | 1.50E+05 | 6.20E−04 | 1.06 | 4.1 |
| MH6 | 6.50E+04 | 5.30E−04 | 0.475 | 8.2 | 1.60E+05 | 6.30E−04 | 0.861 | 4 |
| 08B12 | 3.70E+04 | 3.10E−04 | 0.051 | 8.4 | 5.40E+04 | 4.30E−04 | 0.039 | 8.1 |

TABLE 6

Flow cytometric EC50 values for IgG binding to human and cyno CHO-K1.

| | EC50 (nM) | |
|---|---|---|
| Clone | hucMET | cycMET |
| MH7 | 1.14 | 0.54 |
| MH9 | 1.23 | 0.65 |
| MH8 | 1.24 | 0.57 |
| MH12 | 1.25 | 0.51 |
| MH6 | 1.33 | 0.72 |
| MH2 | 1.59 | 0.34 |
| MH3 | 1.66 | 0.27 |
| MH11 | 1.68 | 0.69 |
| MH4 | 1.72 | 0.48 |
| MH5 | 1.76 | 0.3 |
| MH1 | 2.02 | 0.26 |
| MH10 | 2.14 | 0.46 |
| 09A12 | 2.33 | 0.28 |
| 09E04 | 2.9 | 1.11 |
| 08G07 | 4.19 | 0.68 |
| h224G11 | 6.83 | 0.82 |
| 07A01 | 7.44 | 1.74 |
| 09B08 | 9.3 | 3.78 |
| 07C10 | 9.59 | 2.82 |
| 04E10 | 9.66 | 2.94 |
| 08B12 | 11.67 | 1.34 |
| 04F09 | 12.41 | 0.64 |
| Isotype IgG4 | N.D. | N.D. |

N.D.—Not determined

TABLE 7

Human T cell epitope content in v-domains predicted by iTOPE ™ and TCED ™.

| Clone Name | Germline epitopes | Low Affinity Foreign | High Affinity Foreign | TCED+ |
|---|---|---|---|---|
| h224G11 VL | 4 | 1 | 2 | 0 |
| h224G11 VH | 7 | 1 | 2 | 0 |
| 08G07 VL | 1 | 2 | 1 | 0 |
| 08G07 VH | 8 | 1 | 1 | 0 |
| 07A01 VL | 1 | 1 | 1 | 0 |
| 07A01 VH | 8 | 2 | 2 | 0 |
| MH1 VL | 1 | 2 | 1 | 0 |
| MH1 VH | 8 | 2 | 1 | 0 |
| MH4 VL | 1 | 2 | 1 | 0 |
| MH4 VH | 8 | 1 | 1 | 0 |
| MH7 VL | 1 | 2 | 1 | 0 |
| MH7 VH | 10 | 0 | 1 | 0 |
| MH7-1 VL | 1 | 2 | 0 | 0 |
| MH7-1 VH | 10 | 0 | 1 | 0 |
| MH7-2 VL | 1 | 1 | 0 | 0 |
| MH7-2 VH | 10 | 0 | 1 | 0 |
| MH7-3 VL | 1 | 1 | 0 | 0 |
| MH7-3 VH | 10 | 0 | 1 | 0 |

TABLE 8

Amino acid sequences of CDRs of unique, deimmunised, designer, human/cyno cross-reactive anti-C-MET IgGs.

| CLONE | LCDR1 | LCDR2 | LCDR3 | HCDR1 | HCDR2 | HCDR3 |
|---|---|---|---|---|---|---|
| MH7-1 | RASQSVSSYANSYLH (SEQ ID NO: 37) | RGSTRET (SEQ ID NO: 56) | QQSKSEPLT (SEQ ID NO: 39) | GYTFTSYTMH (SEQ ID NO: 34) | MGIINPSGGSTSYAQKFQG (SEQ ID NO: 35) | QEITTEFDY (SEQ ID NO: 36) |
| MH7-2 | RASQSVSSYANSYLH (SEQ ID NO: 37) | RGSTRET (SEQ ID NO: 56) | QQSKESPLT (SEQ ID NO: 47) | GYTFTSYTMH (SEQ ID NO: 34) | MGIINPSGGSTSYAQKFQG (SEQ ID NO: 35) | QEITTEFDY (SEQ ID NO: 36) |
| MH7-3 | RASQSVSSYAQSYLH (SEQ ID NO: 57) | RGSTRET (SEQ ID NO: 56) | QQSKESPLT (SEQ ID ) NO: 47 | GYTFTSYTMH (SEQ ID NO: 34) | MGIINPSGGSTSYAQKFQG (SEQ ID NO: 35) | QEITTEFDY (SEQ ID NO: 36) |

TABLE 9

BIACORE® affinity values for IgG binding to human and cyno monomeric C-MET.

| Clone name | Human C-MET | | | | Cyno C-MET | | | |
|---|---|---|---|---|---|---|---|---|
| | ka (1/Ms) | kd (1/s) | Chi2 | KD (nM) | ka (1/Ms) | kd (1/s) | Chi2 | KD (nM) |
| MH7.1 | 9.79E+04 | 1.51E-04 | 0.11 | 1.54 | 1.81E+05 | 1.98E-04 | 0.683 | 1.1 |
| MH7.2 | 9.32E+04 | 1.98E-04 | 0.108 | 2.12 | 1.83E+05 | 1.59E-04 | 0.394 | 0.87 |
| MH7.3 | 9.44E+04 | 1.23E-04 | 0.137 | 1.31 | 1.68E+05 | 1.74E-04 | 0.687 | 1.03 |

TABLE 10

Examples of antibody variable region amino acid sequences.

Antibody MH7-3 heavy chain variable (VH) region
QVQLVQSGAEVKKPGASVKVSCKASGYTFTSYTMHWVRQAPGQGLEWMG
IINPSGGSTSYAQKFQGRVTMTRDTSTSTVYMELSSLRSEDTAVYYCAR
QEITTEFDYWGQGTLVTVSS (SEQ ID NO: 1)

Antibody MH7-3 light chain variable (VL) region
EIVLTQSPGTLSLSPGERATLSCRASQSVSSYAQSYLHWYQQKPGQAPR
LLIYRGSTRETGIPDRFSGSGSGTDFTLTISRLEPEDFAVYYCQQSKES
PLTFGGGTKVEIK (SEQ ID NO: 2)

Antibody MH7-2 heavy chain variable (VH) region
QVQLVQSGAEVKKPGASVKVSCKASGYTFTSYTMHWVRQAPGQGLEWMG
IINPSGGSTSYAQKFQGRVTMTRDTSTSTVYMELSSLRSEDTAVYYCAR
QEITTEFDYWGQGTLVTVSS (SEQ ID NO: 3)

Antibody MH7-2 light chain variable (VL) region
EIVLTQSPGTLSLSPGERATLSCRASQSVSSYANSYLHWYQQKPGQAPR
LLIYRGSTRETGIPDRFSGSGSGTDFTLTISRLEPEDFAVYYCQQSKES
PLTFGGGTKVEIK (SEQ ID NO: 4)

Antibody MH7-1 heavy chain variable (VH) region
QVQLVQSGAEVKKPGASVKVSCKASGYTFTSYTMHWVRQAPGQGLEWMG
IINPSGGSTSYAQKFQGRVTMTRDTSTSTVYMELSSLRSEDTAVYYCAR
QEITTEFDYWGQGTLVTVSS (SEQ ID NO: 5)

Antibody MH7-1 light chain variable (VL) region
EIVLTQSPGTLSLSPGERATLSCRASQSVSSYANSYLHWYQQKPGQAPR
LLIYRGSTRETGIPDRFSGSGSGTDFTLTISRLEPEDFAVYYCQQSKE
PLTFGGGTKVEIK (SEQ ID NO: 6)

Antibody MH7 heavy chain variable (VH) region
QVQLVQSGAEVKKPGASVKVSCKASGYTFTSYTMHWVRQAPGQGLEWMG
IINPSGGSTSYAQKFQGRVTMTRDTSTSTVYMELSSLRSEDTAVYYCAR
QEITTEFDYWGQGTLVTVSS (SEQ ID NO: 7)

Antibody MH7 light chain variable (VL) region
EIVLTQSPGTLSLSPGERATLSCRASQSVSSYANSYLHWYQQKPGQAPR
LLIYRGSTRESGIPDRFSGSGSGTDFTLTISRLEPEDFAVYYCQQSKE
PLTFGGGTKVEIK (SEQ ID NO: 8)

Antibody 08G07 heavy chain variable (VH) region
QVQLVQSGAEVKKPGASVKVSCKASGYTFTSYTMHWVRQAPGQGLEWMG
WINPSGGLANYAQKFQGRVTMTRDTSTSTVYMELSSLRSEDTAVYYCAR
SEITTDFDYWGQGTLVTVSS (SEQ ID NO: 9)

Antibody 08G07 light chain variable (VL) region
EIVLTQSPGTLSLSPGERATLSCRASQSVDSYANSYLHWYQQKPGQAPR
LLIYRGSTRESGIPDRFSGSGSGTDFTLTISRLEPEDFAVYYCQQSKSE
PLTFGGGTKVEIK (SEQ ID NO: 10)

TABLE 11

Examples of antibody Fc region amino acid sequences.

Human IgG4 wild type
ASTKGPSVFPLAPCSRSTSESTAALGCLVKDYFPEPVTVSWNSGALTSGV
HTFPAVLQSSGLYSLSSVVTVPSSSLGTKTYTCNVDHKPSNTKVDKRVES
KYGPPCPSCPAPEFLGGPSVFLFPPKPKDTLMISRTPEVTCVVVDVSQED
PEVQFNWYVDGVEVHNAKTKPREEQFNSTYRVVSVLTVLHQDWLNGKEYK
CKVSNKGLPSSIEKTISKAKGQPREPQVYTLPPSQEEMTKNQVSLTCLVK
GFYPSDIAVEWESNGQPENNYKTTPPVLDSDGSFFLYSRLTVDKSRWQEG
NVFSCSVMHEALHNHYTQKSLSLSLGK (SEQ ID NO: 11)

Human IgG4 (S228P)
ASTKGPSVFPLAPCSRSTSESTAALGCLVKDYFPEPVTVSWNSGALTSGV
HTFPAVLQSSGLYSLSSVVTVPSSSLGTKTYTCNVDHKPSNTKVDKRVES
KYGPPCPPCPAPEFLGGPSVFLFPPKPKDTLMISRTPEVTCVVVDVSQED
PEVQFNWYVDGVEVHNAKTKPREEQFNSTYRVVSVLTVLHQDWLNGKEYK
CKVSNKGLPSSIEKTISKAKGQPREPQVYTLPPSQEEMTKNQVSLTCLVK
GFYPSDIAVEWESNGQPENNYKTTPPVLDSDGSFFLYSRLTVDKSRWQEG
NVFSCSVMHEALHNHYTQKSLSLSLGK (SEQ ID NO: 12)

Human IgG1 wild type
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK TABLE 11-continued Examples of antibody Fc region amino acid sequences.

EYKCKVSNKALPAPIEKTISKAKGQPREPQVYTLPPS<u>RDELT</u>KNQVSLTC
LVKGFYPSDIAVEWESNGQPENNYKTTPPVLDSDGSFFLYSKLTVDKSRW
QQGNVFSCSVMHEALHNHYTQKSLSLSPGK (SEQ ID NO: 13)

Human IgG1-3M
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPEAGAPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPS<u>RDELT</u>KNQVSLTC
LVKGFYPSDIAVEWESNGQPENNYKTTPPVLDSDGSFFLYSKLTVDKSRW
QQGNVFSCSVMHEALHNHYTQKSLSLSPGK (SEQ ID NO: 14)

Human IgG2 wild type
ASTKGPSVFPLAPCSRSTSESTAALGCLVKDYFPEPVTVSWNSGALTSGV
HTFPAVLQSSGLYSLSSVVTVPSSNFGTQTYTCNVDHKPSNTKVDKTVER
KCCVECPPCPAPPVAGPSVFLFPPKPKDTLMISRTPEVTCVVVDVSHEDP
EVQFNWYVDGVEVHNAKTKPREEQFNSTFRVVSVLTVVHQDWLNGKEYKC
KVSNKGLPAPIEKTISKTKGQPREPQVYTLPPSREEMTKNQVSLTCLVKG FYPSDISVEWESNGQPENNYKTTPPMLDSDGSFFLYSKLTVDKSRWQQGN
VFSCSVMHEALHNHYTQKSLSLSPGK (SEQ ID NO: 15)

Human IgG1 wild type "REEM" allotype
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPS<u>REEM</u>TKNQVSLTC
LVKGFYPSDIAVEWESNGQPENNYKTTPPVLDSDGSFFLYSKLTVDKSRW
QQGNVFSCSVMHEALHNHYTQKSLSLSPGK (SEQ ID NO: 16)

Human IgG1-3M "REEM" allotype
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPEAGAPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPS<u>REEM</u>KNQVSLTCL
VKGFYPSDIAVEWESNGQPENNYKTTPPVLDSDGSFFLYSKLTVDKSRWQ
QGNVFSCSVMHEALHNHYTQKSLSLSPGK (SEQ ID NO: 17)

TABLE 12

Examples of C-MET protein amino acid sequences.

Human C-MET sequence

MKAPAVLAPGILVLLFTLVQRSNGECKEALAKSEMNVNMKYQLPNFTAETPIQNVILHEH
HIFLGATNYIYVLNEEDLQKVAEYKTGPVLEHPDCFPCQDCSSKANLEGGVWKDNINMAL
VVDTYYDDQLISCGSVNRGTCQRHVFPHNHTADIQSEVHCIFSPQIEEPSQCPDCVVSAL
GAKVLSSVKDRFINFFVGNTINSSYFPDHPLHSISVRRLKETKDGFMFLTDQSYIDVLPE
FRDSYPIKYVHAFESNNFIYFLTVQRETLDAQTFHTRIIRFCSINSGLHSYMEMPLECIL
TEKRKKRSTKKEVFNILQAAYVSKPGAQLARQIGASLNDDILFGVFAQSKPDSAEPMDRS
AMCAFPIKYVNDFFNKIVNKNNVRCLQHFYGPNHEHCFNRTLLRNSSGCEARRDEYRTEF
TTALQRVDLFMGQFSEVLLTSISTFIKGDLTIANLGTSEGRFMQVVVERSGPSTPHVNFL
LDSHPVSPEVIVEHTLNQNGYTLVITGKKITKIPLNGLGCRHFQSCSQCLSAPPFVQCGW
CHDKCVRSEECLEGTWTQQICLPAIYKVFPNSAPLEGGTRLTICGWDFGFRRNNKFDLKK
TRVLLGNESCTLTLSESTMNTLKCTVGPAMNKHFNMSIIISNGHGTTQYSTFSYVDPVIT
SISPKYGPMAGGTLLTLTGNYLNEGNSRHISIGGKTCTLKSVSNSILECYTPAQTISTEF
AVKLKIDLANRETSIFSYREDPIVYEIHPTKSFISGGSTITGVGKNLNSVSVPRMVINVH
EAGRNFTVACQHRENSEIICCTTPSLQQLNLQLPLKTKAFFMLDGILSKYFDLIYVHNPV
FKPFEKPVMISMGNENVLEIKGNDIDPEAVKGEVLKVGNKSCENTHLHSEAVLCTVPNDL
LKLNSELNIEWKQAISSTVLGKVIVQPDQNFTGLIAGVVSISTALLLLLGFFLWLKKRKQ
IKDLGSELVRYDARVHTPHLDRLVSARSVSPTTEMVSNESVDYRATFPEDQFPNESQNGS
CRQVQYPLTDMSPILTSGDSDISSPLLQNTVHIDLSALNPELVQAVQHVVIGPSSLIVHF
NEVIGRGHFGCVYHGTLLDNGKKIHCAVKSLNRITDIGEVSQFLTEGIIMKDFSHPNVL
SLLGICLRSEGSPLVVLPYMKHGDLRNFIRNETHNPTVKDLIGFGLQVAKGMKYLASKKF
VHRDLAARNCMLDEKFTVKVADFGLARDMYDKEYYSVHNKTGAKLPVKWMALESLQTQKFTTKS
DVWSFGVLLWELMTRGAPPYPDVNTFDITVYLLQGRRLLQPEYCPDPLYEVMLKCWHPKAEMRP
SFSELVERISAIFSTFIGEHYVHVNATYVNVKCVAPYPELLSSEDNADDEVD
TRPASFWETS (SEQID NO: 18)

Cynomolgus Monkey C-MET sequence mkapavlvpg ilvllftlvq rsngeckeal aksemnvnmk yqlpnftaet
aiqnvilheh hiflgatnyi yvlneedlqk vaeyktgpvl ehpdcfpcqd
csskanlsgg vwkdninmal vvdtyyddql iscgsvnrgt cqrhvfphnh
tadiqsevhc ifspqieepn qcpdcvvsal gakvlssvkd rfinffvgnt
inssyfphhp lhsisvrrlk etkdgfmflt dqsyidvlpe frdsypikyi
hafesnnfiy fltvgretln aqtfhtriir fcslnsglhs ymemplecil
tekrkkrstk kevfnilqaa yvskpgagla rqigaslndd ilfgvfaqsk
pdsaepmdrs amcafpikyv ndffnkivnk nnvrclqhfy gpnhehcfnr
tllrnssgce arrdeyraef ttalqrvdlf mgqfsevllt sistfvkgdl
tianlgtseg rfmqvvvsrs gpstphvnfl ldshpvspev ivehplnqng
ytlvvtgkki tkiplnglgc rhfqscsqcl sappfvqcgw chdkcvrsee
cpsgtwtqqi clpaiykvfp tsapleggtr lticgwdfgf rrnnkfdlkk
trvllgnesc tltlsestmn tlkctvgpam nkhfnmsiii snghgttqys
tfsyvdpiit sispkygpma ggtlltltgn ylnsgnsrhi siggktctlk
svsnsilecy tpaqtistef avklkidlan retsifsyre dpivyeihpt
ksfisggsti tgvgknlhsv svprmvinvh eagrnftvac qhrnseiic
cttpslqqln lqlplktkaf fmldgilsky fdliyvhnpv fkpfekpvmi
smgnenvlei kgndidpeav kgevlkvgnk scenihlhse avlctvpndl
lklnselnie wkqaisstvl gkvivqpdqn ftgliagvvs isiallllg
lflwlkkrkq ikdlgselvr ydarvhtphl drlvsarsvs pttemvsnes TABLE 12-continued Examples of C-MET protein amino acid sequences.

vdyratfped qfpnssqngs crqvqypltd mspiltsgds disspllqnt
vhidlsalnp elvqavqhvv igpsslivhf nevigrghfq cvyhgtlldn
dgkkihcavk slnritdige vsqfltegii mkdfshpnvl sllgiclrse
gsplvvlpym khgdlrnfir nethnptvkd ligfglqvak gmkylaskkf
vhrdlaarnc mldekftvkv adfglardmy dkeyysvhnk tgaklpvkwm
aleslqtqkf ttksdvwsfg vllwelmtrg appypdvntf ditvyllqgr
rllqpeycpd plyevmlkcw hpkaemrpsf selvsrisai fstfigehyv
hvnatyvnvk cvapypslls sednaddevdt (SEQ ID NO: 19)

The invention claimed is:

1. An anti-C-MET antibody or an antigen-binding portion thereof, wherein the antibody or antigen-binding portion comprises a heavy chain variable (VH) region and a light chain variable (VL) region, wherein
   (a) the VH region amino acid sequence comprises HCDR1 of GYTFTSYTMH (SEQ ID NO: 34), HCDR2 of MGIINPSGGSTSYAQKFQG (SEQ ID NO: 35) and HCDR3 of QEITTEFDY (SEQ ID NO: 36); and the VL region amino acid sequence comprises LCDR1 of RASQSVSSYAQSYLH (SEQ ID NO: 57), LCDR2 of RGSTRET (SEQ ID NO: 56) and LCDR3 of QQSKESPLT (SEQ ID NO: 47);
   (b) the VH region amino acid sequence comprises HCDR1 of GYTFTSYTMH (SEQ ID NO: 34), HCDR2 of MGIINPSGGSTSYAQKFQG (SEQ ID NO: 35) and HCDR3 of QEITTEFDY (SEQ ID NO: 36); and the VL region amino acid sequence comprises LCDR1 of RASQSVSSYANSYLH (SEQ ID NO: 37), LCDR2 of RGSTRET (SEQ ID NO: 56) and LCDR3 of QQSKESPLT (SEQ ID NO: 47); or
   (c) the VH region amino acid sequence comprises HCDR1 of GYTFTSYTMH (SEQ ID NO: 34), HCDR2 of MGIINPSGGSTSYAQKFQG (SEQ ID NO: 35) and HCDR3 of QEITTEFDY (SEQ ID NO: 36); and the VL region amino acid sequence comprises LCDR1 of RASQSVSSYANSYLH (SEQ ID NO: 37), LCDR2 of RGSTRET (SEQ ID NO: 56) and LCDR3 of QQSKSEPLT (SEQ ID NO: 39).

2. The antibody or antigen-binding portion of claim 1, wherein
   (a) the VH region amino acid sequence comprises SEQ ID NO:1 and the VL region amino acid sequence comprises SEQ ID NO:2;
   (b) the VH region amino acid sequence comprises SEQ ID NO:3 and the VL region amino acid sequence comprises SEQ ID NO:4; or
   (c) the VH region amino acid sequence comprises SEQ ID NO:5 and the VL region amino acid sequence comprises SEQ ID NO:6.

3. The antibody or antigen-binding portion of claim 1 wherein the antibody is humanized or chimeric.

4. The antibody or antigen-binding portion of claim 1, wherein the VH region, the VL region, or both the VH and the VL region comprise one or more human framework region amino acid sequences.

5. The antibody or antigen-binding portion of claim 1, wherein the VH region, the VL region, or both the VH and the VL region comprise a human variable region framework scaffold amino acid sequence into which the CDRs have been inserted.

6. The antibody or antigen-binding portion of claim 1, wherein the VH region comprises an IGHV1-46 human germline scaffold amino acid sequence into which the HCDR1, HCDR2 and HCDR3 amino acid sequences have been inserted.

7. The antibody or antigen-binding portion of claim 1, wherein the VL region comprises an IGKV3-20 human germline scaffold amino acid sequence into which the LCDR1, LCDR2 and LCDR3 amino acid sequences have been inserted.

8. The antibody or antigen-binding portion of claim 1, wherein the antibody or antigen-binding portion comprises an immunoglobulin constant region.

9. The antibody or antigen-binding portion of claim 8, wherein the immunoglobulin constant region is IgG, IgE, IgM, IgD, IgA or IgY.

10. The antibody or antigen-binding portion of claim 9, wherein the immunoglobulin constant region is IgG1, IgG2, IgG3, IgG4, IgA1 or IgA2.

11. The antibody or antigen-binding portion of claim 8, wherein the immunoglobulin constant region is immunologically inert.

12. The antibody or antigen-binding portion of claim 8, wherein the immunoglobulin constant region is a wild-type human IgG4 constant region, a human IgG4 constant region comprising the amino acid substitution S228P, a wild-type human IgG1 constant region, a human IgG1 constant region comprising the amino acid substitutions L234A, L235A and G237A or a wild-type human IgG2 constant region.

13. The antibody or antigen-binding portion of claim 8, wherein the immunoglobulin constant region comprises any one of SEQ ID NOS:11-17.

14. The antibody or antigen-binding portion of claim 1, wherein the antibody or antigen-binding portion is an Fab, an Fab', an F(ab')2, an Fv, an scFv, a maxibody, a minibody, a diabody, a triabody, a tetrabody, or a bis-scFv.

15. The antibody or antigen-binding portion of claim 1, wherein the antibody or antigen-binding portion is monoclonal.

16. The antibody or antigen-binding portion of claim 1, wherein the antibody or antigen-binding portion is tetrameric, tetravalent or multispecific.

17. The antibody or antigen-binding portion of claim 1, wherein the antibody or antigen-binding portion is a bispecific antibody or bispecific antigen-binding portion that binds specifically to a first antigen and a second antigen, wherein the first antigen is C-MET and the second antigen is not C-MET.

18. The antibody or antigen-binding portion of claim 1, wherein the antibody or antigen-binding portion comprises a human IgG4 constant region comprising the amino acid substitution S228P, and wherein the antibody or antigen-binding portion has
(a) a melting temperature (Tm) from about 77° C. to about 81° C.; and/or
(b) an isoelectric point (pI) greater than about pH 7.4.

19. An immunoconjugate comprising the antibody or antigen-binding portion of claim 1 linked to a therapeutic agent.

20. The immunoconjugate of claim 19, wherein the therapeutic agent is a cytotoxin, a radioisotope, a chemotherapeutic agent, an immunomodulatory agent, a cytostatic enzyme, a cytolytic enzyme, a therapeutic nucleic acid, an anti-angiogenic agent, an anti-proliferative agent, or a pro-apoptotic agent.

21. A pharmaceutical composition comprising the antibody or antigen-binding portion of claim 1 and a pharmaceutically acceptable carrier.

22. A nucleic acid molecule encoding both the VH and the VL region amino acid sequences of the antibody or antigen-binding portion of claim 1.

23. An expression vector comprising the nucleic acid molecule of claim 22.

24. A method of producing an anti-C-MET antibody or an antigen-binding portion thereof, the method comprising:
culturing a recombinant host cell comprising the expression vector of claim 23 under conditions whereby the nucleic acid molecule is expressed, thereby producing the antibody or antigen-binding portion; and
isolating the antibody or antigen-binding portion from the host cell or culture.

25. A recombinant host cell comprising the nucleic acid molecule of claim 22.

26. An anti-C-MET antibody or an antigen-binding portion thereof, wherein the antibody or antigen-binding portion comprises a heavy chain variable (VH) region and a light chain variable (VL) region, wherein the VH region amino acid sequence comprises HCDR1 of GYTFTSYTMH (SEQ ID NO: 34), HCDR2 of MGIINPSGGSTSYAQKFQG (SEQ ID NO: 35) and HCDR3 of QEITTEFDY (SEQ ID NO: 36); and the VL region amino acid sequence comprises LCDR1 of RASQSVSSYAQSYLH (SEQ ID NO: 57), LCDR2 of RGSTRET (SEQ ID NO: 56) and LCDR3 of QQSKESPLT (SEQ ID NO: 47).

27. An anti-C-MET antibody or an antigen-binding portion thereof, wherein the antibody or antigen-binding portion comprises a heavy chain variable (VH) region and a light chain variable (VL) region, wherein the VH region amino acid sequence comprises HCDR1 of GYTFTSYTMH (SEQ ID NO: 34), HCDR2 of MGIINPSGGSTSYAQKFQG (SEQ ID NO: 35) and HCDR3 of QEITTEFDY (SEQ ID NO: 36); and the VL region amino acid sequence comprises LCDR1 of RASQSVSSYANSYLH (SEQ ID NO: 37), LCDR2 of RGSTRET (SEQ ID NO: 56) and LCDR3 of QQSKESPLT (SEQ ID NO: 47).

28. An anti-C-MET antibody or an antigen-binding portion thereof, wherein the antibody or antigen-binding portion comprises a heavy chain variable (VH) region and a light chain variable (VL) region, wherein the VH region amino acid sequence comprises HCDR1 of GYTFTSYTMH (SEQ ID NO: 34), HCDR2 of MGIINPSGGSTSYAQKFQG (SEQ ID NO: 35) and HCDR3 of QEITTEFDY (SEQ ID NO: 36); and the VL region amino acid sequence comprises LCDR1 of RASQSVSSYANSYLH (SEQ ID NO: 37), LCDR2 of RGSTRET (SEQ ID NO: 56) and LCDR3 of QQSKSEPLT (SEQ ID NO: 39).

\* \* \* \* \*

SEQUENCE LISTING

<160> NUMBER OF SEQ ID NOS: 255

<210> SEQ ID NO 1
<211> LENGTH: 118
<212> TYPE: PRT
<213> ORGANISM: Artificial Sequence
<220> FEATURE:
<223> OTHER INFORMATION: Antibody MH7-3 heavy chain variable (VH) region

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Thr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gln Glu Ile Thr Thr Glu Phe Asp Tyr Trp Gly Gln Gly Thr
            100                 105                 110

Leu Val Thr Val Ser Ser
        115

<210> SEQ ID NO 2
<211> LENGTH: 111
<212> TYPE: PRT
<213> ORGANISM: Artificial Sequence
<220> FEATURE:
<223> OTHER INFORMATION: Antibody MH7-3 light chain variable (VL) region

<400> SEQUENCE: 2

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Ala Gln Ser Tyr Leu His Trp Tyr Gln Gln Lys Pro Gly Gln Ala Pro
            35                  40                  45

Arg Leu Leu Ile Tyr Arg Gly Ser Thr Arg Glu Thr Gly Ile Pro Asp
        50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

```
Glu Ser Pro Leu Thr Phe Gly Gly Gly Thr Lys Val Glu Ile Lys
                100                 105                 110
```

<210> SEQ ID NO 3
<211> LENGTH: 118
<212> TYPE: PRT
<213> ORGANISM: Artificial Sequence
<220> FEATURE:
<223> OTHER INFORMATION: Antibody MH7-2 heavy chain variable (VH) region

<400> SEQUENCE: 3

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Thr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gln Glu Ile Thr Thr Glu Phe Asp Tyr Trp Gly Gln Gly Thr
            100                 105                 110

Leu Val Thr Val Ser Ser
        115
```

<210> SEQ ID NO 4
<211> LENGTH: 111
<212> TYPE: PRT
<213> ORGANISM: Artificial Sequence
<220> FEATURE:
<223> OTHER INFORMATION: Antibody MH7-2 light chain variable (VL) region

<400> SEQUENCE: 4

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Ala Asn Ser Tyr Leu His Trp Tyr Gln Gln Lys Pro Gly Gln Ala Pro
        35                  40                  45

Arg Leu Leu Ile Tyr Arg Gly Ser Thr Arg Glu Thr Gly Ile Pro Asp
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Ser Pro Leu Thr Phe Gly Gly Gly Thr Lys Val Glu Ile Lys
            100                 105                 110
```

<210> SEQ ID NO 5
<211> LENGTH: 118
<212> TYPE: PRT
<213> ORGANISM: Artificial Sequence
<220> FEATURE:
<223> OTHER INFORMATION: Antibody MH7-1 heavy chain variable (VH) region

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Thr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gln Glu Ile Thr Thr Glu Phe Asp Tyr Trp Gly Gln Gly Thr
            100                 105                 110

Leu Val Thr Val Ser Ser
            115

<210> SEQ ID NO 6
<211> LENGTH: 111
<212> TYPE: PRT
<213> ORGANISM: Artificial Sequence
<220> FEATURE:
<223> OTHER INFORMATION: Antibody MH7-1 light chain variable (VL) region

<400> SEQUENCE: 6

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Ala Asn Ser Tyr Leu His Trp Tyr Gln Gln Lys Pro Gly Gln Ala Pro
        35                  40                  45

Arg Leu Leu Ile Tyr Arg Gly Ser Thr Arg Glu Thr Gly Ile Pro Asp
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Ser Glu Pro Leu Thr Phe Gly Gly Gly Thr Lys Val Glu Ile Lys
            100                 105                 110

<210> SEQ ID NO 7
<211> LENGTH: 118
<212> TYPE: PRT
<213> ORGANISM: Artificial Sequence
<220> FEATURE:
<223> OTHER INFORMATION: Antibody MH7 heavy chain variable (VH) region

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Thr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gln Glu Ile Thr Thr Glu Phe Asp Tyr Trp Gly Gln Gly Thr
            100                 105                 110

Leu Val Thr Val Ser Ser
        115

<210> SEQ ID NO 8
<211> LENGTH: 111
<212> TYPE: PRT
<213> ORGANISM: Artificial Sequence
<220> FEATURE:
<223> OTHER INFORMATION: Antibody MH7 light chain variable (VL) region

<400> SEQUENCE: 8

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Ala Asn Ser Tyr Leu His Trp Tyr Gln Gln Lys Pro Gly Gln Ala Pro
        35                  40                  45

Arg Leu Leu Ile Tyr Arg Gly Ser Thr Arg Glu Ser Gly Ile Pro Asp
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Ser Glu Pro Leu Thr Phe Gly Gly Gly Thr Lys Val Glu Ile Lys
            100                 105                 110

<210> SEQ ID NO 9
<211> LENGTH: 118
<212> TYPE: PRT
<213> ORGANISM: Artificial Sequence
<220> FEATURE:
<223> OTHER INFORMATION: Antibody 08G07 heavy chain variable (VH) region

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Thr Met His Trp Val Arg Gln Ala Pro Gly Gln Gly Leu Glu Trp Met
        35                  40                  45

Gly Trp Ile Asn Pro Ser Gly Gly Leu Ala Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Glu Ile Thr Thr Asp Phe Asp Tyr Trp Gly Gln Gly Thr
            100                 105                 110

Leu Val Thr Val Ser Ser
        115

<210> SEQ ID NO 10
<211> LENGTH: 111
<212> TYPE: PRT

```
<213> ORGANISM: Artificial Sequence
<220> FEATURE:
<223> OTHER INFORMATION: Antibody 08G07 light chain variable (VL) region

<400> SEQUENCE: 10

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Asp Ser Tyr
                20                  25                  30

Ala Asn Ser Tyr Leu His Trp Tyr Gln Gln Lys Pro Gly Gln Ala Pro
            35                  40                  45

Arg Leu Leu Ile Tyr Arg Gly Ser Thr Arg Glu Ser Gly Ile Pro Asp
50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Ser Glu Pro Leu Thr Phe Gly Gly Gly Thr Lys Val Glu Ile Lys
            100                 105                 110

<210> SEQ ID NO 11
<211> LENGTH: 327
<212> TYPE: PRT
<213> ORGANISM: Homo sapiens

<400> SEQUENCE: 11

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240
```

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 12
<211> LENGTH: 327
<212> TYPE: PRT
<213> ORGANISM: Homo sapiens

<400> SEQUENCE: 12

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser

```
                     275                 280                 285
Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 13
<211> LENGTH: 330
<212> TYPE: PRT
<213> ORGANISM: Homo sapiens

<400> SEQUENCE: 13

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

-continued

Gln Lys Ser Leu Ser Leu Ser Pro Gly Lys
            325                 330

<210> SEQ ID NO 14
<211> LENGTH: 330
<212> TYPE: PRT
<213> ORGANISM: Homo sapiens

<400> SEQUENCE: 14

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 15
<211> LENGTH: 326
<212> TYPE: PRT
<213> ORGANISM: Homo sapiens

<400> SEQUENCE: 15

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 16
<211> LENGTH: 330
<212> TYPE: PRT
<213> ORGANISM: Homo sapiens

<400> SEQUENCE: 16

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 17
<211> LENGTH: 329
<212> TYPE: PRT
<213> ORGANISM: Homo sapiens

<400> SEQUENCE: 17

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr

```
                65                  70                  75                  80
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 18
<211> LENGTH: 1390
<212> TYPE: PRT
<213> ORGANISM: Homo sapiens

<400> SEQUENCE: 18

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110
```

```
Lys Asp Asn Ile Asn Met Ala Leu Val Val Asp Thr Tyr Asp Asp
            115                 120                 125

Gln Leu Ile Ser Cys Gly Ser Val Asn Arg Gly Thr Cys Gln Arg His
        130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
        260                 265                 270

Thr Phe His Thr Arg Ile Ile Arg Phe Cys Ser Ile Asn Ser Gly Leu
    275                 280                 285

His Ser Tyr Met Glu Met Pro Leu Glu Cys Ile Leu Thr Glu Lys Arg
290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Glu Gly Arg Phe Met Gln
450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
```

-continued

```
                530             535             540
Cys Val Arg Ser Glu Glu Cys Leu Ser Gly Thr Trp Thr Gln Gln Ile
545             550             555             560

Cys Leu Pro Ala Ile Tyr Lys Val Phe Pro Asn Ser Ala Pro Leu Glu
                565             570             575

Gly Gly Thr Arg Leu Thr Ile Cys Gly Trp Asp Phe Gly Phe Arg Arg
                580             585             590

Asn Asn Lys Phe Asp Leu Lys Lys Thr Arg Val Leu Leu Gly Asn Glu
                595             600             605

Ser Cys Thr Leu Thr Leu Ser Glu Ser Thr Met Asn Thr Leu Lys Cys
610             615             620

Thr Val Gly Pro Ala Met Asn Lys His Phe Asn Met Ser Ile Ile Ile
625             630             635             640

Ser Asn Gly His Gly Thr Thr Gln Tyr Ser Thr Phe Ser Tyr Val Asp
                645             650             655

Pro Val Ile Thr Ser Ile Ser Pro Lys Tyr Gly Pro Met Ala Gly Gly
                660             665             670

Thr Leu Leu Thr Leu Thr Gly Asn Tyr Leu Asn Ser Gly Asn Ser Arg
                675             680             685

His Ile Ser Ile Gly Gly Lys Thr Cys Thr Leu Lys Ser Val Ser Asn
690             695             700

Ser Ile Leu Glu Cys Tyr Thr Pro Ala Gln Thr Ile Ser Thr Glu Phe
705             710             715             720

Ala Val Lys Leu Lys Ile Asp Leu Ala Asn Arg Glu Thr Ser Ile Phe
                725             730             735

Ser Tyr Arg Glu Asp Pro Ile Val Tyr Glu Ile His Pro Thr Lys Ser
                740             745             750

Phe Ile Ser Gly Gly Ser Thr Ile Thr Gly Val Gly Lys Asn Leu Asn
                755             760             765

Ser Val Ser Val Pro Arg Met Val Ile Asn Val His Glu Ala Gly Arg
770             775             780

Asn Phe Thr Val Ala Cys Gln His Arg Ser Asn Ser Glu Ile Ile Cys
785             790             795             800

Cys Thr Thr Pro Ser Leu Gln Gln Leu Asn Leu Gln Leu Pro Leu Lys
                805             810             815

Thr Lys Ala Phe Phe Met Leu Asp Gly Ile Leu Ser Lys Tyr Phe Asp
                820             825             830

Leu Ile Tyr Val His Asn Pro Val Phe Lys Pro Phe Glu Lys Pro Val
                835             840             845

Met Ile Ser Met Gly Asn Glu Asn Val Leu Glu Ile Lys Gly Asn Asp
850             855             860

Ile Asp Pro Glu Ala Val Lys Gly Glu Val Leu Lys Val Gly Asn Lys
865             870             875             880

Ser Cys Glu Asn Ile His Leu His Ser Glu Ala Val Leu Cys Thr Val
                885             890             895

Pro Asn Asp Leu Leu Lys Leu Asn Ser Glu Leu Asn Ile Glu Trp Lys
                900             905             910

Gln Ala Ile Ser Ser Thr Val Leu Gly Lys Val Ile Val Gln Pro Asp
                915             920             925

Gln Asn Phe Thr Gly Leu Ile Ala Gly Val Val Ser Ile Ser Thr Ala
                930             935             940

Leu Leu Leu Leu Leu Gly Phe Phe Leu Trp Leu Lys Lys Arg Lys Gln
945             950             955             960
```

```
Ile Lys Asp Leu Gly Ser Glu Leu Val Arg Tyr Asp Ala Arg Val His
            965                 970                 975

Thr Pro His Leu Asp Arg Leu Val Ser Ala Arg Ser Val Ser Pro Thr
            980                 985                 990

Thr Glu Met Val Ser Asn Glu Ser Val Asp Tyr Arg Ala Thr Phe Pro
            995                 1000                1005

Glu Asp Gln Phe Pro Asn Ser Ser Gln Asn Gly Ser Cys Arg Gln
        1010                1015                1020

Val Gln Tyr Pro Leu Thr Asp Met Ser Pro Ile Leu Thr Ser Gly
        1025                1030                1035

Asp Ser Asp Ile Ser Ser Pro Leu Leu Gln Asn Thr Val His Ile
        1040                1045                1050

Asp Leu Ser Ala Leu Asn Pro Glu Leu Val Gln Ala Val Gln His
        1055                1060                1065

Val Val Ile Gly Pro Ser Ser Leu Ile Val His Phe Asn Glu Val
        1070                1075                1080

Ile Gly Arg Gly His Phe Gly Cys Val Tyr His Gly Thr Leu Leu
        1085                1090                1095

Asp Asn Asp Gly Lys Lys Ile His Cys Ala Val Lys Ser Leu Asn
        1100                1105                1110

Arg Ile Thr Asp Ile Gly Glu Val Ser Gln Phe Leu Thr Glu Gly
        1115                1120                1125

Ile Ile Met Lys Asp Phe Ser His Pro Asn Val Leu Ser Leu Leu
        1130                1135                1140

Gly Ile Cys Leu Arg Ser Glu Gly Ser Pro Leu Val Val Leu Pro
        1145                1150                1155

Tyr Met Lys His Gly Asp Leu Arg Asn Phe Ile Arg Asn Glu Thr
        1160                1165                1170

His Asn Pro Thr Val Lys Asp Leu Ile Gly Phe Gly Leu Gln Val
        1175                1180                1185

Ala Lys Gly Met Lys Tyr Leu Ala Ser Lys Lys Phe Val His Arg
        1190                1195                1200

Asp Leu Ala Ala Arg Asn Cys Met Leu Asp Glu Lys Phe Thr Val
        1205                1210                1215

Lys Val Ala Asp Phe Gly Leu Ala Arg Asp Met Tyr Asp Lys Glu
        1220                1225                1230

Tyr Tyr Ser Val His Asn Lys Thr Gly Ala Lys Leu Pro Val Lys
        1235                1240                1245

Trp Met Ala Leu Glu Ser Leu Gln Thr Gln Lys Phe Thr Thr Lys
        1250                1255                1260

Ser Asp Val Trp Ser Phe Gly Val Leu Leu Trp Glu Leu Met Thr
        1265                1270                1275

Arg Gly Ala Pro Pro Tyr Pro Asp Val Asn Thr Phe Asp Ile Thr
        1280                1285                1290

Val Tyr Leu Leu Gln Gly Arg Arg Leu Leu Gln Pro Glu Tyr Cys
        1295                1300                1305

Pro Asp Pro Leu Tyr Glu Val Met Leu Lys Cys Trp His Pro Lys
        1310                1315                1320

Ala Glu Met Arg Pro Ser Phe Ser Glu Leu Val Ser Arg Ile Ser
        1325                1330                1335

Ala Ile Phe Ser Thr Phe Ile Gly Glu His Tyr Val His Val Asn
        1340                1345                1350
```

```
Ala Thr Tyr Val Asn Val Lys Cys Val Ala Pro Tyr Pro Ser Leu
    1355                1360                1365

Leu Ser Ser Glu Asp Asn Ala Asp Asp Glu Val Asp Thr Arg Pro
1370                1375                1380

Ala Ser Phe Trp Glu Thr Ser
    1385                1390

<210> SEQ ID NO 19
<211> LENGTH: 1381
<212> TYPE: PRT
<213> ORGANISM: Macaca fascicularis

<400> SEQUENCE: 19

Met Lys Ala Pro Ala Val Leu Val Pro Gly Ile Leu Val Leu Leu Phe
1               5                   10                  15

Thr Leu Val Gln Arg Ser Asn Gly Glu Cys Lys Glu Ala Leu Ala Lys
                20                  25                  30

Ser Glu Met Asn Val Asn Met Lys Tyr Gln Leu Pro Asn Phe Thr Ala
            35                  40                  45

Glu Thr Ala Ile Gln Asn Val Ile Leu His Glu His Ile Phe Leu
50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Asn Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro His
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Ile His Ala Phe Glu Ser Asn
                245                 250                 255

Asn Phe Ile Tyr Phe Leu Thr Val Gln Arg Glu Thr Leu Asn Ala Gln
            260                 265                 270

Thr Phe His Thr Arg Ile Ile Arg Phe Cys Ser Leu Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335
```

```
Leu Asn Asp Asp Ile Leu Phe Gly Val Phe Ala Gln Ser Lys Pro Asp
                340                 345                 350

Ser Ala Glu Pro Met Asp Arg Ser Ala Met Cys Ala Phe Pro Ile Lys
                355                 360                 365

Tyr Val Asn Asp Phe Phe Asn Lys Ile Val Lys Asn Asn Val Arg
        370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Ala Glu Phe Thr Thr Ala Leu Gln Arg Val Asp Leu Phe Met Gly
                420                 425                 430

Gln Phe Ser Glu Val Leu Leu Thr Ser Ile Ser Thr Phe Val Lys Gly
                435                 440                 445

Asp Leu Thr Ile Ala Asn Leu Gly Thr Ser Glu Gly Arg Phe Met Gln
        450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Pro Leu
                485                 490                 495

Asn Gln Asn Gly Tyr Thr Leu Val Val Thr Gly Lys Lys Ile Thr Lys
                500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
        530                 535                 540

Cys Val Arg Ser Glu Glu Cys Pro Ser Gly Thr Trp Thr Gln Gln Ile
545                 550                 555                 560

Cys Leu Pro Ala Ile Tyr Lys Val Phe Pro Thr Ser Ala Pro Leu Glu
                565                 570                 575

Gly Gly Thr Arg Leu Thr Ile Cys Gly Trp Asp Phe Gly Phe Arg Arg
                580                 585                 590

Asn Asn Lys Phe Asp Leu Lys Lys Thr Arg Val Leu Leu Gly Asn Glu
                595                 600                 605

Ser Cys Thr Leu Thr Leu Ser Glu Ser Thr Met Asn Thr Leu Lys Cys
        610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Ile Ile Thr Ser Ile Ser Pro Lys Tyr Gly Pro Met Ala Gly Gly
                660                 665                 670

Thr Leu Leu Thr Leu Thr Gly Asn Tyr Leu Asn Ser Gly Asn Ser Arg
                675                 680                 685

His Ile Ser Ile Gly Gly Lys Thr Cys Thr Leu Lys Ser Val Ser Asn
        690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
                740                 745                 750
```

```
Phe Ile Ser Gly Gly Ser Thr Ile Thr Gly Val Gly Lys Asn Leu His
            755                 760                 765

Ser Val Ser Val Pro Arg Met Val Ile Asn Val His Glu Ala Gly Arg
    770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
            820                 825                 830

Leu Ile Tyr Val His Asn Pro Val Phe Lys Pro Phe Glu Lys Pro Val
            835                 840                 845

Met Ile Ser Met Gly Asn Glu Asn Val Leu Glu Ile Lys Gly Asn Asp
    850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
            900                 905                 910

Gln Ala Ile Ser Ser Thr Val Leu Gly Lys Val Ile Val Gln Pro Asp
            915                 920                 925

Gln Asn Phe Thr Gly Leu Ile Ala Gly Val Val Ser Ile Ser Ile Ala
            930                 935                 940

Leu Leu Leu Leu Leu Gly Leu Phe Leu Trp Leu Lys Lys Arg Lys Gln
945                 950                 955                 960

Ile Lys Asp Leu Gly Ser Glu Leu Val Arg Tyr Asp Ala Arg Val His
                965                 970                 975

Thr Pro His Leu Asp Arg Leu Val Ser Ala Arg Ser Val Ser Pro Thr
            980                 985                 990

Thr Glu Met Val Ser Asn Glu Ser  Val Asp Tyr Arg Ala  Thr Phe Pro
            995                 1000                1005

Glu Asp  Gln Phe Pro Asn Ser  Ser Gln Asn Gly Ser  Cys Arg Gln
    1010                1015                1020

Val Gln  Tyr Pro Leu Thr Asp  Met Ser Pro Ile Leu  Thr Ser Gly
    1025                1030                1035

Asp Ser  Asp Ile Ser Ser Pro  Leu Leu Gln Asn Thr  Val His Ile
    1040                1045                1050

Asp Leu  Ser Ala Leu Asn Pro  Glu Leu Val Gln Ala  Val Gln His
    1055                1060                1065

Val Val  Ile Gly Pro Ser Ser  Leu Ile Val His Phe  Asn Glu Val
    1070                1075                1080

Ile Gly  Arg Gly His Phe Gly  Cys Val Tyr His Gly  Thr Leu Leu
    1085                1090                1095

Asp Asn  Asp Gly Lys Lys Ile  His Cys Ala Val Lys  Ser Leu Asn
    1100                1105                1110

Arg Ile  Thr Asp Ile Gly Glu  Val Ser Gln Phe Leu  Thr Glu Gly
    1115                1120                1125

Ile Ile  Met Lys Asp Phe Ser  His Pro Asn Val Leu  Ser Leu Leu
    1130                1135                1140

Gly Ile  Cys Leu Arg Ser Glu  Gly Ser Pro Leu Val  Val Leu Pro
    1145                1150                1155

Tyr Met  Lys His Gly Asp Leu  Arg Asn Phe Ile Arg  Asn Glu Thr
```

```
                    1160                1165                1170

His Asn Pro Thr Val Lys Asp Leu Ile Gly Phe Gly Leu Gln Val
    1175                1180                1185

Ala Lys Gly Met Lys Tyr Leu Ala Ser Lys Lys Phe Val His Arg
    1190                1195                1200

Asp Leu Ala Ala Arg Asn Cys Met Leu Asp Glu Lys Phe Thr Val
    1205                1210                1215

Lys Val Ala Asp Phe Gly Leu Ala Arg Asp Met Tyr Asp Lys Glu
    1220                1225                1230

Tyr Tyr Ser Val His Asn Lys Thr Gly Ala Lys Leu Pro Val Lys
    1235                1240                1245

Trp Met Ala Leu Glu Ser Leu Gln Thr Gln Lys Phe Thr Thr Lys
    1250                1255                1260

Ser Asp Val Trp Ser Phe Gly Val Leu Leu Trp Glu Leu Met Thr
    1265                1270                1275

Arg Gly Ala Pro Pro Tyr Pro Asp Val Asn Thr Phe Asp Ile Thr
    1280                1285                1290

Val Tyr Leu Leu Gln Gly Arg Arg Leu Leu Gln Pro Glu Tyr Cys
    1295                1300                1305

Pro Asp Pro Leu Tyr Glu Val Met Leu Lys Cys Trp His Pro Lys
    1310                1315                1320

Ala Glu Met Arg Pro Ser Phe Ser Glu Leu Val Ser Arg Ile Ser
    1325                1330                1335

Ala Ile Phe Ser Thr Phe Ile Gly Glu His Tyr Val His Val Asn
    1340                1345                1350

Ala Thr Tyr Val Asn Val Lys Cys Val Ala Pro Tyr Pro Ser Leu
    1355                1360                1365

Leu Ser Ser Glu Asp Asn Ala Asp Asp Glu Val Asp Thr
    1370                1375                1380

<210> SEQ ID NO 20
<211> LENGTH: 5
<212> TYPE: PRT
<213> ORGANISM: Homo sapiens

<400> SEQUENCE: 20

Arg Asp Glu Leu Thr
1               5

<210> SEQ ID NO 21
<211> LENGTH: 4
<212> TYPE: PRT
<213> ORGANISM: Homo sapiens

<400> SEQUENCE: 21

Arg Glu Glu Met
1

<210> SEQ ID NO 22
<211> LENGTH: 10
<212> TYPE: PRT
<213> ORGANISM: Artificial Sequence
<220> FEATURE:
<223> OTHER INFORMATION: anti-C-MET antibody molecule or antigen-binding
      portion HCDR1
<220> FEATURE:
<221> NAME/KEY: misc_feature
<222> LOCATION: (3)..(3)
<223> OTHER INFORMATION: Xaa is Ile or or any other amino acid
<220> FEATURE:
```

```
<221> NAME/KEY: misc_feature
<222> LOCATION: (6)..(6)
<223> OTHER INFORMATION: Xaa is Ala or any other amino acid
<220> FEATURE:
<221> NAME/KEY: misc_feature
<222> LOCATION: (8)..(8)
<223> OTHER INFORMATION: Xaa is Tyr or any other amino acid

<400> SEQUENCE: 22

Gly Tyr Xaa Phe Thr Xaa Tyr Xaa Met His
1               5                   10

<210> SEQ ID NO 23
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2
<220> FEATURE:
<221> NAME/KEY: misc_feature
<222> LOCATION: (3)..(3)
<223> OTHER INFORMATION: Xaa is Trp or any other amino acid
<220> FEATURE:
<221> NAME/KEY: misc_feature
<222> LOCATION: (5)..(5)
<223> OTHER INFORMATION: Xaa is Lys or any other amino acid
<220> FEATURE:
<221> NAME/KEY: misc_feature
<222> LOCATION: (7)..(7)
<223> OTHER INFORMATION: Xaa is Asn or any other amino acid
<220> FEATURE:
<221> NAME/KEY: misc_feature
<222> LOCATION: (8)..(8)
<223> OTHER INFORMATION: Xaa is Asn or any other amino acid
<220> FEATURE:
<221> NAME/KEY: misc_feature
<222> LOCATION: (10)..(10)
<223> OTHER INFORMATION: Xaa is Leu or any other amino acid
<220> FEATURE:
<221> NAME/KEY: misc_feature
<222> LOCATION: (11)..(11)
<223> OTHER INFORMATION: Xaa is Ala or any other amino acid
<220> FEATURE:
<221> NAME/KEY: misc_feature
<222> LOCATION: (12)..(12)
<223> OTHER INFORMATION: Xaa is Asn or any other amino acid

<400> SEQUENCE: 23

Met Gly Xaa Ile Xaa Pro Xaa Xaa Gly Xaa Xaa Xaa Tyr Ala Gln Lys
1               5                   10                  15

Phe Gln Gly

<210> SEQ ID NO 24
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion HCDR3
<220> FEATURE:
<221> NAME/KEY: misc_feature
<222> LOCATION: (1)..(1)
<223> OTHER INFORMATION: Xaa is Ser or any other amino acid
<220> FEATURE:
<221> NAME/KEY: misc_feature
<222> LOCATION: (6)..(6)
<223> OTHER INFORMATION: Xaa is Glu or any other amino acid
<220> FEATURE:
<221> NAME/KEY: misc_feature
<222> LOCATION: (7)..(7)
<223> OTHER INFORMATION: Xaa is Phe or any other amino acid
<220> FEATURE:
<221> NAME/KEY: misc_feature
```

```
<222> LOCATION: (9)..(9)
<223> OTHER INFORMATION: Xaa is Tyr or any other amino acid

<400> SEQUENCE: 24

Xaa Glu Ile Thr Thr Xaa Xaa Asp Xaa
1               5

<210> SEQ ID NO 25
<211> LENGTH: 10
<212> TYPE: PRT
<213> ORGANISM: Artificial Sequence
<220> FEATURE:
<223> OTHER INFORMATION: 224G11 murine/humanized antibody HCDR1

<400> SEQUENCE: 25

Gly Tyr Ile Phe Thr Ala Tyr Thr Met His
1               5                   10

<210> SEQ ID NO 26
<211> LENGTH: 19
<212> TYPE: PRT
<213> ORGANISM: Artificial Sequence
<220> FEATURE:
<223> OTHER INFORMATION: 224G11 murine/humanized antibody HCDR2

<400> SEQUENCE: 26

Met Gly Trp Ile Lys Pro Asn Asn Gly Leu Ala Asn Tyr Ala Gln Lys
1               5                   10                  15

Phe Gln Gly

<210> SEQ ID NO 27
<211> LENGTH: 9
<212> TYPE: PRT
<213> ORGANISM: Artificial Sequence
<220> FEATURE:
<223> OTHER INFORMATION: 224G11 murine/humanized antibody HCDR3

<400> SEQUENCE: 27

Ser Glu Ile Thr Thr Glu Phe Asp Tyr
1               5

<210> SEQ ID NO 28
<211> LENGTH: 15
<212> TYPE: PRT
<213> ORGANISM: Artificial Sequence
<220> FEATURE:
<223> OTHER INFORMATION: anti-C-MET antibody molecule or antigen-binding
      portion LCDR1
<220> FEATURE:
<221> NAME/KEY: misc_feature
<222> LOCATION: (7)..(7)
<223> OTHER INFORMATION: Xaa is Asp or any other amino acid
<220> FEATURE:
<221> NAME/KEY: misc_feature
<222> LOCATION: (11)..(11)
<223> OTHER INFORMATION: Xaa is Asn or any other amino acid
<220> FEATURE:
<221> NAME/KEY: misc_feature
<222> LOCATION: (13)..(13)
<223> OTHER INFORMATION: Xaa is Phe or any other amino acid
<220> FEATURE:
<221> NAME/KEY: misc_feature
<222> LOCATION: (15)..(15)
<223> OTHER INFORMATION: Xaa is His or any other amino acid

<400> SEQUENCE: 28

Arg Ala Ser Gln Ser Val Xaa Ser Tyr Ala Xaa Ser Xaa Leu Xaa
1               5                   10                  15
```

```
<210> SEQ ID NO 29
<211> LENGTH: 7
<212> TYPE: PRT
<213> ORGANISM: Artificial Sequence
<220> FEATURE:
<223> OTHER INFORMATION: anti-C-MET antibody molecule or antigen-binding
      portion LCDR2
<220> FEATURE:
<221> NAME/KEY: misc_feature
<222> LOCATION: (1)..(1)
<223> OTHER INFORMATION: Xaa is Arg or any other amino acid
<220> FEATURE:
<221> NAME/KEY: misc_feature
<222> LOCATION: (2)..(2)
<223> OTHER INFORMATION: Xaa is Ala or any other amino acid
<220> FEATURE:
<221> NAME/KEY: misc_feature
<222> LOCATION: (4)..(4)
<223> OTHER INFORMATION: Xaa is Thr or any other amino acid
<220> FEATURE:
<221> NAME/KEY: misc_feature
<222> LOCATION: (7)..(7)
<223> OTHER INFORMATION: Xaa is Ser or any other amino acid

<400> SEQUENCE: 29

Xaa Xaa Ser Xaa Arg Glu Xaa
1               5

<210> SEQ ID NO 30
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion LCDR3
<220> FEATURE:
<221> NAME/KEY: misc_feature
<222> LOCATION: (3)..(3)
<223> OTHER INFORMATION: Xaa is Ser or any other amino acid
<220> FEATURE:
<221> NAME/KEY: misc_feature
<222> LOCATION: (4)..(4)
<223> OTHER INFORMATION: Xaa is Lys or any other amino acid
<220> FEATURE:
<221> NAME/KEY: misc_feature
<222> LOCATION: (5)..(5)
<223> OTHER INFORMATION: Xaa is Glu or any other amino acid
<220> FEATURE:
<221> NAME/KEY: misc_feature
<222> LOCATION: (6)..(6)
<223> OTHER INFORMATION: Xaa is Asp or any other amino acid

<400> SEQUENCE: 30

Gln Gln Xaa Xaa Xaa Xaa Pro Leu Thr
1               5

<210> SEQ ID NO 31
<211> LENGTH: 15
<212> TYPE: PRT
<213> ORGANISM: Artificial Sequence
<220> FEATURE:
<223> OTHER INFORMATION: 224G11 murine/humanized antibody LCDR1

<400> SEQUENCE: 31

Lys Ser Ser Glu Ser Val Asp Ser Tyr Ala Asn Ser Phe Leu His
1               5                   10                  15

<210> SEQ ID NO 32
<211> LENGTH: 7
<212> TYPE: PRT
<213> ORGANISM: Artificial Sequence
<220> FEATURE:
```

<223> OTHER INFORMATION: 224G11 murine/humanized antibody LCDR2

<400> SEQUENCE: 32

Arg Ala Ser Thr Arg Glu Ser
1               5

<210> SEQ ID NO 33
<211> LENGTH: 9
<212> TYPE: PRT
<213> ORGANISM: Artificial Sequence
<220> FEATURE:
<223> OTHER INFORMATION: 224G11 murine/humanized antibody LCDR3

<400> SEQUENCE: 33

Gln Gln Ser Lys Glu Asp Pro Leu Thr
1               5

<210> SEQ ID NO 34
<211> LENGTH: 10
<212> TYPE: PRT
<213> ORGANISM: Artificial Sequence
<220> FEATURE:
<223> OTHER INFORMATION: anti-C-MET antibody molecule or antigen-binding
      portion HCDR1

<400> SEQUENCE: 34

Gly Tyr Thr Phe Thr Ser Tyr Thr Met His
1               5                   10

<210> SEQ ID NO 35
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 35

Met Gly Ile Ile Asn Pro Ser Gly Gly Ser Thr Ser Tyr Ala Gln Lys
1               5                   10                  15

Phe Gln Gly

<210> SEQ ID NO 36
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion HCDR3

<400> SEQUENCE: 36

Gln Glu Ile Thr Thr Glu Phe Asp Tyr
1               5

<210> SEQ ID NO 37
<211> LENGTH: 15
<212> TYPE: PRT
<213> ORGANISM: Artificial Sequence
<220> FEATURE:
<223> OTHER INFORMATION: anti-C-MET antibody molecule or antigen-binding
      portion LCDR1

<400> SEQUENCE: 37

Arg Ala Ser Gln Ser Val Ser Ser Tyr Ala Asn Ser Tyr Leu His
1               5                   10                  15

```
<210> SEQ ID NO 38
<211> LENGTH: 7
<212> TYPE: PRT
<213> ORGANISM: Artificial Sequence
<220> FEATURE:
<223> OTHER INFORMATION: anti-C-MET antibody molecule or antigen-binding
      portion LCDR2

<400> SEQUENCE: 38

Arg Gly Ser Thr Arg Glu Ser
1               5

<210> SEQ ID NO 39
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion LCDR3

<400> SEQUENCE: 39

Gln Gln Ser Lys Ser Glu Pro Leu Thr
1               5

<210> SEQ ID NO 40
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 40

Met Gly Trp Ile Asn Pro Ser Gly Gly Ser Thr Ser Tyr Ala Gln Lys
1               5                   10                  15

Phe Gln Gly

<210> SEQ ID NO 41
<211> LENGTH: 10
<212> TYPE: PRT
<213> ORGANISM: Artificial Sequence
<220> FEATURE:
<223> OTHER INFORMATION: anti-C-MET antibody molecule or antigen-binding
      portion HCDR1

<400> SEQUENCE: 41

Gly Tyr Thr Phe Thr Ser Tyr Ala Met His
1               5                   10

<210> SEQ ID NO 42
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 42

Met Gly Trp Ile Asn Pro Asn Gly Gly Ser Thr Ser Tyr Ala Gln Lys
1               5                   10                  15

Phe Gln Gly

<210> SEQ ID NO 43
<211> LENGTH: 10
<212> TYPE: PRT
<213> ORGANISM: Artificial Sequence
<220> FEATURE:
```

```
<223> OTHER INFORMATION: anti-C-MET antibody molecule or antigen-binding
      portion HCDR1

<400> SEQUENCE: 43

Gly Tyr Ile Phe Thr Ser Tyr Ser Met His
1               5                   10

<210> SEQ ID NO 44
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 44

Met Gly Trp Ile Asn Pro Ser Asn Gly Leu Ala Asn Tyr Ala Gln Lys
1               5                   10                  15

Phe Gln Gly

<210> SEQ ID NO 45
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion HCDR3

<400> SEQUENCE: 45

Gln Glu Ile Thr Thr Glu Phe Asp Ile
1               5

<210> SEQ ID NO 46
<211> LENGTH: 15
<212> TYPE: PRT
<213> ORGANISM: Artificial Sequence
<220> FEATURE:
<223> OTHER INFORMATION: anti-C-MET antibody molecule or antigen-binding
      portion LCDR1

<400> SEQUENCE: 46

Arg Ala Ser Gln Ser Val Glu Ser Tyr Ala Gln Ser Tyr Leu His
1               5                   10                  15

<210> SEQ ID NO 47
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion LCDR3

<400> SEQUENCE: 47

Gln Gln Ser Lys Ser Asp Pro Leu Thr
1               5

<210> SEQ ID NO 48
<211> LENGTH: 10
<212> TYPE: PRT
<213> ORGANISM: Artificial Sequence
<220> FEATURE:
<223> OTHER INFORMATION: anti-C-MET antibody molecule or antigen-binding
      portion HCDR1

<400> SEQUENCE: 48

Gly Tyr Ile Phe Thr Ser Tyr Thr Met His
1               5                   10
```

```
<210> SEQ ID NO 49
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 49

Met Gly Trp Ile Asn Pro Asn Gly Gly Leu Ala Ser Tyr Ala Gln Lys
1               5                   10                  15

Phe Gln Gly

<210> SEQ ID NO 50
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion HCDR3

<400> SEQUENCE: 50

Ser Glu Ile Thr Thr Glu Gln Asp Tyr
1               5

<210> SEQ ID NO 51
<211> LENGTH: 15
<212> TYPE: PRT
<213> ORGANISM: Artificial Sequence
<220> FEATURE:
<223> OTHER INFORMATION: anti-C-MET antibody molecule or antigen-binding
      portion LCDR1

<400> SEQUENCE: 51

Arg Ala Ser Gln Ser Val Asp Ser Tyr Ala Asn Ser Tyr Leu His
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: anti-C-MET antibody molecule or antigen-binding
      portion LCDR1

<400> SEQUENCE: 52

Arg Ala Ser Gln Ser Val Glu Ser Tyr Ala Asn Ser Tyr Leu His
1               5                   10                  15

<210> SEQ ID NO 53
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion LCDR3

<400> SEQUENCE: 53

Gln Gln Tyr Gly Ser Glu Pro Leu Thr
1               5

<210> SEQ ID NO 54
<211> LENGTH: 19
<212> TYPE: PRT
<213> ORGANISM: Artificial Sequence
<220> FEATURE:
```

```
<223> OTHER INFORMATION: anti-C-MET antibody molecule or antigen-binding
      portion HCDR2

<400> SEQUENCE: 54

Met Gly Trp Ile Asn Pro Ser Gly Gly Leu Ala Asn Tyr Ala Gln Lys
1               5                   10                  15

Phe Gln Gly

<210> SEQ ID NO 55
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion HCDR3

<400> SEQUENCE: 55

Ser Glu Ile Thr Thr Asp Phe Asp Tyr
1               5

<210> SEQ ID NO 56
<211> LENGTH: 7
<212> TYPE: PRT
<213> ORGANISM: Artificial Sequence
<220> FEATURE:
<223> OTHER INFORMATION: anti-C-MET antibody molecule or antigen-binding
      portion LCDR2

<400> SEQUENCE: 56

Arg Gly Ser Thr Arg Glu Thr
1               5

<210> SEQ ID NO 57
<211> LENGTH: 15
<212> TYPE: PRT
<213> ORGANISM: Artificial Sequence
<220> FEATURE:
<223> OTHER INFORMATION: anti-C-MET antibody molecule or antigen-binding
      portion LCDR1

<400> SEQUENCE: 57

Arg Ala Ser Gln Ser Val Ser Ser Tyr Ala Gln Ser Tyr Leu His
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: anti-C-MET antibody molecule or antigen-binding
      portion consensus LCDR1

<400> SEQUENCE: 58

Lys Ser Ser Glu Ser Val Asp Ser Tyr Ala Asn Ser Phe Leu His
1               5                   10                  15

<210> SEQ ID NO 59
<211> LENGTH: 7
<212> TYPE: PRT
<213> ORGANISM: Artificial Sequence
<220> FEATURE:
<223> OTHER INFORMATION: anti-C-MET antibody molecule or antigen-binding
      portion consensus LCDR2

<400> SEQUENCE: 59

Arg Ala Ser Thr Arg Glu Ser
1               5
```

<210> SEQ ID NO 60
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion consensus LCDR3

<400> SEQUENCE: 60

Gln Gln Ser Lys Glu Asp Pro Leu Thr
1               5

<210> SEQ ID NO 61
<211> LENGTH: 10
<212> TYPE: PRT
<213> ORGANISM: Artificial Sequence
<220> FEATURE:
<223> OTHER INFORMATION: anti-C-MET antibody molecule or antigen-binding
      portion consensus HCDR1

<400> SEQUENCE: 61

Gly Tyr Ile Phe Thr Ala Tyr Thr Met His
1               5                   10

<210> SEQ ID NO 62
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion consensus HCDR2

<400> SEQUENCE: 62

Met Gly Trp Ile Lys Pro Asn Asn Gly Leu Ala Asn Tyr Ala Gln Lys
1               5                   10                  15

Phe Gln Gly

<210> SEQ ID NO 63
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion consensus HCDR3

<400> SEQUENCE: 63

Ser Glu Ile Thr Thr Glu Phe Asp Tyr
1               5

<210> SEQ ID NO 64
<211> LENGTH: 10
<212> TYPE: PRT
<213> ORGANISM: Artificial Sequence
<220> FEATURE:
<223> OTHER INFORMATION: anti-C-MET antibody molecule or antigen-binding
      portion HCDR1
<220> FEATURE:
<221> NAME/KEY: misc_feature
<222> LOCATION: (3)..(3)
<223> OTHER INFORMATION: Xaa is Ile or Thr
<220> FEATURE:
<221> NAME/KEY: misc_feature
<222> LOCATION: (6)..(6)
<223> OTHER INFORMATION: Xaa is Ala or Ser
<220> FEATURE:
<221> NAME/KEY: misc_feature
<222> LOCATION: (8)..(8)
<223> OTHER INFORMATION: Xaa is Tyr Ser, Thr or Ala

```
<400> SEQUENCE: 64

Gly Tyr Xaa Phe Thr Xaa Tyr Xaa Met His
1               5                   10

<210> SEQ ID NO 65
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2
<220> FEATURE:
<221> NAME/KEY: misc_feature
<222> LOCATION: (3)..(3)
<223> OTHER INFORMATION: Xaa is Trp or Ile
<220> FEATURE:
<221> NAME/KEY: misc_feature
<222> LOCATION: (5)..(5)
<223> OTHER INFORMATION: Xaa is Lys or Asn
<220> FEATURE:
<221> NAME/KEY: misc_feature
<222> LOCATION: (7)..(7)
<223> OTHER INFORMATION: Xaa is Asn or Ser
<220> FEATURE:
<221> NAME/KEY: misc_feature
<222> LOCATION: (8)..(8)
<223> OTHER INFORMATION: Xaa is Asn or Gly
<220> FEATURE:
<221> NAME/KEY: misc_feature
<222> LOCATION: (10)..(10)
<223> OTHER INFORMATION: Xaa is Leu or Ser
<220> FEATURE:
<221> NAME/KEY: misc_feature
<222> LOCATION: (11)..(11)
<223> OTHER INFORMATION: Xaa is Ala or Thr
<220> FEATURE:
<221> NAME/KEY: misc_feature
<222> LOCATION: (12)..(12)
<223> OTHER INFORMATION: Xaa is Asn or Ser

<400> SEQUENCE: 65

Met Gly Xaa Ile Xaa Pro Xaa Xaa Gly Xaa Xaa Xaa Tyr Ala Gln Lys
1               5                   10                  15

Phe Gln Gly

<210> SEQ ID NO 66
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion HCDR3
<220> FEATURE:
<221> NAME/KEY: misc_feature
<222> LOCATION: (1)..(1)
<223> OTHER INFORMATION: Xaa is Ser, Ala, Glu, His, Met, Gln, Thr or Val
<220> FEATURE:
<221> NAME/KEY: misc_feature
<222> LOCATION: (6)..(6)
<223> OTHER INFORMATION: Xaa is Glu or Asp
<220> FEATURE:
<221> NAME/KEY: misc_feature
<222> LOCATION: (7)..(7)
<223> OTHER INFORMATION: Xaa is Phe or Leu
<220> FEATURE:
<221> NAME/KEY: misc_feature
<222> LOCATION: (9)..(9)
<223> OTHER INFORMATION: Xaa is Tyr, Ala, Glu, Phe, Ile, Lys, Leu, Met,
      Gln, Ser, Val or Trp

<400> SEQUENCE: 66

Xaa Glu Ile Thr Thr Xaa Xaa Asp Xaa
```

```
1               5

<210> SEQ ID NO 67
<211> LENGTH: 10
<212> TYPE: PRT
<213> ORGANISM: Artificial Sequence
<220> FEATURE:
<223> OTHER INFORMATION: anti-C-MET antibody molecule or antigen-binding
      portion HCDR1
<220> FEATURE:
<221> NAME/KEY: misc_feature
<222> LOCATION: (8)..(8)
<223> OTHER INFORMATION: Xaa is Ala, Ser or Thr

<400> SEQUENCE: 67

Gly Tyr Thr Phe Thr Ser Tyr Xaa Met His
1               5                   10

<210> SEQ ID NO 68
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2
<220> FEATURE:
<221> NAME/KEY: misc_feature
<222> LOCATION: (3)..(3)
<223> OTHER INFORMATION: Xaa is Trp or Ile

<400> SEQUENCE: 68

Met Gly Xaa Ile Asn Pro Ser Gly Gly Ser Thr Ser Tyr Ala Gln Lys
1               5                   10                  15

Phe Gln Gly

<210> SEQ ID NO 69
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion HCDR3
<220> FEATURE:
<221> NAME/KEY: misc_feature
<222> LOCATION: (1)..(1)
<223> OTHER INFORMATION: Xaa is Ser, Ala, Glu, Gln or Thr
<220> FEATURE:
<221> NAME/KEY: misc_feature
<222> LOCATION: (6)..(6)
<223> OTHER INFORMATION: Xaa is Glu or Asp
<220> FEATURE:
<221> NAME/KEY: misc_feature
<222> LOCATION: (9)..(9)
<223> OTHER INFORMATION: Xaa is Tyr or Ile

<400> SEQUENCE: 69

Xaa Glu Ile Thr Thr Xaa Phe Asp Xaa
1               5

<210> SEQ ID NO 70
<211> LENGTH: 15
<212> TYPE: PRT
<213> ORGANISM: Artificial Sequence
<220> FEATURE:
<223> OTHER INFORMATION: anti-C-MET antibody molecule or antigen-binding
      portion LCDR1
<220> FEATURE:
<221> NAME/KEY: misc_feature
<222> LOCATION: (7)..(7)
<223> OTHER INFORMATION: Xaa is Asp, Ser or Glu
<220> FEATURE:
```

```
<221> NAME/KEY: misc_feature
<222> LOCATION: (11)..(11)
<223> OTHER INFORMATION: Xaa is Asn or Gln
<220> FEATURE:
<221> NAME/KEY: misc_feature
<222> LOCATION: (13)..(13)
<223> OTHER INFORMATION: Xaa is Phe or Tyr
<220> FEATURE:
<221> NAME/KEY: misc_feature
<222> LOCATION: (15)..(15)
<223> OTHER INFORMATION: Xaa is His or Ala

<400> SEQUENCE: 70

Arg Ala Ser Gln Ser Val Xaa Ser Tyr Ala Xaa Ser Xaa Leu Xaa
1               5                   10                  15

<210> SEQ ID NO 71
<211> LENGTH: 7
<212> TYPE: PRT
<213> ORGANISM: Artificial Sequence
<220> FEATURE:
<223> OTHER INFORMATION: anti-C-MET antibody molecule or antigen-binding
      portion LCDR2
<220> FEATURE:
<221> NAME/KEY: misc_feature
<222> LOCATION: (1)..(1)
<223> OTHER INFORMATION: Xaa is Arg or Ala
<220> FEATURE:
<221> NAME/KEY: misc_feature
<222> LOCATION: (2)..(2)
<223> OTHER INFORMATION: Xaa is Ala or Gly
<220> FEATURE:
<221> NAME/KEY: misc_feature
<222> LOCATION: (4)..(4)
<223> OTHER INFORMATION: Xaa is Thr or Ser
<220> FEATURE:
<221> NAME/KEY: misc_feature
<222> LOCATION: (7)..(7)
<223> OTHER INFORMATION: Xaa is Thr or Ser

<400> SEQUENCE: 71

Xaa Xaa Ser Xaa Arg Glu Xaa
1               5

<210> SEQ ID NO 72
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion LCDR3
<220> FEATURE:
<221> NAME/KEY: misc_feature
<222> LOCATION: (3)..(3)
<223> OTHER INFORMATION: Xaa is Ser or Tyr
<220> FEATURE:
<221> NAME/KEY: misc_feature
<222> LOCATION: (4)..(4)
<223> OTHER INFORMATION: Xaa is Lys or Gly
<220> FEATURE:
<221> NAME/KEY: misc_feature
<222> LOCATION: (5)..(5)
<223> OTHER INFORMATION: Xaa is Glu, Asp or Ser
<220> FEATURE:
<221> NAME/KEY: misc_feature
<222> LOCATION: (6)..(6)
<223> OTHER INFORMATION: Xaa is Asp, Ser, Glu or Arg

<400> SEQUENCE: 72

Gln Gln Xaa Xaa Xaa Xaa Pro Leu Thr
1               5

<210> SEQ ID NO 73
```

```
<211> LENGTH: 15
<212> TYPE: PRT
<213> ORGANISM: Artificial Sequence
<220> FEATURE:
<223> OTHER INFORMATION: anti-C-MET antibody molecule or antigen-binding
      portion LCDR1
<220> FEATURE:
<221> NAME/KEY: misc_feature
<222> LOCATION: (7)..(7)
<223> OTHER INFORMATION: Xaa is Asp, Ser or Glu
<220> FEATURE:
<221> NAME/KEY: misc_feature
<222> LOCATION: (11)..(11)
<223> OTHER INFORMATION: Xaa is Asn or Gln

<400> SEQUENCE: 73

Arg Ala Ser Gln Ser Val Xaa Ser Tyr Ala Xaa Ser Tyr Leu His
1               5                   10                  15

<210> SEQ ID NO 74
<211> LENGTH: 7
<212> TYPE: PRT
<213> ORGANISM: Artificial Sequence
<220> FEATURE:
<223> OTHER INFORMATION: anti-C-MET antibody molecule or antigen-binding
      portion LCDR2
<220> FEATURE:
<221> NAME/KEY: misc_feature
<222> LOCATION: (7)..(7)
<223> OTHER INFORMATION: Xaa is Thr or Ser

<400> SEQUENCE: 74

Arg Gly Ser Thr Arg Glu Xaa
1               5

<210> SEQ ID NO 75
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion LCDR3
<220> FEATURE:
<221> NAME/KEY: misc_feature
<222> LOCATION: (3)..(3)
<223> OTHER INFORMATION: Xaa is Ser or Tyr
<220> FEATURE:
<221> NAME/KEY: misc_feature
<222> LOCATION: (4)..(4)
<223> OTHER INFORMATION: Xaa is Lys or Gly
<220> FEATURE:
<221> NAME/KEY: misc_feature
<222> LOCATION: (5)..(5)
<223> OTHER INFORMATION: Xaa is Glu or Ser
<220> FEATURE:
<221> NAME/KEY: misc_feature
<222> LOCATION: (6)..(6)
<223> OTHER INFORMATION: Xaa is Asp, Ser or Glu

<400> SEQUENCE: 75

Gln Gln Xaa Xaa Xaa Xaa Pro Leu Thr
1               5

<210> SEQ ID NO 76
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion LCDR3

<400> SEQUENCE: 76
```

```
Gln Gln Ser Lys Ser Asp Pro Leu Thr
1               5
```

<210> SEQ ID NO 77
<211> LENGTH: 7
<212> TYPE: PRT
<213> ORGANISM: Artificial Sequence
<220> FEATURE:
<223> OTHER INFORMATION: anti-C-MET antibody molecule or antigen-binding
      portion LCDR2

<400> SEQUENCE: 77

```
Arg Ala Ser Thr Arg Glu Thr
1               5
```

<210> SEQ ID NO 78
<211> LENGTH: 10
<212> TYPE: PRT
<213> ORGANISM: Artificial Sequence
<220> FEATURE:
<223> OTHER INFORMATION: anti-C-MET antibody molecule or antigen-binding
      portion HCDR1

<400> SEQUENCE: 78

```
Gly Tyr Thr Phe Thr Ser Tyr Ser Met His
1               5                   10
```

<210> SEQ ID NO 79
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 79

```
Met Gly Trp Ile Asn Pro Asn Gly Gly Leu Thr Asn Tyr Ala Gln Lys
1               5                   10                  15

Phe Arg Gly
```

<210> SEQ ID NO 80
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion HCDR3

<400> SEQUENCE: 80

```
Glu Glu Ile Thr Thr Glu Phe Asp Tyr
1               5
```

<210> SEQ ID NO 81
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 81

```
Met Gly Trp Ile Asn Pro Asn Asn Gly Ser Thr Asn Tyr Ala Gln Lys
1               5                   10                  15

Phe Gln Gly
```

<210> SEQ ID NO 82

```
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion LCDR3

<400> SEQUENCE: 82

Gln Gln Ser Lys Glu Glu Pro Leu Thr
1               5

<210> SEQ ID NO 83
<211> LENGTH: 10
<212> TYPE: PRT
<213> ORGANISM: Artificial Sequence
<220> FEATURE:
<223> OTHER INFORMATION: anti-C-MET antibody molecule or antigen-binding
      portion HCDR1

<400> SEQUENCE: 83

Gly Tyr Ile Phe Thr Ala Tyr Ser Met His
1               5                   10

<210> SEQ ID NO 84
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 84

Met Gly Ile Ile Lys Pro Ser Asn Gly Ser Thr Asn Tyr Ala Gln Lys
1               5                   10                  15

Phe Gln Gly

<210> SEQ ID NO 85
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion HCDR3

<400> SEQUENCE: 85

Ala Glu Ile Thr Thr Glu Phe Asp Tyr
1               5

<210> SEQ ID NO 86
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 86

Met Gly Trp Ile Lys Pro Asn Asn Gly Ser Ala Ser Tyr Ala Gln Lys
1               5                   10                  15

Phe Gln Gly

<210> SEQ ID NO 87
<211> LENGTH: 19
<212> TYPE: PRT
<213> ORGANISM: Artificial Sequence
<220> FEATURE:
<223> OTHER INFORMATION: anti-C-MET antibody molecule or antigen-binding
``` portion HCDR2

<400> SEQUENCE: 87

Met Gly Trp Ile Lys Pro Asn Asn Gly Ser Thr Asn Tyr Ala Gln Lys
1               5                   10                  15

Phe Gln Gly

<210> SEQ ID NO 88
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion HCDR3

<400> SEQUENCE: 88

Thr Glu Ile Thr Thr Glu Phe Asp Tyr
1               5

<210> SEQ ID NO 89
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion LCDR3

<400> SEQUENCE: 89

Gln Gln Ser Gly Ser Ser Pro Leu Thr
1               5

<210> SEQ ID NO 90
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion LCDR3

<400> SEQUENCE: 90

Gln Gln Tyr Gly Ser Ser Pro Leu Thr
1               5

<210> SEQ ID NO 91
<211> LENGTH: 9
<212> TYPE: PRT
<213> ORGANISM: Artificial Sequence
<220> FEATURE:
<223> OTHER INFORMATION: HAF peptide motif

<400> SEQUENCE: 91

Leu Leu Ile Tyr Arg Ala Ser Thr Arg
1               5

<210> SEQ ID NO 92
<211> LENGTH: 9
<212> TYPE: PRT
<213> ORGANISM: Artificial Sequence
<220> FEATURE:
<223> OTHER INFORMATION: HAF peptide motif

<400> SEQUENCE: 92

Ile Tyr Arg Ala Ser Thr Arg Glu Ser
1               5

<210> SEQ ID NO 93

```
<211> LENGTH: 9
<212> TYPE: PRT
<213> ORGANISM: Artificial Sequence
<220> FEATURE:
<223> OTHER INFORMATION: LAF peptide motif

<400> SEQUENCE: 93

Val Ala Val Tyr Tyr Cys Gln Gln Ser
1               5

<210> SEQ ID NO 94
<211> LENGTH: 8
<212> TYPE: PRT
<213> ORGANISM: Artificial Sequence
<220> FEATURE:
<223> OTHER INFORMATION: HAF peptide motif

<400> SEQUENCE: 94

Ile Phe Thr Ala Tyr Thr Met His
1               5

<210> SEQ ID NO 95
<211> LENGTH: 9
<212> TYPE: PRT
<213> ORGANISM: Artificial Sequence
<220> FEATURE:
<223> OTHER INFORMATION: HAF peptide motif

<400> SEQUENCE: 95

Val Tyr Tyr Cys Ala Arg Ser Glu Ile
1               5

<210> SEQ ID NO 96
<211> LENGTH: 9
<212> TYPE: PRT
<213> ORGANISM: Artificial Sequence
<220> FEATURE:
<223> OTHER INFORMATION: LAF peptide motif

<400> SEQUENCE: 96

Met Gly Trp Ile Lys Pro Asn Asn Gly
1               5

<210> SEQ ID NO 97
<211> LENGTH: 9
<212> TYPE: PRT
<213> ORGANISM: Artificial Sequence
<220> FEATURE:
<223> OTHER INFORMATION: HAF peptide motif

<400> SEQUENCE: 97

Ile Phe Thr Ala Tyr Thr Met His Trp
1               5

<210> SEQ ID NO 98
<211> LENGTH: 9
<212> TYPE: PRT
<213> ORGANISM: Artificial Sequence
<220> FEATURE:
<223> OTHER INFORMATION: germline epitope peptide

<400> SEQUENCE: 98

Leu Glu Trp Met Gly Ile Ile Asn Pro
1               5

<210> SEQ ID NO 99
<211> LENGTH: 9
```

```
<212> TYPE: PRT
<213> ORGANISM: Artificial Sequence
<220> FEATURE:
<223> OTHER INFORMATION: germline epitope peptide

<400> SEQUENCE: 99

Met Gly Ile Ile Asn Pro Ser Gly Gly
1               5

<210> SEQ ID NO 100
<211> LENGTH: 10
<212> TYPE: PRT
<213> ORGANISM: Mus musculus

<400> SEQUENCE: 100

Gly Tyr Ile Phe Thr Ala Tyr Thr Met His
1               5                   10

<210> SEQ ID NO 101
<211> LENGTH: 5
<212> TYPE: PRT
<213> ORGANISM: Mus musculus

<400> SEQUENCE: 101

Ala Tyr Thr Met His
1               5

<210> SEQ ID NO 102
<211> LENGTH: 7
<212> TYPE: PRT
<213> ORGANISM: Mus musculus

<400> SEQUENCE: 102

Gly Tyr Ile Phe Thr Ala Tyr
1               5

<210> SEQ ID NO 103
<211> LENGTH: 8
<212> TYPE: PRT
<213> ORGANISM: Mus musculus

<400> SEQUENCE: 103

Gly Tyr Ile Phe Thr Ala Tyr Thr
1               5

<210> SEQ ID NO 104
<211> LENGTH: 12
<212> TYPE: PRT
<213> ORGANISM: Mus musculus

<400> SEQUENCE: 104

Ala Ser Gly Tyr Ile Phe Thr Ala Tyr Thr Met His
1               5                   10

<210> SEQ ID NO 105
<211> LENGTH: 6
<212> TYPE: PRT
<213> ORGANISM: Mus musculus

<400> SEQUENCE: 105

Thr Ala Tyr Thr Met His
1               5

<210> SEQ ID NO 106
<211> LENGTH: 19
```

```
<212> TYPE: PRT
<213> ORGANISM: Mus musculus

<400> SEQUENCE: 106

Met Gly Trp Ile Lys Pro Asn Asn Gly Leu Ala Asn Tyr Ala Gln Lys
1               5                   10                  15

Phe Gln Gly

<210> SEQ ID NO 107
<211> LENGTH: 17
<212> TYPE: PRT
<213> ORGANISM: Mus musculus

<400> SEQUENCE: 107

Trp Ile Lys Pro Asn Asn Gly Leu Ala Asn Tyr Ala Gln Lys Phe Gln
1               5                   10                  15

Gly

<210> SEQ ID NO 108
<211> LENGTH: 6
<212> TYPE: PRT
<213> ORGANISM: Mus musculus

<400> SEQUENCE: 108

Lys Pro Asn Asn Gly Leu
1               5

<210> SEQ ID NO 109
<211> LENGTH: 8
<212> TYPE: PRT
<213> ORGANISM: Mus musculus

<400> SEQUENCE: 109

Ile Lys Pro Asn Asn Gly Leu Ala
1               5

<210> SEQ ID NO 110
<211> LENGTH: 16
<212> TYPE: PRT
<213> ORGANISM: Mus musculus

<400> SEQUENCE: 110

Ile Lys Pro Asn Asn Gly Leu Ala Asn Tyr Ala Gln Lys Phe Gln Gly
1               5                   10                  15

<210> SEQ ID NO 111
<211> LENGTH: 10
<212> TYPE: PRT
<213> ORGANISM: Mus musculus

<400> SEQUENCE: 111

Trp Ile Lys Pro Asn Asn Gly Leu Ala Asn
1               5                   10

<210> SEQ ID NO 112
<211> LENGTH: 12
<212> TYPE: PRT
<213> ORGANISM: Mus musculus

<400> SEQUENCE: 112

Met Gly Trp Ile Lys Pro Asn Asn Gly Leu Ala Asn
1               5                   10
```

```
<210> SEQ ID NO 113
<211> LENGTH: 9
<212> TYPE: PRT
<213> ORGANISM: Mus musculus

<400> SEQUENCE: 113

Ser Glu Ile Thr Thr Glu Phe Asp Tyr
1               5

<210> SEQ ID NO 114
<211> LENGTH: 11
<212> TYPE: PRT
<213> ORGANISM: Mus musculus

<400> SEQUENCE: 114

Ala Arg Ser Glu Ile Thr Thr Glu Phe Asp Tyr
1               5                   10

<210> SEQ ID NO 115
<211> LENGTH: 8
<212> TYPE: PRT
<213> ORGANISM: Mus musculus

<400> SEQUENCE: 115

Ser Glu Ile Thr Thr Glu Phe Asp
1               5

<210> SEQ ID NO 116
<211> LENGTH: 10
<212> TYPE: PRT
<213> ORGANISM: Mus musculus

<400> SEQUENCE: 116

Ala Arg Ser Glu Ile Thr Thr Glu Phe Asp
1               5                   10

<210> SEQ ID NO 117
<211> LENGTH: 15
<212> TYPE: PRT
<213> ORGANISM: Mus musculus

<400> SEQUENCE: 117

Lys Ser Ser Glu Ser Val Asp Ser Tyr Ala Asn Ser Phe Leu His
1               5                   10                  15

<210> SEQ ID NO 118
<211> LENGTH: 10
<212> TYPE: PRT
<213> ORGANISM: Mus musculus

<400> SEQUENCE: 118

Glu Ser Val Asp Ser Tyr Ala Asn Ser Phe
1               5                   10

<210> SEQ ID NO 119
<211> LENGTH: 12
<212> TYPE: PRT
<213> ORGANISM: Mus musculus

<400> SEQUENCE: 119

Ser Ser Glu Ser Val Asp Ser Tyr Ala Asn Ser Phe
1               5                   10

<210> SEQ ID NO 120
<211> LENGTH: 12
```

```
<212> TYPE: PRT
<213> ORGANISM: Mus musculus

<400> SEQUENCE: 120

Val Asp Ser Tyr Ala Asn Ser Phe Leu His Trp Tyr
1               5                   10

<210> SEQ ID NO 121
<211> LENGTH: 7
<212> TYPE: PRT
<213> ORGANISM: Mus musculus

<400> SEQUENCE: 121

Arg Ala Ser Thr Arg Glu Ser
1               5

<210> SEQ ID NO 122
<211> LENGTH: 10
<212> TYPE: PRT
<213> ORGANISM: Mus musculus

<400> SEQUENCE: 122

Leu Leu Ile Tyr Arg Ala Ser Thr Arg Glu
1               5                   10

<210> SEQ ID NO 123
<211> LENGTH: 9
<212> TYPE: PRT
<213> ORGANISM: Mus musculus

<400> SEQUENCE: 123

Gln Gln Ser Lys Glu Asp Pro Leu Thr
1               5

<210> SEQ ID NO 124
<211> LENGTH: 6
<212> TYPE: PRT
<213> ORGANISM: Mus musculus

<400> SEQUENCE: 124

Ser Lys Glu Asp Pro Leu
1               5

<210> SEQ ID NO 125
<211> LENGTH: 8
<212> TYPE: PRT
<213> ORGANISM: Mus musculus

<400> SEQUENCE: 125

Gln Gln Ser Lys Glu Asp Pro Leu
1               5

<210> SEQ ID NO 126
<211> LENGTH: 118
<212> TYPE: PRT
<213> ORGANISM: Artificial Sequence
<220> FEATURE:
<223> OTHER INFORMATION: h224G11-VH IGHV1-2

<400> SEQUENCE: 126

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ala Tyr
            20                  25                  30
```

```
Thr Met His Trp Val Arg Gln Ala Pro Gly Gln Gly Leu Glu Trp Met
            35                  40                  45

Gly Trp Ile Lys Pro Asn Asn Gly Leu Ala Asn Tyr Ala Gln Lys Phe
 50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Glu Ile Thr Thr Glu Phe Asp Tyr Trp Gly Gln Gly Thr
                100                 105                 110

Leu Val Thr Val Ser Ser
            115

<210> SEQ ID NO 127
<211> LENGTH: 118
<212> TYPE: PRT
<213> ORGANISM: Artificial Sequence
<220> FEATURE:
<223> OTHER INFORMATION: VH graft IGHV1-46

<400> SEQUENCE: 127

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ala Tyr
                20                  25                  30

Thr Met His Trp Val Arg Gln Ala Pro Gly Gln Gly Leu Glu Trp Met
            35                  40                  45

Gly Trp Ile Lys Pro Asn Asn Gly Leu Ala Asn Tyr Ala Gln Lys Phe
 50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Glu Ile Thr Thr Glu Phe Asp Tyr Trp Gly Gln Gly Thr
                100                 105                 110

Leu Val Thr Val Ser Ser
            115

<210> SEQ ID NO 128
<211> LENGTH: 111
<212> TYPE: PRT
<213> ORGANISM: Artificial Sequence
<220> FEATURE:
<223> OTHER INFORMATION: h224G11-VL IGKV4-1

<400> SEQUENCE: 128

Asp Ile Val Met Thr Gln Ser Pro Asp Ser Leu Ala Val Ser Leu Gly
1               5                   10                  15

Glu Arg Ala Thr Ile Asn Cys Lys Ser Ser Glu Ser Val Asp Ser Tyr
                20                  25                  30

Ala Asn Ser Phe Leu His Trp Tyr Gln Gln Lys Pro Gly Gln Pro Pro
            35                  40                  45

Lys Leu Leu Ile Tyr Arg Ala Ser Thr Arg Glu Ser Gly Val Pro Asp
 50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Lys
                85                  90                  95
```

Glu Asp Pro Leu Thr Phe Gly Gly Gly Thr Lys Val Glu Ile Lys
            100                 105                 110

<210> SEQ ID NO 129
<211> LENGTH: 111
<212> TYPE: PRT
<213> ORGANISM: Artificial Sequence
<220> FEATURE:
<223> OTHER INFORMATION: VL graft IGKV3-20

<400> SEQUENCE: 129

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Asp Ser Tyr
            20                  25                  30

Ala Asn Ser Phe Leu His Trp Tyr Gln Gln Lys Pro Gly Gln Ala Pro
        35                  40                  45

Arg Leu Leu Ile Tyr Arg Ala Ser Thr Arg Glu Ser Gly Ile Pro Asp
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Asp Pro Leu Thr Phe Gly Gly Gly Thr Lys Val Glu Ile Lys
            100                 105                 110

<210> SEQ ID NO 130
<211> LENGTH: 15
<212> TYPE: PRT
<213> ORGANISM: Artificial Sequence
<220> FEATURE:
<223> OTHER INFORMATION: anti-C-MET antibody molecule or antigen-binding
      portion LCDR1

<400> SEQUENCE: 130

Arg Ala Ser Gln Ser Val Asp Ser Tyr Ala Asn Ser Phe Leu Ala
1               5                   10                  15

<210> SEQ ID NO 131
<211> LENGTH: 15
<212> TYPE: PRT
<213> ORGANISM: Artificial Sequence
<220> FEATURE:
<223> OTHER INFORMATION: anti-C-MET antibody molecule or antigen-binding
      portion LCDR1

<400> SEQUENCE: 131

Arg Ala Ser Gln Ser Val Asp Ser Tyr Ala Asn Ser Phe Leu His
1               5                   10                  15

<210> SEQ ID NO 132
<211> LENGTH: 15
<212> TYPE: PRT
<213> ORGANISM: Artificial Sequence
<220> FEATURE:
<223> OTHER INFORMATION: anti-C-MET antibody molecule or antigen-binding
      portion LCDR1

<400> SEQUENCE: 132

Arg Ala Ser Gln Ser Val Asp Ser Tyr Ala Asn Ser Tyr Leu Ala
1               5                   10                  15

<210> SEQ ID NO 133

```
<211> LENGTH: 15
<212> TYPE: PRT
<213> ORGANISM: Artificial Sequence
<220> FEATURE:
<223> OTHER INFORMATION: anti-C-MET antibody molecule or antigen-binding
      portion LCDR1

<400> SEQUENCE: 133

Arg Ala Ser Gln Ser Val Asp Ser Tyr Ala Gln Ser Phe Leu His
1               5                   10                  15

<210> SEQ ID NO 134
<211> LENGTH: 15
<212> TYPE: PRT
<213> ORGANISM: Artificial Sequence
<220> FEATURE:
<223> OTHER INFORMATION: anti-C-MET antibody molecule or antigen-binding
      portion LCDR1

<400> SEQUENCE: 134

Arg Ala Ser Gln Ser Val Asp Ser Tyr Ala Gln Ser Tyr Leu Ala
1               5                   10                  15

<210> SEQ ID NO 135
<211> LENGTH: 15
<212> TYPE: PRT
<213> ORGANISM: Artificial Sequence
<220> FEATURE:
<223> OTHER INFORMATION: anti-C-MET antibody molecule or antigen-binding
      portion LCDR1

<400> SEQUENCE: 135

Arg Ala Ser Gln Ser Val Asp Ser Tyr Ala Gln Ser Tyr Leu His
1               5                   10                  15

<210> SEQ ID NO 136
<211> LENGTH: 15
<212> TYPE: PRT
<213> ORGANISM: Artificial Sequence
<220> FEATURE:
<223> OTHER INFORMATION: anti-C-MET antibody molecule or antigen-binding
      portion LCDR1

<400> SEQUENCE: 136

Arg Ala Ser Gln Ser Val Glu Ser Tyr Ala Asn Ser Phe Leu Ala
1               5                   10                  15

<210> SEQ ID NO 137
<211> LENGTH: 15
<212> TYPE: PRT
<213> ORGANISM: Artificial Sequence
<220> FEATURE:
<223> OTHER INFORMATION: anti-C-MET antibody molecule or antigen-binding
      portion LCDR1

<400> SEQUENCE: 137

Arg Ala Ser Gln Ser Val Glu Ser Tyr Ala Asn Ser Tyr Leu Ala
1               5                   10                  15

<210> SEQ ID NO 138
<211> LENGTH: 15
<212> TYPE: PRT
<213> ORGANISM: Artificial Sequence
<220> FEATURE:
<223> OTHER INFORMATION: anti-C-MET antibody molecule or antigen-binding
      portion LCDR1

<400> SEQUENCE: 138
```

Arg Ala Ser Gln Ser Val Glu Ser Tyr Ala Gln Ser Phe Leu His
1               5                   10                  15

<210> SEQ ID NO 139
<211> LENGTH: 15
<212> TYPE: PRT
<213> ORGANISM: Artificial Sequence
<220> FEATURE:
<223> OTHER INFORMATION: anti-C-MET antibody molecule or antigen-binding
      portion LCDR1

<400> SEQUENCE: 139

Arg Ala Ser Gln Ser Val Ser Ser Tyr Ala Asn Ser Phe Leu His
1               5                   10                  15

<210> SEQ ID NO 140
<211> LENGTH: 15
<212> TYPE: PRT
<213> ORGANISM: Artificial Sequence
<220> FEATURE:
<223> OTHER INFORMATION: anti-C-MET antibody molecule or antigen-binding
      portion LCDR1

<400> SEQUENCE: 140

Arg Ala Ser Gln Ser Val Ser Ser Tyr Ala Asn Ser Tyr Leu Ala
1               5                   10                  15

<210> SEQ ID NO 141
<211> LENGTH: 15
<212> TYPE: PRT
<213> ORGANISM: Artificial Sequence
<220> FEATURE:
<223> OTHER INFORMATION: anti-C-MET antibody molecule or antigen-binding
      portion LCDR1

<400> SEQUENCE: 141

Arg Ala Ser Gln Ser Val Ser Ser Tyr Ala Gln Ser Phe Leu Ala
1               5                   10                  15

<210> SEQ ID NO 142
<211> LENGTH: 15
<212> TYPE: PRT
<213> ORGANISM: Artificial Sequence
<220> FEATURE:
<223> OTHER INFORMATION: anti-C-MET antibody molecule or antigen-binding
      portion LCDR1

<400> SEQUENCE: 142

Arg Ala Ser Gln Ser Val Ser Ser Tyr Ala Gln Ser Phe Leu His
1               5                   10                  15

<210> SEQ ID NO 143
<211> LENGTH: 7
<212> TYPE: PRT
<213> ORGANISM: Artificial Sequence
<220> FEATURE:
<223> OTHER INFORMATION: anti-C-MET antibody molecule or antigen-binding
      portion LCDR2

<400> SEQUENCE: 143

Ala Ala Ser Thr Arg Glu Ser
1               5

<210> SEQ ID NO 144
<211> LENGTH: 7
<212> TYPE: PRT
<213> ORGANISM: Artificial Sequence
<220> FEATURE:

```
<223> OTHER INFORMATION: anti-C-MET antibody molecule or antigen-binding
      portion LCDR2

<400> SEQUENCE: 144

Ala Gly Ser Thr Arg Glu Ser
1               5

<210> SEQ ID NO 145
<211> LENGTH: 7
<212> TYPE: PRT
<213> ORGANISM: Artificial Sequence
<220> FEATURE:
<223> OTHER INFORMATION: anti-C-MET antibody molecule or antigen-binding
      portion LCDR2

<400> SEQUENCE: 145

Ala Gly Ser Thr Arg Glu Thr
1               5

<210> SEQ ID NO 146
<211> LENGTH: 7
<212> TYPE: PRT
<213> ORGANISM: Artificial Sequence
<220> FEATURE:
<223> OTHER INFORMATION: anti-C-MET antibody molecule or antigen-binding
      portion LCDR2

<400> SEQUENCE: 146

Arg Ala Ser Ser Arg Glu Ser
1               5

<210> SEQ ID NO 147
<211> LENGTH: 7
<212> TYPE: PRT
<213> ORGANISM: Artificial Sequence
<220> FEATURE:
<223> OTHER INFORMATION: anti-C-MET antibody molecule or antigen-binding
      portion LCDR2

<400> SEQUENCE: 147

Arg Ala Ser Ser Arg Glu Thr
1               5

<210> SEQ ID NO 148
<211> LENGTH: 7
<212> TYPE: PRT
<213> ORGANISM: Artificial Sequence
<220> FEATURE:
<223> OTHER INFORMATION: anti-C-MET antibody molecule or antigen-binding
      portion LCDR2

<400> SEQUENCE: 148

Arg Gly Ser Ser Arg Glu Ser
1               5

<210> SEQ ID NO 149
<211> LENGTH: 7
<212> TYPE: PRT
<213> ORGANISM: Artificial Sequence
<220> FEATURE:
<223> OTHER INFORMATION: anti-C-MET antibody molecule or antigen-binding
      portion LCDR2

<400> SEQUENCE: 149

Arg Gly Ser Ser Arg Glu Thr
1               5
```

```
<210> SEQ ID NO 150
<211> LENGTH: 10
<212> TYPE: PRT
<213> ORGANISM: Artificial Sequence
<220> FEATURE:
<223> OTHER INFORMATION: anti-C-MET antibody molecule or antigen-binding
      portion LCDR3

<400> SEQUENCE: 150

Gln Gln Ser Gly Glu Asp Pro Leu Thr Phe
1               5                   10

<210> SEQ ID NO 151
<211> LENGTH: 10
<212> TYPE: PRT
<213> ORGANISM: Artificial Sequence
<220> FEATURE:
<223> OTHER INFORMATION: anti-C-MET antibody molecule or antigen-binding
      portion LCDR3

<400> SEQUENCE: 151

Gln Gln Ser Gly Glu Glu Pro Leu Thr Phe
1               5                   10

<210> SEQ ID NO 152
<211> LENGTH: 10
<212> TYPE: PRT
<213> ORGANISM: Artificial Sequence
<220> FEATURE:
<223> OTHER INFORMATION: anti-C-MET antibody molecule or antigen-binding
      portion LCDR3

<400> SEQUENCE: 152

Gln Gln Ser Gly Glu Ser Pro Leu Thr Phe
1               5                   10

<210> SEQ ID NO 153
<211> LENGTH: 10
<212> TYPE: PRT
<213> ORGANISM: Artificial Sequence
<220> FEATURE:
<223> OTHER INFORMATION: anti-C-MET antibody molecule or antigen-binding
      portion LCDR3

<400> SEQUENCE: 153

Gln Gln Ser Gly Ser Asp Pro Leu Thr Phe
1               5                   10

<210> SEQ ID NO 154
<211> LENGTH: 10
<212> TYPE: PRT
<213> ORGANISM: Artificial Sequence
<220> FEATURE:
<223> OTHER INFORMATION: anti-C-MET antibody molecule or antigen-binding
      portion LCDR3

<400> SEQUENCE: 154

Gln Gln Ser Gly Ser Glu Pro Leu Thr Phe
1               5                   10

<210> SEQ ID NO 155
<211> LENGTH: 10
<212> TYPE: PRT
<213> ORGANISM: Artificial Sequence
<220> FEATURE:
<223> OTHER INFORMATION: anti-C-MET antibody molecule or antigen-binding
      portion LCDR3

<400> SEQUENCE: 155
```

Gln Gln Ser Gly Ser Arg Pro Leu Thr Phe
1               5                   10

<210> SEQ ID NO 156
<211> LENGTH: 10
<212> TYPE: PRT
<213> ORGANISM: Artificial Sequence
<220> FEATURE:
<223> OTHER INFORMATION: anti-C-MET antibody molecule or antigen-binding
      portion LCDR3

<400> SEQUENCE: 156

Gln Gln Ser Gly Ser Ser Pro Leu Thr Phe
1               5                   10

<210> SEQ ID NO 157
<211> LENGTH: 10
<212> TYPE: PRT
<213> ORGANISM: Artificial Sequence
<220> FEATURE:
<223> OTHER INFORMATION: anti-C-MET antibody molecule or antigen-binding
      portion LCDR3

<400> SEQUENCE: 157

Gln Gln Ser Lys Glu Glu Pro Leu Thr Phe
1               5                   10

<210> SEQ ID NO 158
<211> LENGTH: 10
<212> TYPE: PRT
<213> ORGANISM: Artificial Sequence
<220> FEATURE:
<223> OTHER INFORMATION: anti-C-MET antibody molecule or antigen-binding
      portion LCDR3

<400> SEQUENCE: 158

Gln Gln Ser Lys Glu Ser Pro Leu Thr Phe
1               5                   10

<210> SEQ ID NO 159
<211> LENGTH: 10
<212> TYPE: PRT
<213> ORGANISM: Artificial Sequence
<220> FEATURE:
<223> OTHER INFORMATION: anti-C-MET antibody molecule or antigen-binding
      portion LCDR3

<400> SEQUENCE: 159

Gln Gln Ser Lys Ser Asp Pro Leu Thr Phe
1               5                   10

<210> SEQ ID NO 160
<211> LENGTH: 10
<212> TYPE: PRT
<213> ORGANISM: Artificial Sequence
<220> FEATURE:
<223> OTHER INFORMATION: anti-C-MET antibody molecule or antigen-binding
      portion LCDR3

<400> SEQUENCE: 160

Gln Gln Ser Lys Ser Glu Pro Leu Thr Phe
1               5                   10

<210> SEQ ID NO 161
<211> LENGTH: 10
<212> TYPE: PRT
<213> ORGANISM: Artificial Sequence

```
<220> FEATURE:
<223> OTHER INFORMATION: anti-C-MET antibody molecule or antigen-binding
      portion LCDR3

<400> SEQUENCE: 161

Gln Gln Ser Lys Ser Ser Pro Leu Thr Phe
1               5                   10

<210> SEQ ID NO 162
<211> LENGTH: 10
<212> TYPE: PRT
<213> ORGANISM: Artificial Sequence
<220> FEATURE:
<223> OTHER INFORMATION: anti-C-MET antibody molecule or antigen-binding
      portion LCDR3

<400> SEQUENCE: 162

Gln Gln Tyr Gly Ser Asp Pro Leu Thr Phe
1               5                   10

<210> SEQ ID NO 163
<211> LENGTH: 10
<212> TYPE: PRT
<213> ORGANISM: Artificial Sequence
<220> FEATURE:
<223> OTHER INFORMATION: anti-C-MET antibody molecule or antigen-binding
      portion LCDR3

<400> SEQUENCE: 163

Gln Gln Tyr Gly Ser Glu Pro Leu Thr Phe
1               5                   10

<210> SEQ ID NO 164
<211> LENGTH: 10
<212> TYPE: PRT
<213> ORGANISM: Artificial Sequence
<220> FEATURE:
<223> OTHER INFORMATION: anti-C-MET antibody molecule or antigen-binding
      portion LCDR3

<400> SEQUENCE: 164

Gln Gln Tyr Lys Glu Glu Pro Leu Thr Phe
1               5                   10

<210> SEQ ID NO 165
<211> LENGTH: 10
<212> TYPE: PRT
<213> ORGANISM: Artificial Sequence
<220> FEATURE:
<223> OTHER INFORMATION: anti-C-MET antibody molecule or antigen-binding
      portion LCDR3

<400> SEQUENCE: 165

Gln Gln Tyr Lys Glu Ser Pro Leu Thr Phe
1               5                   10

<210> SEQ ID NO 166
<211> LENGTH: 10
<212> TYPE: PRT
<213> ORGANISM: Artificial Sequence
<220> FEATURE:
<223> OTHER INFORMATION: anti-C-MET antibody molecule or antigen-binding
      portion LCDR3

<400> SEQUENCE: 166

Gln Gln Tyr Lys Ser Asp Pro Leu Thr Phe
1               5                   10
```

<210> SEQ ID NO 167
<211> LENGTH: 10
<212> TYPE: PRT
<213> ORGANISM: Artificial Sequence
<220> FEATURE:
<223> OTHER INFORMATION: anti-C-MET antibody molecule or antigen-binding
      portion LCDR3

<400> SEQUENCE: 167

Gln Gln Tyr Lys Ser Ser Pro Leu Thr Phe
1               5                   10

<210> SEQ ID NO 168
<211> LENGTH: 10
<212> TYPE: PRT
<213> ORGANISM: Artificial Sequence
<220> FEATURE:
<223> OTHER INFORMATION: anti-C-MET antibody molecule or antigen-binding
      portion HCDR1

<400> SEQUENCE: 168

Gly Tyr Ile Phe Thr Ala Tyr Tyr Met His
1               5                   10

<210> SEQ ID NO 169
<211> LENGTH: 10
<212> TYPE: PRT
<213> ORGANISM: Artificial Sequence
<220> FEATURE:
<223> OTHER INFORMATION: anti-C-MET antibody molecule or antigen-binding
      portion HCDR1

<400> SEQUENCE: 169

Gly Tyr Ile Phe Thr Ser Tyr Tyr Met His
1               5                   10

<210> SEQ ID NO 170
<211> LENGTH: 10
<212> TYPE: PRT
<213> ORGANISM: Artificial Sequence
<220> FEATURE:
<223> OTHER INFORMATION: anti-C-MET antibody molecule or antigen-binding
      portion HCDR1

<400> SEQUENCE: 170

Gly Tyr Thr Phe Thr Ala Tyr Ser Met His
1               5                   10

<210> SEQ ID NO 171
<211> LENGTH: 10
<212> TYPE: PRT
<213> ORGANISM: Artificial Sequence
<220> FEATURE:
<223> OTHER INFORMATION: anti-C-MET antibody molecule or antigen-binding
      portion HCDR1

<400> SEQUENCE: 171

Gly Tyr Thr Phe Thr Ala Tyr Thr Met His
1               5                   10

<210> SEQ ID NO 172
<211> LENGTH: 10
<212> TYPE: PRT
<213> ORGANISM: Artificial Sequence
<220> FEATURE:
<223> OTHER INFORMATION: anti-C-MET antibody molecule or antigen-binding
      portion HCDR1

```
<400> SEQUENCE: 172

Gly Tyr Thr Phe Thr Ala Tyr Tyr Met His
1               5                   10

<210> SEQ ID NO 173
<211> LENGTH: 10
<212> TYPE: PRT
<213> ORGANISM: Artificial Sequence
<220> FEATURE:
<223> OTHER INFORMATION: anti-C-MET antibody molecule or antigen-binding
      portion HCDR1

<400> SEQUENCE: 173

Gly Tyr Thr Phe Thr Ser Tyr Tyr Met His
1               5                   10

<210> SEQ ID NO 174
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 174

Met Gly Ile Ile Lys Pro Asn Gly Gly Leu Ala Ser Tyr Ala Gln Lys
1               5                   10                  15

Phe Gln Gly

<210> SEQ ID NO 175
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 175

Met Gly Ile Ile Lys Pro Asn Gly Gly Ser Thr Ser Tyr Ala Gln Lys
1               5                   10                  15

Phe Gln Gly

<210> SEQ ID NO 176
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 176

Met Gly Ile Ile Lys Pro Asn Asn Gly Ser Thr Ser Tyr Ala Gln Lys
1               5                   10                  15

Phe Gln Gly

<210> SEQ ID NO 177
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 177

Met Gly Ile Ile Lys Pro Ser Asn Gly Ser Thr Ser Tyr Ala Gln Lys
```

```
1               5                   10                  15

Phe Gln Gly

<210> SEQ ID NO 178
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 178

Met Gly Ile Ile Asn Pro Asn Asn Gly Ser Ala Ser Tyr Ala Gln Lys
1               5                   10                  15

Phe Gln Gly

<210> SEQ ID NO 179
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 179

Met Gly Ile Ile Asn Pro Ser Gly Gly Leu Ala Asn Tyr Ala Gln Lys
1               5                   10                  15

Phe Gln Gly

<210> SEQ ID NO 180
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 180

Met Gly Ile Ile Asn Pro Ser Gly Gly Ser Thr Asn Tyr Ala Gln Lys
1               5                   10                  15

Phe Gln Gly

<210> SEQ ID NO 181
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 181

Met Gly Trp Ile Lys Pro Asn Gly Gly Ser Thr Asn Tyr Ala Gln Lys
1               5                   10                  15

Phe Gln Gly

<210> SEQ ID NO 182
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 182
```

```
Met Gly Trp Ile Lys Pro Ser Gly Gly Ser Thr Ser Tyr Ala Gln Lys
1               5                   10                  15

Phe Gln Gly
```

<210> SEQ ID NO 183
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 183

```
Met Gly Trp Ile Lys Pro Ser Asn Gly Leu Ala Ser Tyr Ala Gln Lys
1               5                   10                  15

Phe Gln Gly
```

<210> SEQ ID NO 184
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 184

```
Met Gly Trp Ile Lys Pro Ser Asn Gly Ser Ala Asn Tyr Ala Gln Lys
1               5                   10                  15

Phe Gln Gly
```

<210> SEQ ID NO 185
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 185

```
Met Gly Trp Ile Lys Pro Ser Asn Gly Ser Ala Ser Tyr Ala Gln Lys
1               5                   10                  15

Phe Gln Gly
```

<210> SEQ ID NO 186
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 186

```
Met Gly Trp Ile Lys Pro Ser Asn Gly Ser Thr Ser Tyr Ala Gln Lys
1               5                   10                  15

Phe Gln Gly
```

<210> SEQ ID NO 187
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 187

Met Gly Trp Ile Asn Pro Asn Gly Gly Leu Thr Ser Tyr Ala Gln Lys
1               5                   10                  15

Phe Gln Gly

<210> SEQ ID NO 188
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 188

Met Gly Trp Ile Asn Pro Asn Asn Gly Leu Ala Asn Tyr Ala Gln Lys
1               5                   10                  15

Phe Gln Gly

<210> SEQ ID NO 189
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 189

Met Gly Trp Ile Asn Pro Asn Asn Gly Leu Ala Ser Tyr Ala Gln Lys
1               5                   10                  15

Phe Gln Gly

<210> SEQ ID NO 190
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 190

Met Gly Trp Ile Asn Pro Ser Gly Gly Leu Ala Ser Tyr Ala Gln Lys
1               5                   10                  15

Phe Gln Gly

<210> SEQ ID NO 191
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 191

Met Gly Trp Ile Asn Pro Ser Gly Gly Ser Ala Ser Tyr Ala Gln Lys
1               5                   10                  15

Phe Gln Gly

<210> SEQ ID NO 192
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

```
<400> SEQUENCE: 192

Met Gly Trp Ile Asn Pro Ser Asn Gly Leu Thr Asn Tyr Ala Gln Lys
1               5                   10                  15

Phe Gln Gly

<210> SEQ ID NO 193
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 193

Met Gly Ile Ile Lys Pro Ser Gly Gly Ser Thr Asn Tyr Ala Gln Lys
1               5                   10                  15

Phe Gln Gly

<210> SEQ ID NO 194
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 194

Met Gly Ile Ile Lys Pro Ser Asn Gly Leu Ala Ser Tyr Ala Gln Lys
1               5                   10                  15

Phe Gln Gly

<210> SEQ ID NO 195
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 195

Met Gly Ile Ile Asn Pro Asn Gly Gly Leu Thr Asn Tyr Ala Gln Lys
1               5                   10                  15

Phe Gln Gly

<210> SEQ ID NO 196
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 196

Met Gly Ile Ile Asn Pro Asn Gly Gly Leu Thr Ser Tyr Ala Gln Lys
1               5                   10                  15

Phe Gln Gly

<210> SEQ ID NO 197
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2
```

```
<400> SEQUENCE: 197

Met Gly Ile Ile Asn Pro Asn Gly Gly Ser Ala Asn Tyr Ala Gln Lys
1               5                   10                  15

Phe Gln Gly

<210> SEQ ID NO 198
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 198

Met Gly Ile Ile Asn Pro Asn Gly Gly Ser Thr Asn Tyr Ala Gln Lys
1               5                   10                  15

Phe Gln Gly

<210> SEQ ID NO 199
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 199

Met Gly Ile Ile Asn Pro Asn Asn Gly Leu Ala Ser Tyr Ala Gln Lys
1               5                   10                  15

Phe Gln Gly

<210> SEQ ID NO 200
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 200

Met Gly Ile Ile Asn Pro Ser Gly Gly Ser Ala Ser Tyr Ala Gln Lys
1               5                   10                  15

Phe Gln Gly

<210> SEQ ID NO 201
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 201

Met Gly Ile Ile Asn Pro Ser Asn Gly Leu Ala Asn Tyr Ala Gln Lys
1               5                   10                  15

Phe Gln Gly

<210> SEQ ID NO 202
<211> LENGTH: 19
<212> TYPE: PRT
<213> ORGANISM: Artificial Sequence
<220> FEATURE:
<223> OTHER INFORMATION: anti-C-MET antibody molecule or antigen-binding
```

```
            portion HCDR2

<400> SEQUENCE: 202

Met Gly Ile Ile Asn Pro Ser Asn Gly Leu Ala Ser Tyr Ala Gln Lys
1               5                   10                  15

Phe Gln Gly

<210> SEQ ID NO 203
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 203

Met Gly Ile Ile Asn Pro Ser Asn Gly Leu Thr Ser Tyr Ala Gln Lys
1               5                   10                  15

Phe Gln Gly

<210> SEQ ID NO 204
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 204

Met Gly Ile Ile Asn Pro Ser Asn Gly Ser Ala Asn Tyr Ala Gln Lys
1               5                   10                  15

Phe Gln Gly

<210> SEQ ID NO 205
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 205

Met Gly Trp Ile Lys Pro Asn Gly Gly Leu Ala Asn Tyr Ala Gln Lys
1               5                   10                  15

Phe Gln Gly

<210> SEQ ID NO 206
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 206

Met Gly Trp Ile Lys Pro Asn Gly Gly Ser Ala Ser Tyr Ala Gln Lys
1               5                   10                  15

Phe Gln Gly

<210> SEQ ID NO 207
<211> LENGTH: 19
<212> TYPE: PRT
<213> ORGANISM: Artificial Sequence
<220> FEATURE:
```

```
<223> OTHER INFORMATION: anti-C-MET antibody molecule or antigen-binding
      portion HCDR2

<400> SEQUENCE: 207

Met Gly Trp Ile Lys Pro Asn Gly Gly Ser Thr Ser Tyr Ala Gln Lys
1               5                   10                  15

Phe Gln Gly

<210> SEQ ID NO 208
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 208

Met Gly Trp Ile Lys Pro Asn Asn Gly Ser Thr Ser Tyr Ala Gln Lys
1               5                   10                  15

Phe Gln Gly

<210> SEQ ID NO 209
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 209

Met Gly Trp Ile Asn Pro Asn Gly Gly Leu Thr Asn Tyr Ala Gln Lys
1               5                   10                  15

Phe Gln Gly

<210> SEQ ID NO 210
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 210

Met Gly Trp Ile Asn Pro Asn Gly Gly Ser Thr Asn Tyr Ala Gln Lys
1               5                   10                  15

Phe Gln Gly

<210> SEQ ID NO 211
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 211

Met Gly Trp Ile Asn Pro Asn Asn Gly Ser Thr Ser Tyr Ala Gln Lys
1               5                   10                  15

Phe Gln Gly

<210> SEQ ID NO 212
<211> LENGTH: 19
<212> TYPE: PRT
<213> ORGANISM: Artificial Sequence
```

```
<220> FEATURE:
<223> OTHER INFORMATION: anti-C-MET antibody molecule or antigen-binding
      portion HCDR2

<400> SEQUENCE: 212

Met Gly Trp Ile Asn Pro Ser Gly Gly Leu Thr Ser Tyr Ala Gln Lys
1               5                   10                  15

Phe Gln Gly

<210> SEQ ID NO 213
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 213

Met Gly Trp Ile Asn Pro Ser Gly Gly Ser Ala Asn Tyr Ala Gln Lys
1               5                   10                  15

Phe Gln Gly

<210> SEQ ID NO 214
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 214

Met Gly Trp Ile Asn Pro Ser Gly Gly Ser Thr Asn Tyr Ala Gln Lys
1               5                   10                  15

Phe Gln Gly

<210> SEQ ID NO 215
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 215

Met Gly Ile Ile Lys Pro Asn Gly Gly Ser Ala Asn Tyr Ala Gln Lys
1               5                   10                  15

Phe Gln Gly

<210> SEQ ID NO 216
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 216

Met Gly Ile Ile Lys Pro Asn Asn Gly Ser Ala Ser Tyr Ala Gln Lys
1               5                   10                  15

Phe Gln Gly

<210> SEQ ID NO 217
<211> LENGTH: 19
<212> TYPE: PRT
```

```
<213> ORGANISM: Artificial Sequence
<220> FEATURE:
<223> OTHER INFORMATION: anti-C-MET antibody molecule or antigen-binding
      portion HCDR2

<400> SEQUENCE: 217

Met Gly Ile Ile Lys Pro Ser Gly Gly Leu Ala Asn Tyr Ala Gln Lys
1               5                   10                  15

Phe Gln Gly

<210> SEQ ID NO 218
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 218

Met Gly Ile Ile Lys Pro Ser Asn Gly Ser Ala Ser Tyr Ala Gln Lys
1               5                   10                  15

Phe Gln Gly

<210> SEQ ID NO 219
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 219

Met Gly Ile Ile Asn Pro Asn Gly Gly Leu Ala Ser Tyr Ala Gln Lys
1               5                   10                  15

Phe Gln Gly

<210> SEQ ID NO 220
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 220

Met Gly Ile Ile Asn Pro Asn Gly Gly Ser Ala Ser Tyr Ala Gln Lys
1               5                   10                  15

Phe Gln Gly

<210> SEQ ID NO 221
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 221

Met Gly Ile Ile Asn Pro Asn Asn Gly Leu Ala Asn Tyr Ala Gln Lys
1               5                   10                  15

Phe Gln Gly

<210> SEQ ID NO 222
<211> LENGTH: 19
```

```
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 222

Met Gly Ile Ile Asn Pro Ser Gly Gly Leu Ala Ser Tyr Ala Gln Lys
1               5                   10                  15

Phe Gln Gly

<210> SEQ ID NO 223
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 223

Met Gly Ile Ile Asn Pro Ser Asn Gly Ser Thr Asn Tyr Ala Gln Lys
1               5                   10                  15

Phe Gln Gly

<210> SEQ ID NO 224
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 224

Met Gly Ile Ile Asn Pro Ser Asn Gly Ser Thr Ser Tyr Ala Gln Lys
1               5                   10                  15

Phe Gln Gly

<210> SEQ ID NO 225
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 225

Met Gly Trp Ile Lys Pro Asn Gly Gly Leu Thr Ser Tyr Ala Gln Lys
1               5                   10                  15

Phe Gln Gly

<210> SEQ ID NO 226
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 226

Met Gly Trp Ile Lys Pro Asn Asn Gly Leu Thr Ser Tyr Ala Gln Lys
1               5                   10                  15

Phe Gln Gly

<210> SEQ ID NO 227
```

```
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 227

Met Gly Trp Ile Lys Pro Asn Asn Gly Ser Ala Asn Tyr Ala Gln Lys
1               5                   10                  15

Phe Gln Gly

<210> SEQ ID NO 228
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 228

Met Gly Trp Ile Lys Pro Ser Gly Gly Leu Thr Ser Tyr Ala Gln Lys
1               5                   10                  15

Phe Gln Gly

<210> SEQ ID NO 229
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 229

Met Gly Trp Ile Lys Pro Ser Asn Gly Leu Thr Ser Tyr Ala Gln Lys
1               5                   10                  15

Phe Gln Gly

<210> SEQ ID NO 230
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 230

Met Gly Trp Ile Lys Pro Ser Asn Gly Ser Thr Asn Tyr Ala Gln Lys
1               5                   10                  15

Phe Gln Gly

<210> SEQ ID NO 231
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 231

Met Gly Trp Ile Asn Pro Asn Gly Gly Ser Ala Ser Tyr Ala Gln Lys
1               5                   10                  15

Phe Gln Gly
```

```
<210> SEQ ID NO 232
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 232

Met Gly Trp Ile Asn Pro Asn Asn Gly Leu Thr Asn Tyr Ala Gln Lys
1               5                   10                  15

Phe Gln Gly

<210> SEQ ID NO 233
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 233

Met Gly Trp Ile Asn Pro Asn Asn Gly Ser Ala Asn Tyr Ala Gln Lys
1               5                   10                  15

Phe Gln Gly

<210> SEQ ID NO 234
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 234

Met Gly Trp Ile Asn Pro Asn Asn Gly Ser Ala Ser Tyr Ala Gln Lys
1               5                   10                  15

Phe Gln Gly

<210> SEQ ID NO 235
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 235

Met Gly Trp Ile Asn Pro Ser Gly Gly Leu Thr Asn Tyr Ala Gln Lys
1               5                   10                  15

Phe Gln Gly

<210> SEQ ID NO 236
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 236

Met Gly Trp Ile Asn Pro Ser Asn Gly Ser Ala Ser Tyr Ala Gln Lys
1               5                   10                  15

Phe Gln Gly
```

```
<210> SEQ ID NO 237
<211> LENGTH: 19
<212> TYPE: PRT
<213> ORGANISM: Artificial Sequence
<220> FEATURE:
<223> OTHER INFORMATION: anti-C-MET antibody molecule or antigen-binding
      portion HCDR2

<400> SEQUENCE: 237

Met Gly Trp Ile Asn Pro Ser Asn Gly Ser Thr Ser Tyr Ala Gln Lys
1               5                   10                  15

Phe Gln Gly

<210> SEQ ID NO 238
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion HCDR3

<400> SEQUENCE: 238

His Glu Ile Thr Thr Glu Phe Asp Tyr
1               5

<210> SEQ ID NO 239
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion HCDR3

<400> SEQUENCE: 239

Met Glu Ile Thr Thr Glu Phe Asp Tyr
1               5

<210> SEQ ID NO 240
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion HCDR3

<400> SEQUENCE: 240

Gln Glu Ile Thr Thr Glu Leu Asp Tyr
1               5

<210> SEQ ID NO 241
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion HCDR3

<400> SEQUENCE: 241

Ser Glu Ile Thr Thr Glu Glu Asp Tyr
1               5

<210> SEQ ID NO 242
<211> LENGTH: 9
<212> TYPE: PRT
<213> ORGANISM: Artificial Sequence
<220> FEATURE:
<223> OTHER INFORMATION: anti-C-MET antibody molecule or antigen-binding
```

```
                            portion HCDR3

<400> SEQUENCE: 242

Ser Glu Ile Thr Thr Glu Phe Asp Ala
1               5

<210> SEQ ID NO 243
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion HCDR3

<400> SEQUENCE: 243

Ser Glu Ile Thr Thr Glu Phe Asp Glu
1               5

<210> SEQ ID NO 244
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion HCDR3

<400> SEQUENCE: 244

Ser Glu Ile Thr Thr Glu Phe Asp Phe
1               5

<210> SEQ ID NO 245
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion HCDR3

<400> SEQUENCE: 245

Ser Glu Ile Thr Thr Glu Phe Asp Ile
1               5

<210> SEQ ID NO 246
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion HCDR3

<400> SEQUENCE: 246

Ser Glu Ile Thr Thr Glu Phe Asp Lys
1               5

<210> SEQ ID NO 247
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion HCDR3

<400> SEQUENCE: 247

Ser Glu Ile Thr Thr Glu Phe Asp Leu
1               5

<210> SEQ ID NO 248
```

```
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion HCDR3

<400> SEQUENCE: 248

Ser Glu Ile Thr Thr Glu Phe Asp Met
1               5

<210> SEQ ID NO 249
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion HCDR3

<400> SEQUENCE: 249

Ser Glu Ile Thr Thr Glu Phe Asp Gln
1               5

<210> SEQ ID NO 250
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion HCDR3

<400> SEQUENCE: 250

Ser Glu Ile Thr Thr Glu Phe Asp Ser
1               5

<210> SEQ ID NO 251
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion HCDR3

<400> SEQUENCE: 251

Ser Glu Ile Thr Thr Glu Phe Asp Val
1               5

<210> SEQ ID NO 252
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion HCDR3

<400> SEQUENCE: 252

Ser Glu Ile Thr Thr Glu Phe Asp Trp
1               5

<210> SEQ ID NO 253
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion HCDR3

<400> SEQUENCE: 253
```

```
Ser Glu Ile Thr Thr Glu Leu Asp Tyr
1               5

<210> SEQ ID NO 254
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion HCDR3

<400> SEQUENCE: 254

Ser Glu Ile Thr Thr Glu Trp Asp Tyr
1               5

<210> SEQ ID NO 255
<211> LENGTH: 9
<212> TYPE: PRT
<213> ORGANISM: Artificial Sequence
<220> FEATURE:
<223> OTHER INFORMATION: anti-C-MET antibody molecule or antigen-binding
      portion HCDR3

<400> SEQUENCE: 255

Val Glu Ile Thr Thr Glu Phe Asp Leu
1               5
```